(12) United States Patent
Zheng et al.

(10) Patent No.: US 8,133,482 B2
(45) Date of Patent: Mar. 13, 2012

(54) ACTIVATABLE PHOTODYNAMIC THERAPY AGENTS

(75) Inventors: Gang Zheng, Westgrove, PA (US);
Jerry P. Glickson, Ambler, PA (US);
Britton Chance, Marathon, FL (US);
Edward James Delikatny, Havertown, PA (US); Klara Stefflova, Philadelphia, PA (US); Juan Chen, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 568 days.

(21) Appl. No.: 11/383,487

(22) Filed: May 15, 2006

(65) Prior Publication Data

US 2008/0193431 A1 Aug. 14, 2008

Related U.S. Application Data

(63) Continuation-in-part of application No. PCT/US2004/038024, filed on Nov. 15, 2004.

(60) Provisional application No. 60/695,156, filed on Jun. 29, 2005, provisional application No. 60/558,501, filed on Apr. 1, 2004, provisional application No. 60/519,794, filed on Nov. 14, 2003.

(51) Int. Cl.
| | |
|---|---|
| *A61K 38/43* | (2006.01) |
| *A61K 38/46* | (2006.01) |
| *A61K 38/47* | (2006.01) |
| *A61K 38/48* | (2006.01) |
| *C12N 9/00* | (2006.01) |

(52) U.S. Cl. ... 424/94.1; 435/183; 424/9.61; 424/94.63; 424/94.65

(58) Field of Classification Search .................. None
See application file for complete search history.

(56) References Cited

OTHER PUBLICATIONS

DeRosa, M.C. and Crutchley, R.J. "Photosensitized singlet oxygen and its applications" Coord.Chem.Rev. 2002, vol. 233-234, pp. 351-371.*

Linder,K.E.,et al"Black Hole Quencher 3(BHQ-3) quenches fluorescence from IRDye800 but is unstable in vivo—a tale of two compounds" Abs. 2009 World Molec. Imag. Cong. (WMIC)—Montréal,Sep. 23-26, 2009, Abs. 0764, 1 page [retrieved on May 21, 2010]. Retrieved from the Internet:< URL: http://www.wmicmeeting.org/abstracts/data/papers/0764.html>.*

Sigma "Significantly Improved Signal-to-Noise Ratios using Black Hole Quencher (BHQ™) Dyes" Sigma-Genosys BHQprobes ProductGuide, 4 pages [retrieved on May 21, 2010]. Retrieved from the Internet:< URL:https://www.sigma-genosys.com/media/BHQprobes_ProductGuide.pdf>.*

* cited by examiner

*Primary Examiner* — Chris R Tate
*Assistant Examiner* — Aaron J Kosar
(74) *Attorney, Agent, or Firm* — Mark S. Cohen; Pearl Cohen Zedek Latzer, LLP

(57) ABSTRACT

The present invention relates to the field of conjugates comprising a substrate which is attached to at least one photoactivatable killing agent and at least one first quencher, and methods for their use. More particularly, the present invention relates to photodynamic therapy agents. The invention further relates to methods for decontaminating blood and methods for treating cancer or viral infection in a subject using the conjugates of the present invention.

15 Claims, 39 Drawing Sheets

Scheme 1: Concept of enzyme-activated PDT agent with a built-in cell death sensor.
($Q_f$: Fluorescent quencher; P: Photosensitizer/fluorophore; $Q_s$: Singlet oxygen quencher)

Protocol 2c2: a) Removing Fmoc, b) Labeling BChl, c) Cleaving CPG, d) Forming phosphoramidite, e) Syntheszing DNA from 3'-amino-modifier C7-CPG, f) Labeling Car at 3'-end, g) Removing DMT, h) Linking ANT peptide via S-S bond.

A

B

C

D

Mouse #2 -HT 1080 tumor (Folate receptor -)

Mouse #1 -KB tumor (Folate receptor +)

A: 2 h post iv injection, before PDT;
B: 5 h post iv injection, 2 h after PDT

ACTIVATABLE PHOTODYNAMIC THERAPY AGENTS

CROSS-REFERENCE TO RELATED APPLICATIONS

This application claims the benefit of priority from U.S. provisional application No. 60/695,156, filed Jun. 29, 2005, and is a continuation-in-part application of PCT application No. PCT/US04/38024, filed Nov. 15, 2004, which claims the benefit of priority from U.S. provisional application No. 60/558,501, filed Apr. 1, 2004, and U.S. provisional application No. 60/519,794, filed Nov. 14, 2003, which are all herein incorporated by reference in their entireties.

BACKGROUND OF THE INVENTION

Field of the Invention

The present invention relates to the field of photodynamic therapy agents and cell-death detection agents. The invention further relates to compositions and methods for decontaminating blood and treating disease such as cancer or viral infection in a subject using the photodynamic therapy agents of the present invention.

BACKGROUND

Photodynamic Therapy

Photodynamic therapy (PDT) is a minimally invasive treatment modality for many diseases such as cancers and age-related macular degeneration. It has also been one of the very few sterilization methods that may be applied to red blood cells (RBCs). PDT involves the combination of light and a photoactivatable killing agent, typically a porphyrin derivative. Each factor is harmless by itself, but when combined with oxygen ($O_2$), lethal reactive oxygen species are produced, such as singlet oxygen ($^1O_2$), which kill tumor cells. $^1O_2$ is a powerful, fairly indiscriminate oxidant that is generally recognized as the key agent of PDT-induced cell or virus damage. Because the diffusion range of $^1O_2$ is much smaller than the diameter of a single cell, the site of the primary generation of $^1O_2$ determines which subcellular structures may be attacked. Consequently, if a photoactivatable killing agent is preferentially localized in target cells, PDT-induced damage will be highly specific. A comprehensive review of porphyrins and their use as photoactivatable killing agents in photodynamic therapy appears in Pandey, R. K. and G. Zheng, "Porphyrins as Photoactivatable killing agents in Photodynamic Therapy" in *The Porphyrin Handbook*, Kadish, K. M. et al. Eds., Academic Press (2000).

PDT has been used to sterilize blood because, although the interviewing of donors and serological screening have greatly reduced the contamination of blood by infectious agents, the risk of viral infections following blood transfusion still remains. Cytomegalovirus (CMV), hepatitis B (HBV) and C(HCV) viruses and human immunodeficiency virus (HIV) are the major causes of blood transfusion-transmitted diseases. To date, PDT has been one of the very few sterilization methods that may be applied to RBCs. When photoactivatable killing agent solutes are illuminated with light of the appropriate wavelength, reactive oxygen species (ROS) are formed, which have potent virucidal action.

Some extent of specificity is anticipated to be inherent in PDT as, in contrast to cells, viruses do not possess defense mechanisms against attack by ROS. For example, RBCs possess antioxidant defense systems that are enzymatic (methemoglobin reductase, superoxide dismutases, catalase, glutathione peroxidase) or nonenzymatic (endogenous scavengers such as reduced fluthathione and the vitamins A, C, and E) but, depending on the type and amount of ROS, these defense systems may fail. Virucidal phototreatment by use of methylene blue, for example, is associated with enhanced hemolysis, potassium leakage, and induction of binding of IgG and serum albumin to the RBC surface.

To prevent RBC damage, most of the research is based on three fronts: 1) to develop photoactivatable killing agent compounds that bind more selectively to viruses; 2) to impart additional protection to RBCs, mainly by inclusion of ROS scavengers, such as Trolox™ a hydrophilic vitamin E derivative (for example, Trolox™), glutathione, mannitol, and the RBC band III ligand dipyridamole; 3) to use long wavelength photoactivatable killing agents that have minimal light absorption by hemoglobin, such as chlorins and phthalocyanines.

In U.S. Pat. No. 6,348,453, PDT has also been suggested as treatment to reduce HIV viremia in the blood of AIDS patients. Reduced HIV viremia in plasma is a predictor for enhanced survival of AIDS patients (Mellors, J. W. et al., Science 272:1167-1170 (1996)). In addition, PDT agents have been used for treatment of early stage lung cancer, obstructive lung cancer, obstructive esophageal cancer, high grade dysplasia (HGD) in Barrett's esophagus, and other neoplasia. Treatment of lung cancer with PDT is recommended as a potentially curative treatment for microinvasive endobronchial cancer in patients who are not good candidates for or have refused surgery or radiation. A particularly new and important application is for the treatment of age-related macular degeneration (AMD), where PDT verteporfin, sold under the trademark Visudyne®, has made a major impact on the outcome of this disease, the major cause of blindness in those over the age of 50. In the cancer field, while not yet approved, the use of PDT in treatment of HGD in Barrett's esophagus may well change how this disease is currently treated, which is often by esophagectomy. Mechanistically, the recognition of apoptosis as an important mode of cell death following PDT and the critical role of the inflammatory process and immunity has only recently been recognized. Dougherty T. J., J. Clin. Laser Med. Surg. 2002 February; 20(1):3-7.

Fluorescence Resonance Energy Transfer

In 1990, Matayoshi et al, reported a fluorogenic substrate for assaying retroviral proteases (Matayoshi et al., Science 247:954 1990) using the concept of fluorescence resonance energy transfer (FRET). This work used the quenched fluorogenic substrate (DABCYL as a quencher)-Ser-Gln-Asn-Tyr-Pro-Ile-Val-Gln-(EDANS as a fluorophore; SEQ ID NO: 17), whose sequence is derived from a natural processing site for HIV protease which is essential for the correct processing of viral polypeptides and the maturation of infectious virus. Thus, incubation of HIV protease with the fluorogenic substrate resulted in specific cleavage at the Tyr-Pro bond and a time-dependent increase in fluorescence intensity which was linearly related to the extent of substrate hydrolysis. This assay has greatly facilitated the development of HIV protease inhibitors for the control and treatment of AIDS. Since then, FRET-based enzyme-activated probes have been widely used in many other biological applications. The most notable one is the protease-activated near-infrared fluorescent probe concept developed by Ralph Weissleder and his colleagues for in vivo imaging of cancers.

If the FRET concept used in enzyme-activated fluorogenic substrates can be used to design novel PDT substrates, the PDT substrates would have a tremendous advantage over the current PDT agents because of greatly enhanced specificity. Greater specificity would ensure that there would be minimal, if any, damage to healthy tissues.

For example, HIV/AIDS is now the fourth biggest killer disease and was the root-cause of death for 2.2 million people in the year 1998. The situation is getting worse, especially in the developing world. Several anti-HIV drugs are now available on the market to control viral replication and to delay the onset of AIDS and death but, to date, no cure is available. At least four of the currently available drugs (saquinavir, indinavir, nelfinavir and ritonavir) work by inhibiting the HIV viral aspartic proteinase that is responsible for processing the viral polyprotein. As a result, HIV proteinase has been extensively characterized in terms of its crystal structure and its substrate specificity. A key feature of this specificity is the ability of the enzyme to cleave N-terminal to a proline residue. Such cleavage is extremely rare and inhibitors designed from proline containing peptidomimetics have proved to be very selective for HIV proteinase (Roberts et al., Science 248:358-361 (1990)). If the FRET concept used in enzyme-activated fluorogenic substrates can be used to design novel PDT substrates for HIV/AIDS, such PDT substrates would have a tremendous advantage over the current therapies.

BRIEF SUMMARY OF THE INVENTION

Recognizing the tremendous therapeutic potential of PDT substrates with enhanced specificity, the present inventors have developed substrates which can undergo a change of conformation in diseased (e.g., cancerous) and/or inflamed tissue.

Accordingly, one aspect of the invention is directed to a conjugate comprising a substrate, at least one photoactivatable killing agent, and at least one first quencher, wherein the photoactivatable killing agent and the first quencher are each attached to said substrate, wherein the substrate brings the photoactivatable killing agent and the first quencher sufficiently close to each other to facilitate quenching of an activated form of the photoactivatable killing agent.

Another aspect of the invention is directed to a conjugate comprising a substrate, a cell death protease recognition sequence wherein the substrate is covalently linked to the cell death protease recognition sequence, a first quencher attached to the substrate, a second quencher attached to the cell death protease recognition sequence wherein the second quencher comprises a fluorescence quencher, and a photoactivatable killing agent attached to the covalently linked substrate and cell death protease recognition sequences wherein the photoactivatable killing agent comprises a fluorophore, wherein the substrate brings the photoactivatable killing agent and the first quencher sufficiently close to each other to facilitate quenching of an activated form of the photoactivatable killing agent, and wherein the cell death protease recognition sequence allows the photoactivatable killing agent and the second quencher to come sufficiently close to each other to facilitate quenching of fluorescence from the fluorophore of the photoactivatable killing agent.

Another aspect of the invention is directed to a conjugate comprising a nucleic acid substrate, at least one photoactivatable killing agent, and at least one first quencher, wherein the photoactivatable killing agent and the at least one at least one first quencher are attached to the substrate, and wherein the substrate brings the photoactivatable killing agent and the first quencher sufficiently close to each other to facilitate quenching of an activated form of the photoactivatable killing agent. In certain embodiments the nucleic acid comprises a first portion, a second portion, and a third portion, wherein the first portion and the third portion are at least about 70% complementary to each other. In other embodiments first portion and the third portion are at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% complementary to each other. In one embodiment, the first portion and the third portion are 100% complementary to each other. In one embodiment, the first portion and the third portion are capable of base pairing with each other resulting in a stem-loop structure wherein the first portion and the third portion form the stem and the second portion forms a non-base-paired loop region.

Another aspect of the invention is directed to a method for decontaminating blood comprising the steps of contacting blood with the conjugates of the present invention, and exposing the blood and substrate mixture to an effective amount of artificial radiation.

A further embodiment of the invention provides a method for treating a disease state comprising the steps of contacting the diseased tissue with the conjugates of the present invention and exposing the diseased tissue to an effective amount of artificial radiation.

Another aspect of the invention is related to a conjugate comprising a cell death protease recognition sequence, a photoactivatable killing agent comprising a fluorophore, a fluorescence quencher, and a targeting ligand. In general, the cell death protease recognition sequences of the present invention serve as a scaffold. In particular, when the cell death protease recognition sequence is intact, the fluorescence quencher and the photoactivatable killing agent are held in proximity such that the fluorescence quencher facilitates quenching of fluorescence from the fluorophore of the photoactivatable killing agent. Once the cell death protease recognition sequence undergoes a conformation change or is cleaved, the fluorescence quencher and the photoactivatable killing agent are no longer held in proximity and the fluorophore of the photoactivatable killing agent is no longer quenched. The resultant fluorescence of the photoactivatable killing agent allows for monitoring of apoptosis.

BRIEF DESCRIPTION OF THE DRAWINGS/FIGURES

FIG. 1 depicts a conjugate which is an activatable PDT agent of the present invention before and after cleavage by an enzyme. "PS" is the photoactivatable killing agent which generates reactive oxygen species (ROS) such as singlet oxygen ($^1O_2$) or superoxide free radicals, and "Q" is the quencher which quenches the triplet state of the photoactivatable killing agent when the photoactivatable killing agent and quencher are in close proximity.

Figure 7:
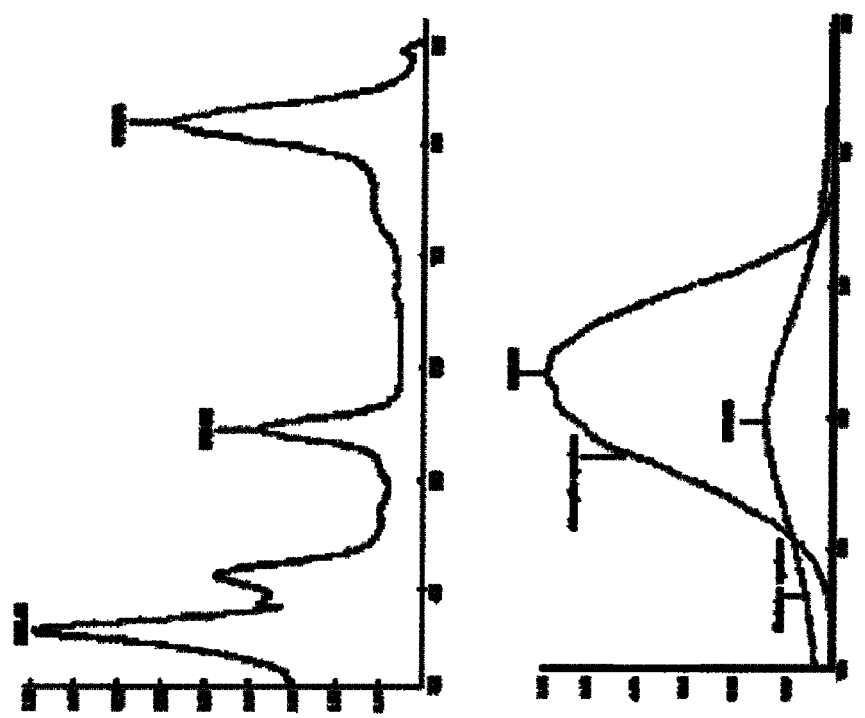
Figure 7:
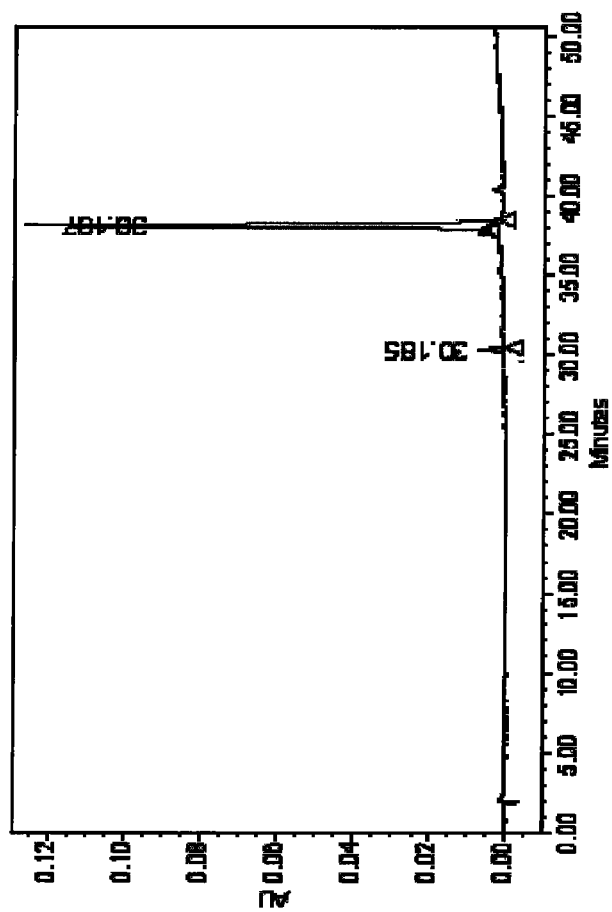

FIG. 7 A) depicts a the HPLC chromatogram of BChlPP-NHS. RP-HPLC Column: ZARBOX-300SB_C8_4.6×250 mm; Solvent A: 0.1% TFA, B: CH3CN; Gradient from 10% B to 100% B for 45 min; Flow: 1 mL/min. At this condition, the retention time of BchlPP-2DG is 38.1 min. Purity of the compound: >90%. B) absorption (top) and emission (bottom) spectra of BChlPP-NHS.

Figure 8:
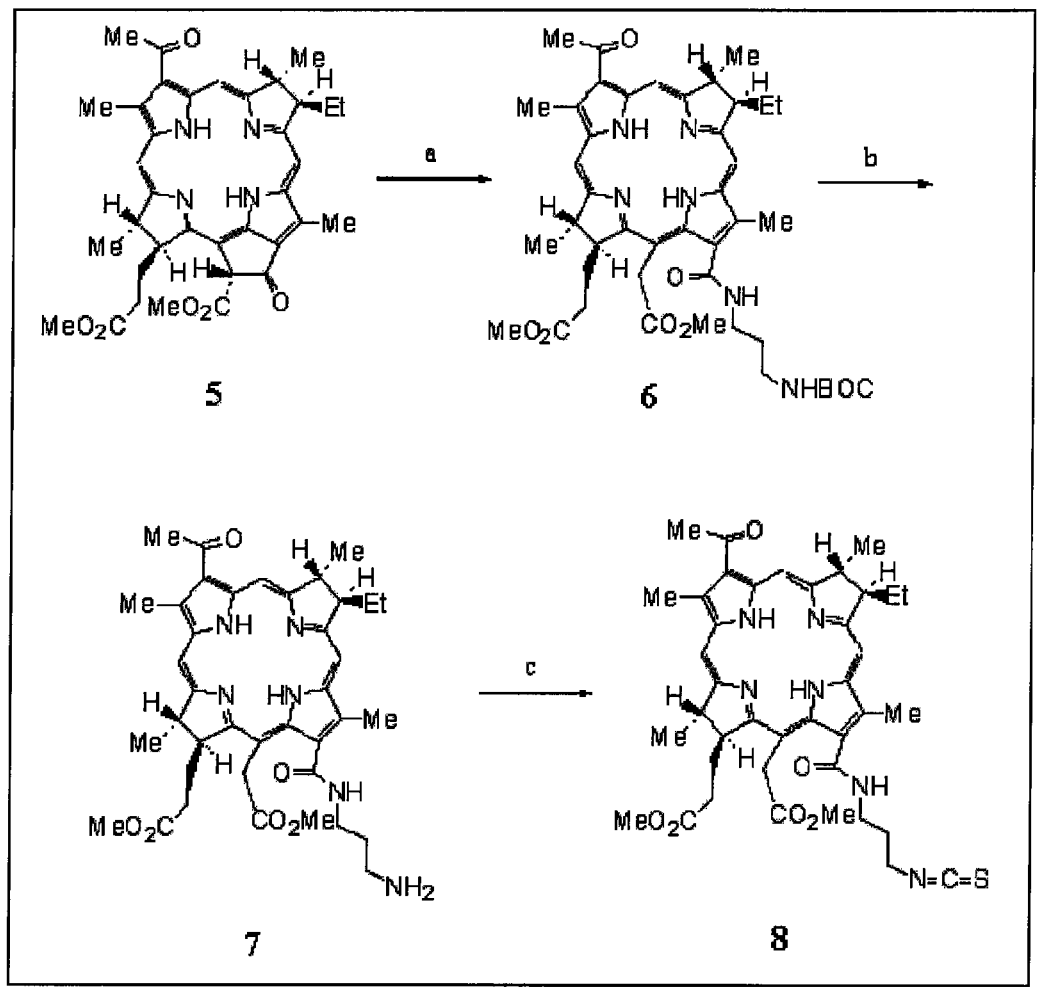

FIG. 8 depicts a synthesis of BChlPP-NHS.

Figure 9:
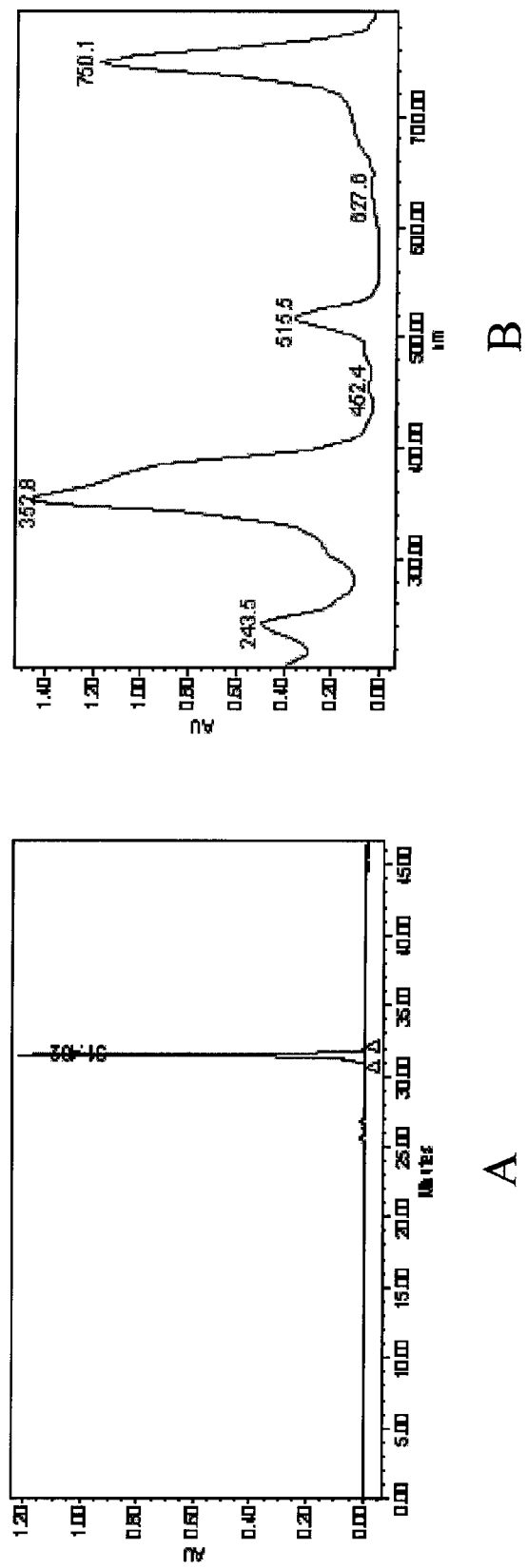

FIG. 9 depicts a A) The HPLC chromatogram of BChlE6 (Retention time: 31.4 min, purity: 99%); and B) the absorption spectrum of the 31.4 min peak (BChlE6) obtained by HPLC. The maximum emission is 758 nm (spectrum not shown).

Figure 10:
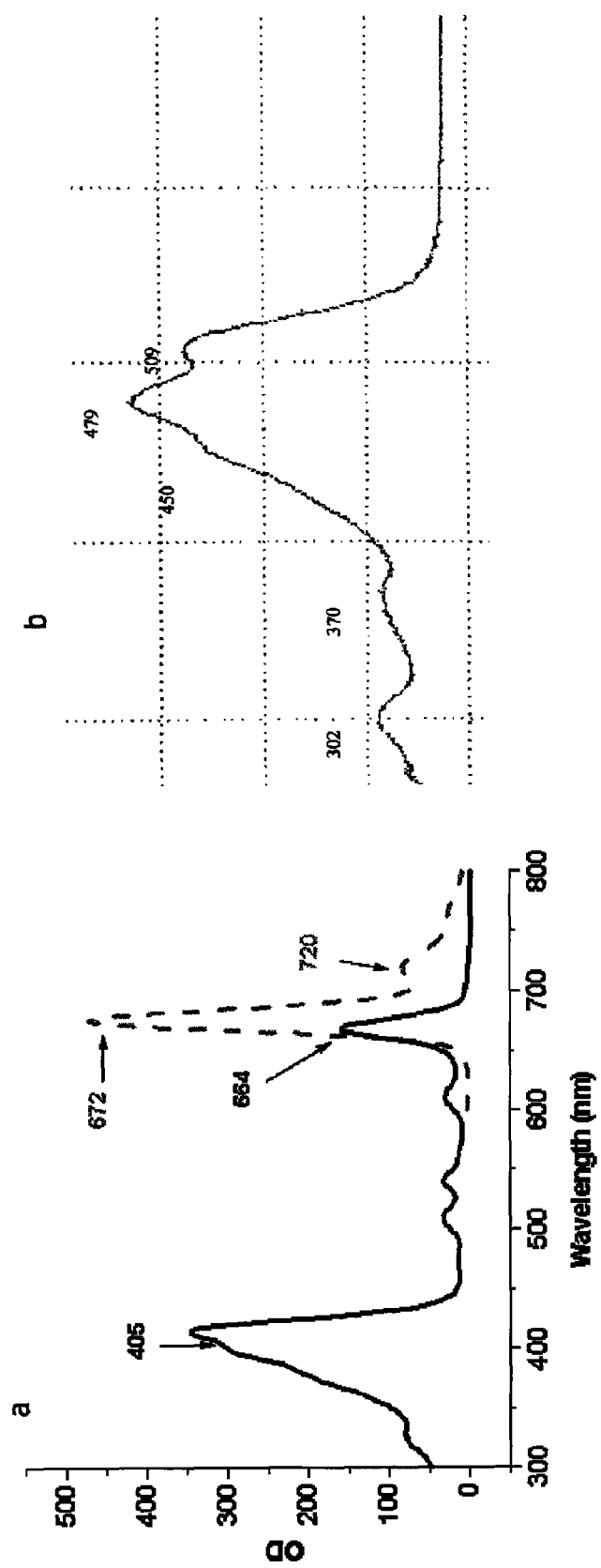

FIG. 10 depicts an absorption spectra of Pyro (a) and Car (b). (note: dotted line (left) indicating the emission spectrum of Pyro).

Figure 11:
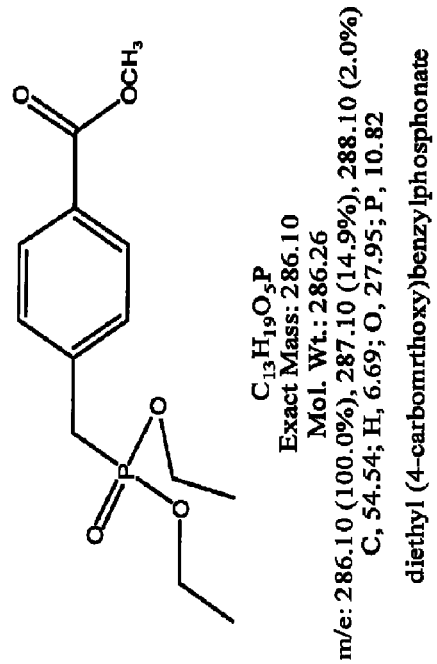
Figure 11:
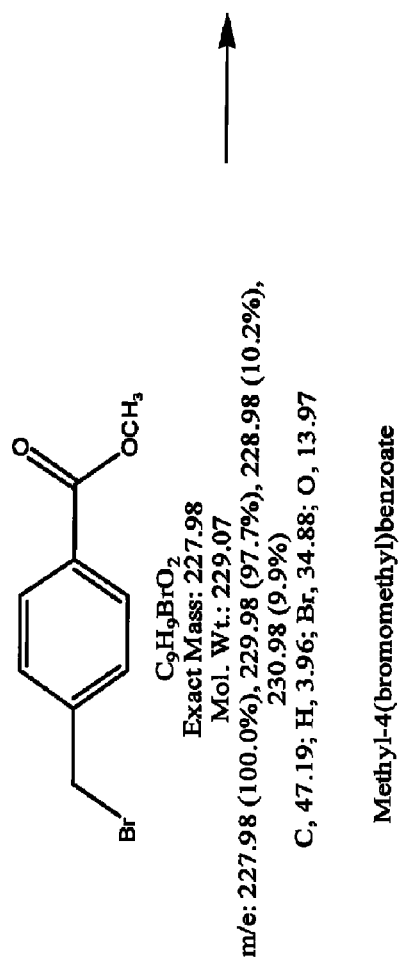
Figure 11:
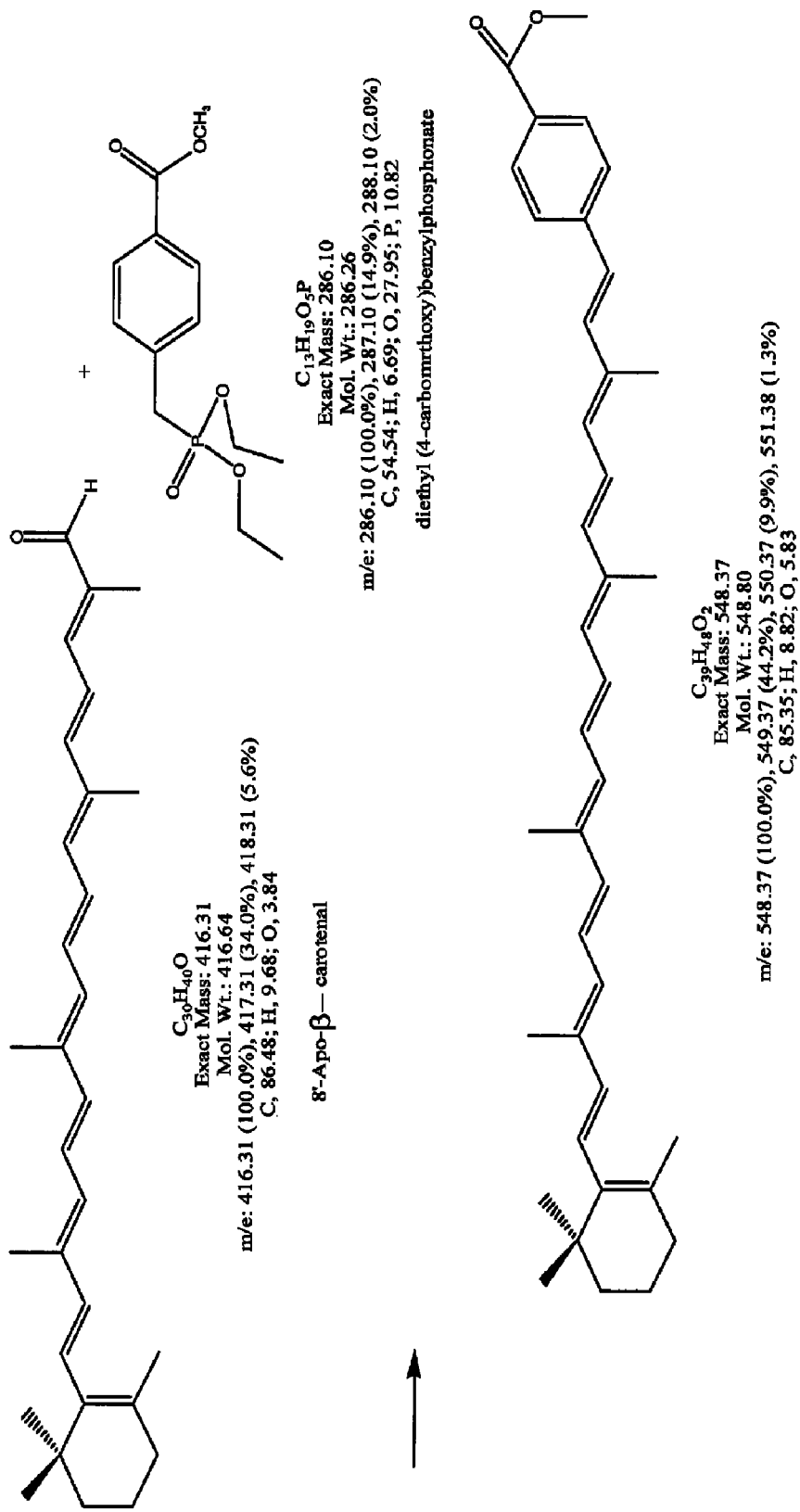

FIG. 11 depicts a preparation of 7'-Apo-7'-(4-Carbomethoxyphenyl)-β-carotene.

Figure 12:
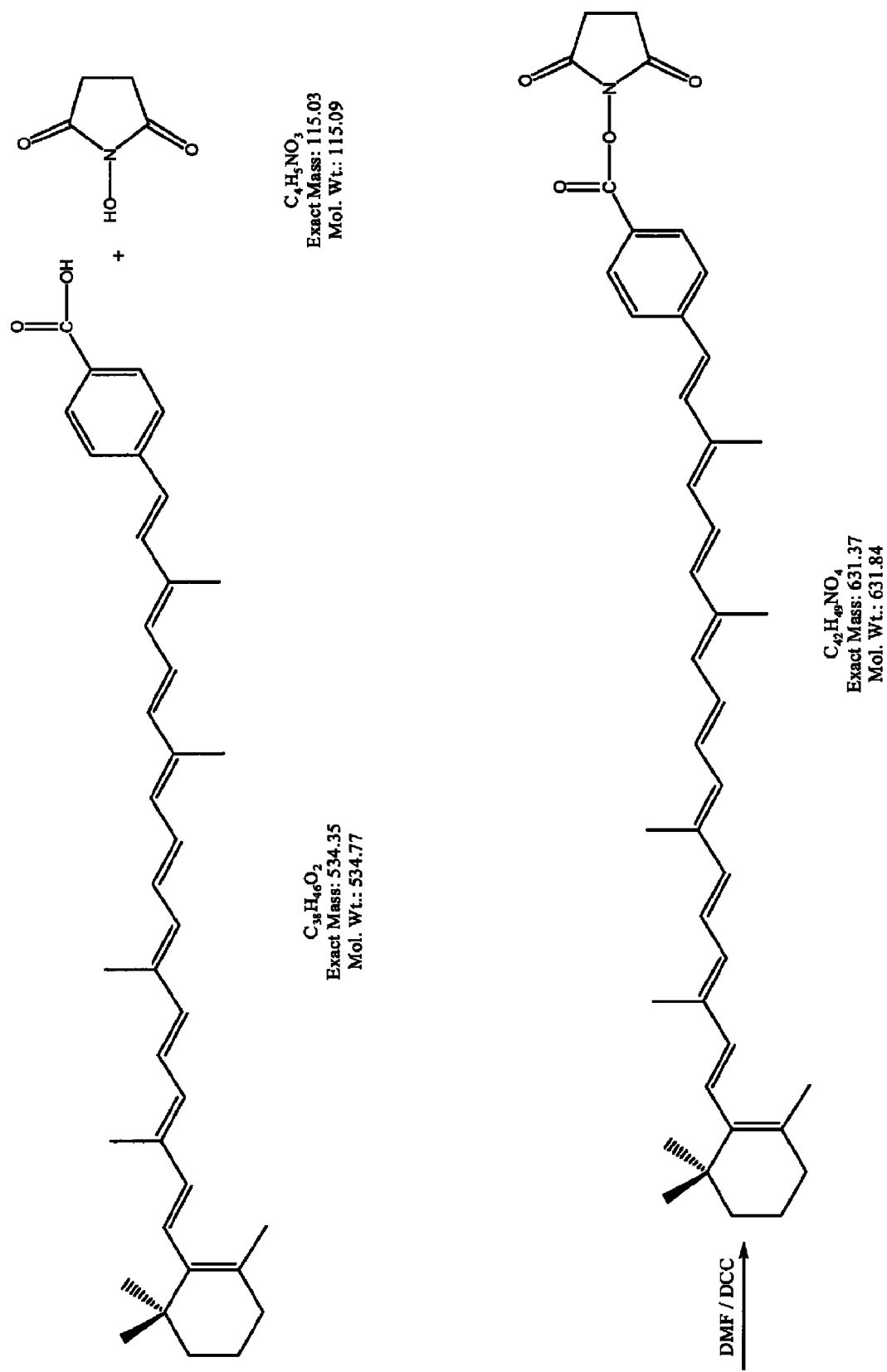

FIG. 12 depicts a preparation of carotenide succinimide ester.

Figure 13:
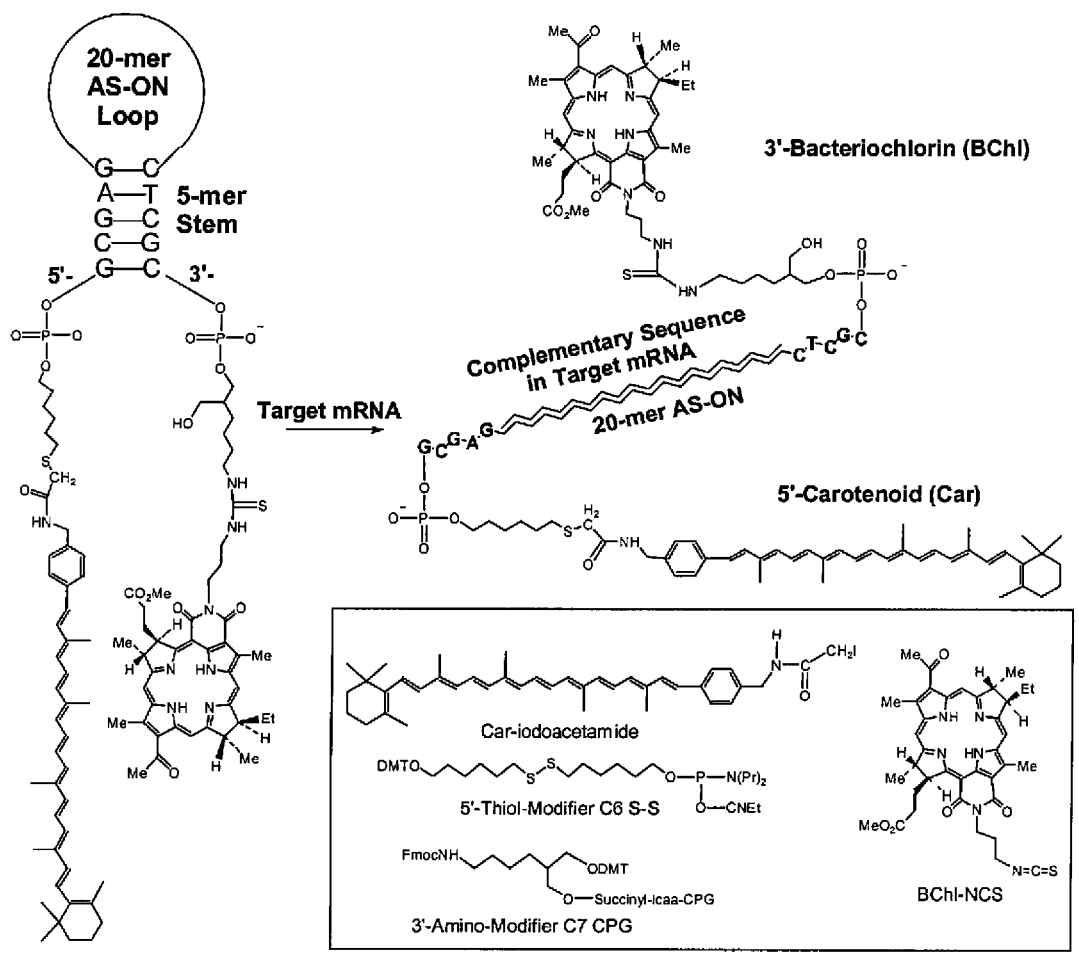

FIG. 13 depicts the molecular structure of BChl-MBs.

Figure 14:
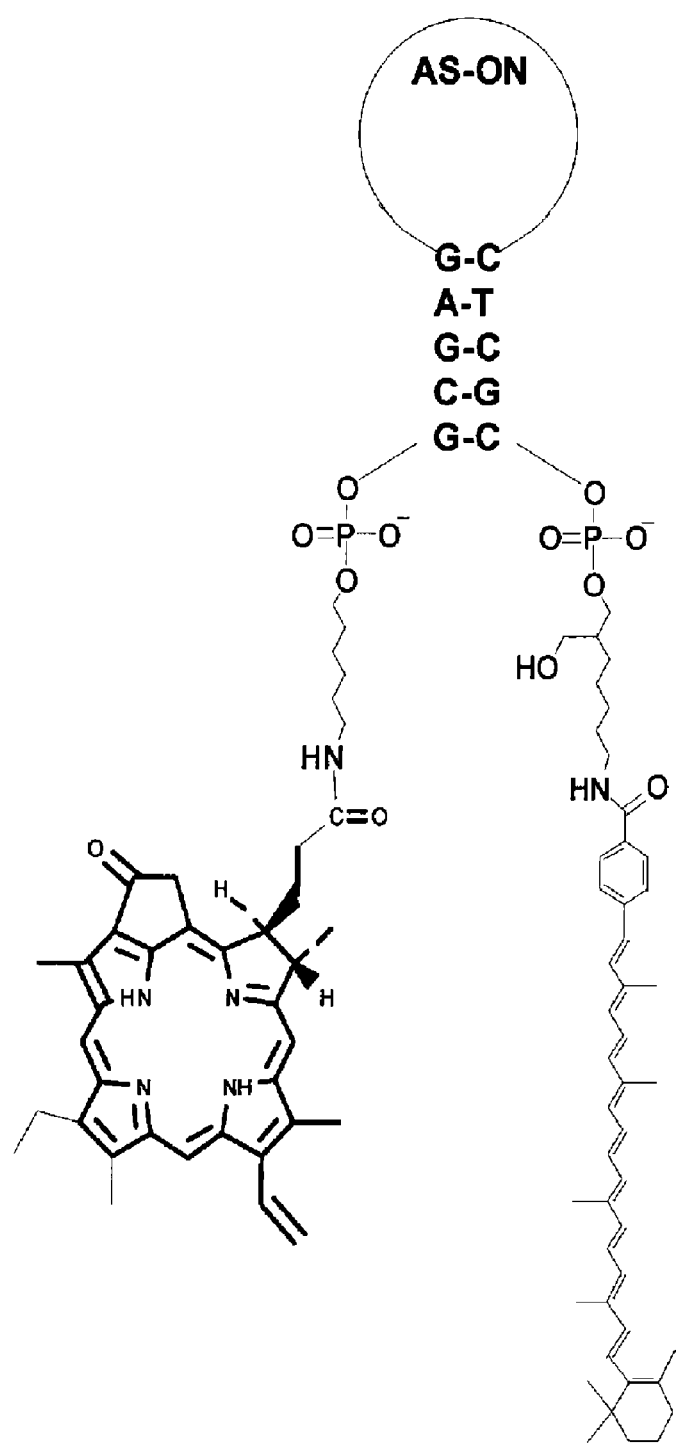

FIG. 14 depicts the structure of Pyro-30mer-Car.

Figure 15:
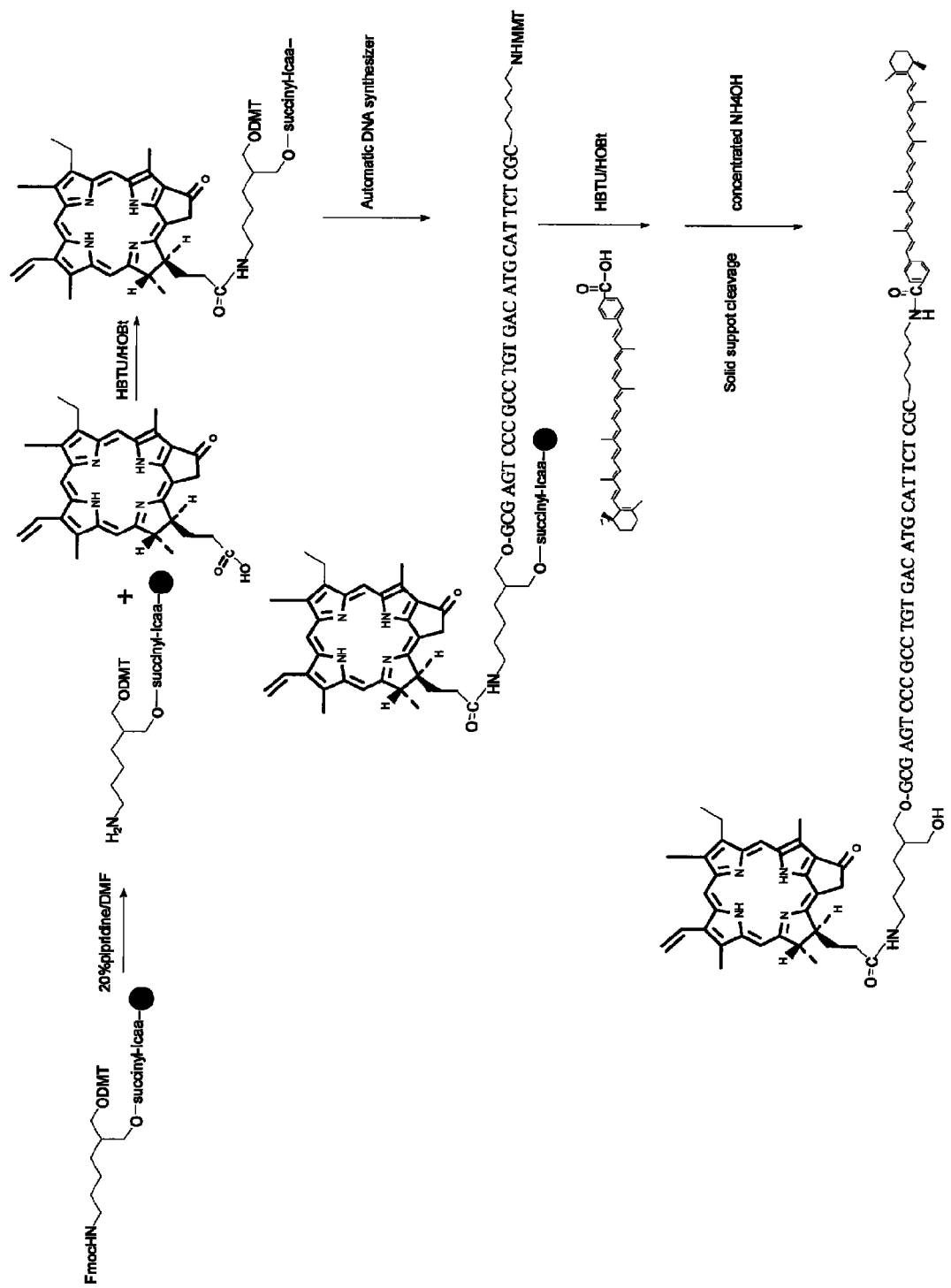

FIG. 15 depicts the synthesis of Pyro-30mer-Car.

Figure 16:
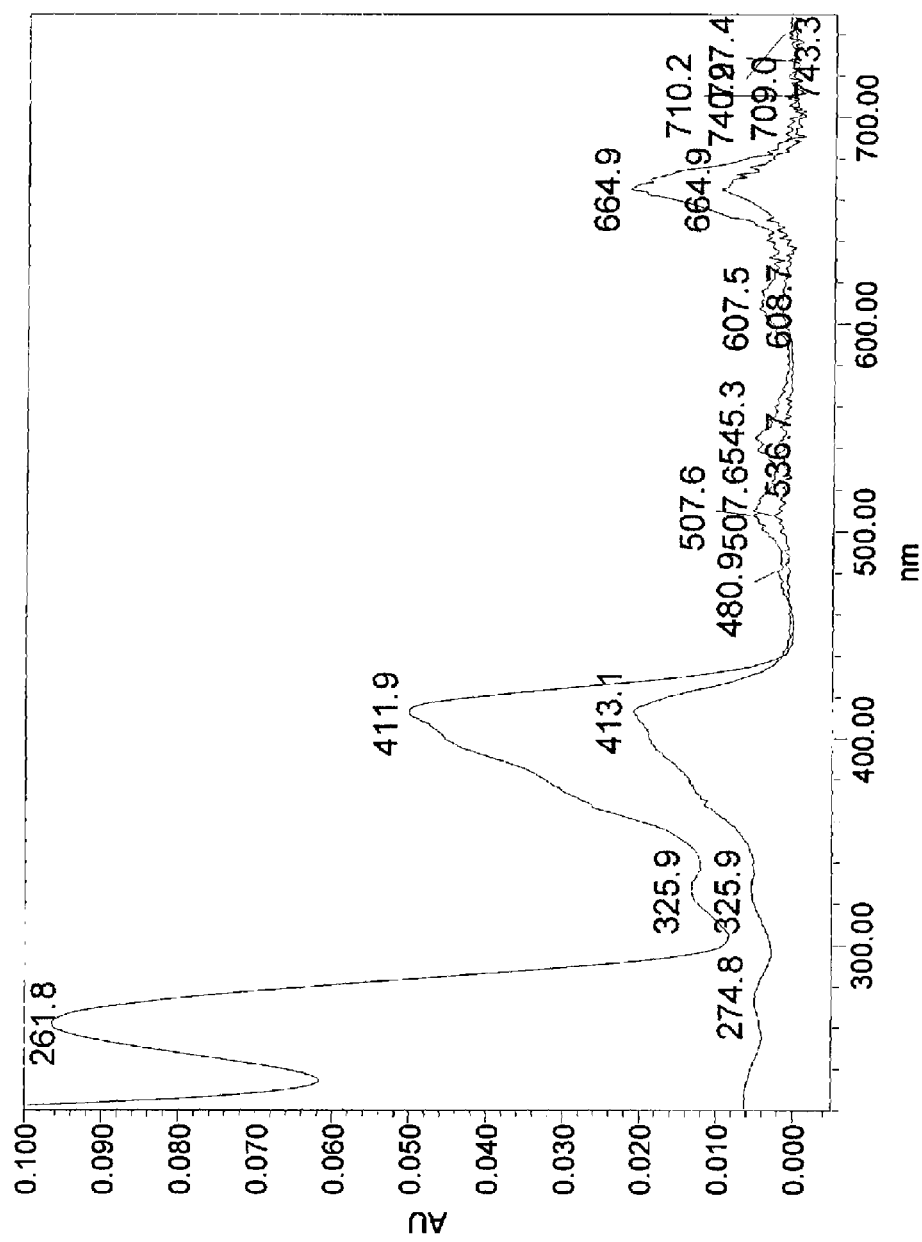

FIG. 16 depicts the absorption spectra of Pyro-30mer (red line) and Pyro acid (Green line).

Figure 17:
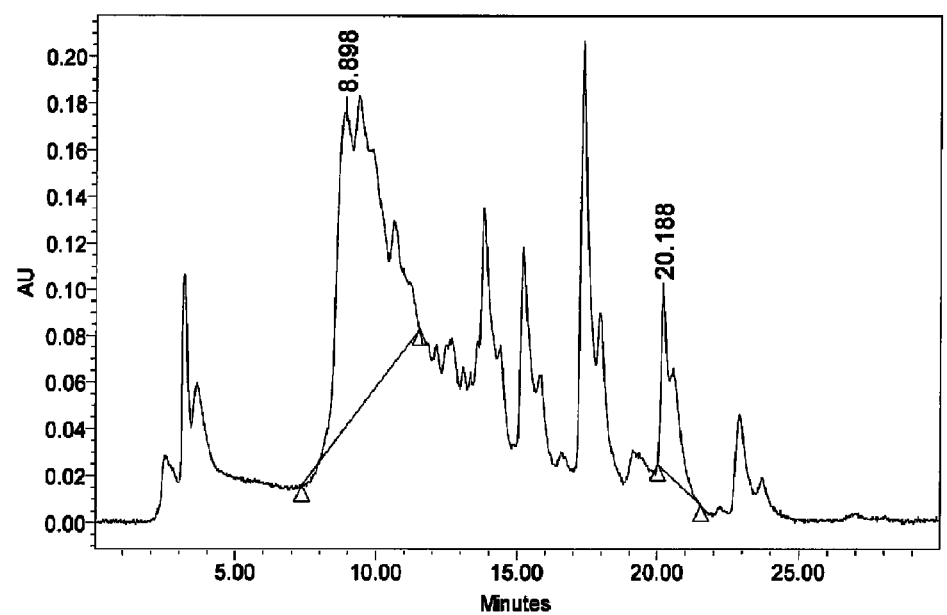
Figure 17:
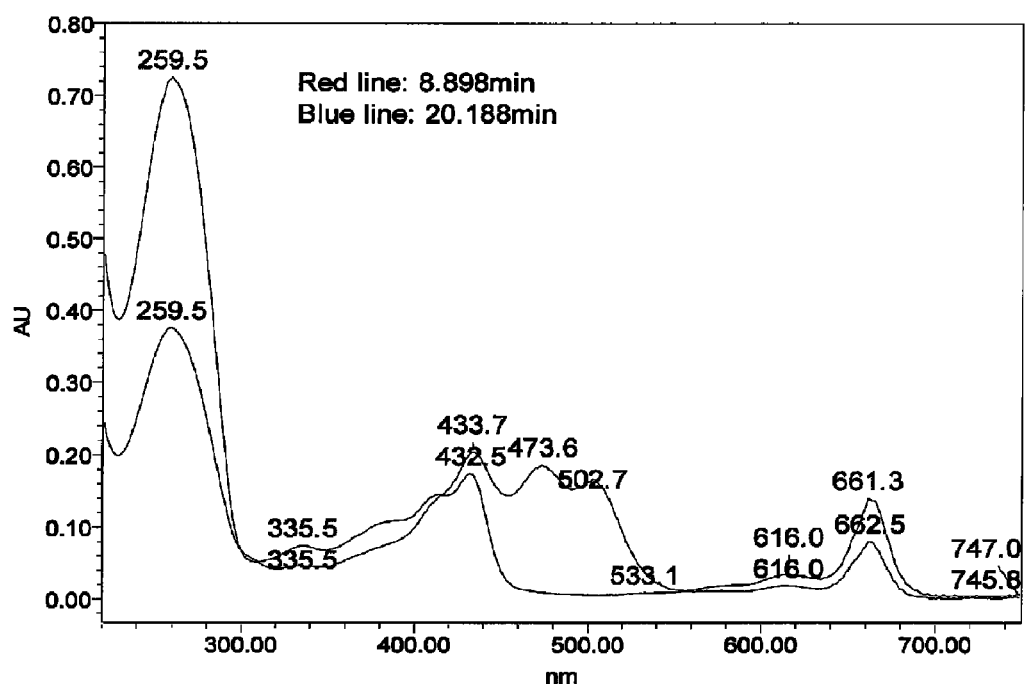

FIG. 17 depicts the HPLC result (top) and the absorption spectrum (bottom) of Pyro-30mer-Car(A) and Pyro-30mer (B).

Figure 18:
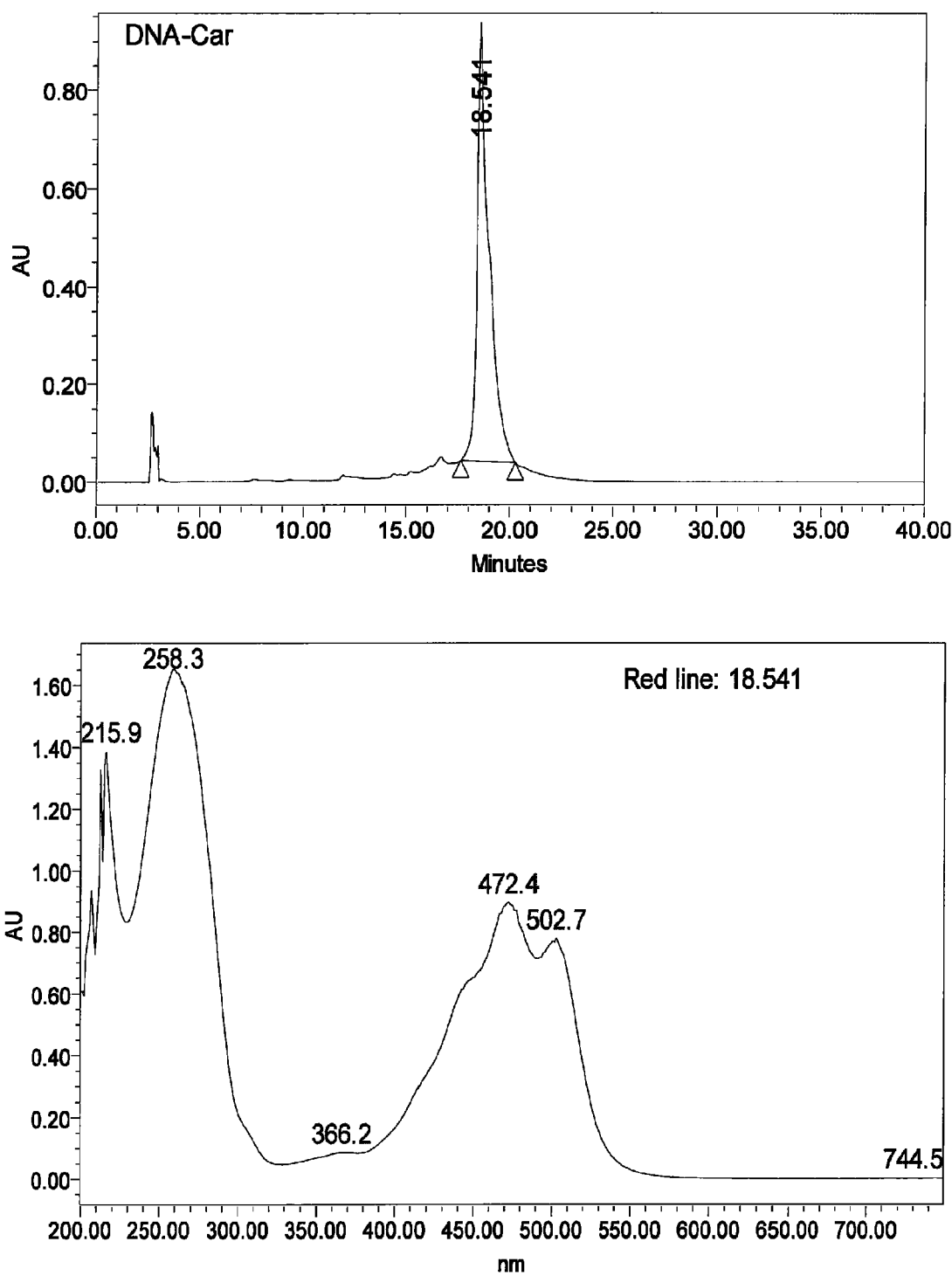

FIG. 18 depicts the HPLC retention time and absorption spectrum of $NH_2$-30 mer-Car.

Figure 19:
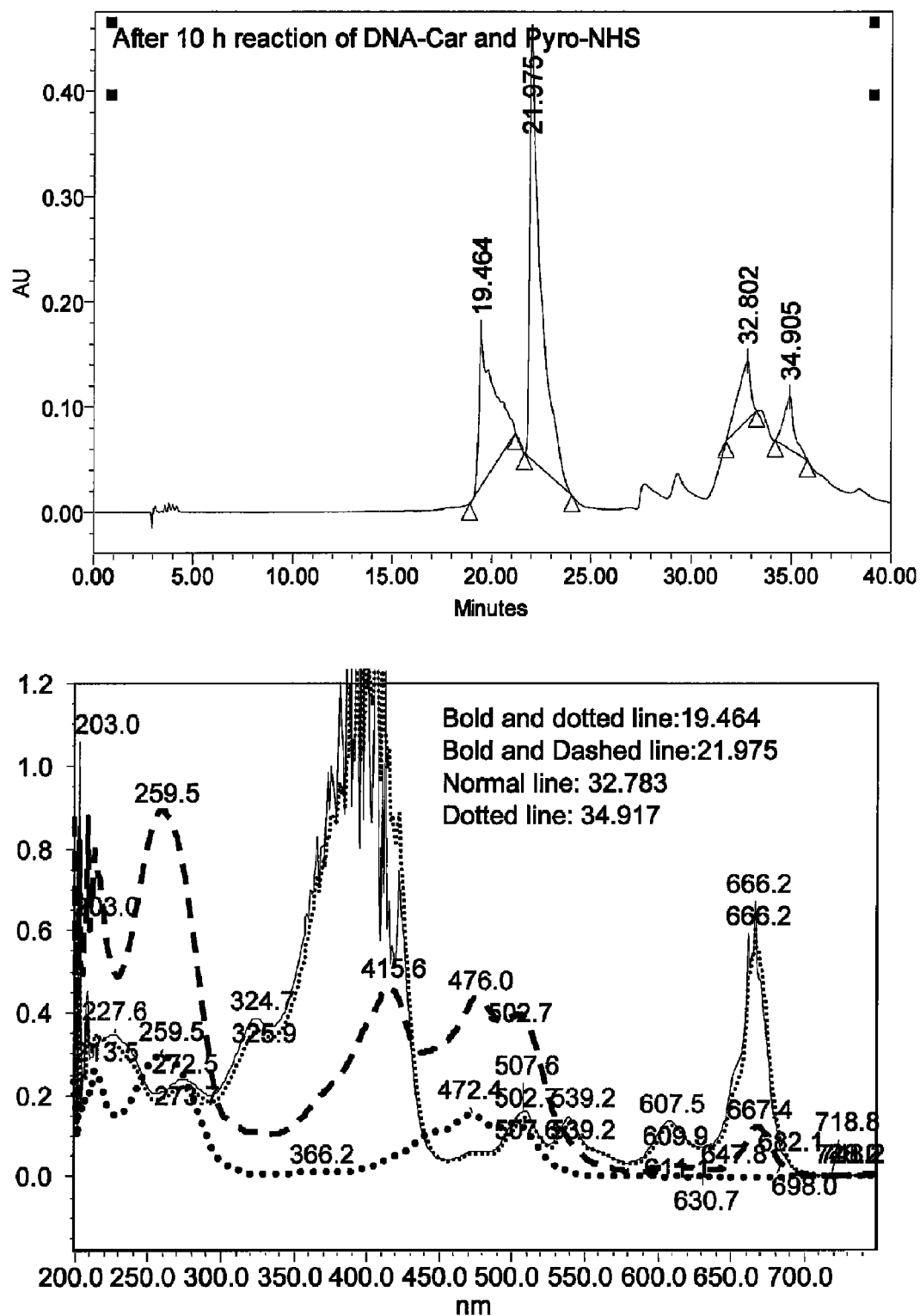

FIG. 19 depicts the HPLC result of the solution reaction (top) and the absorption spectrum of the peaks (bottom).

Figure 20:
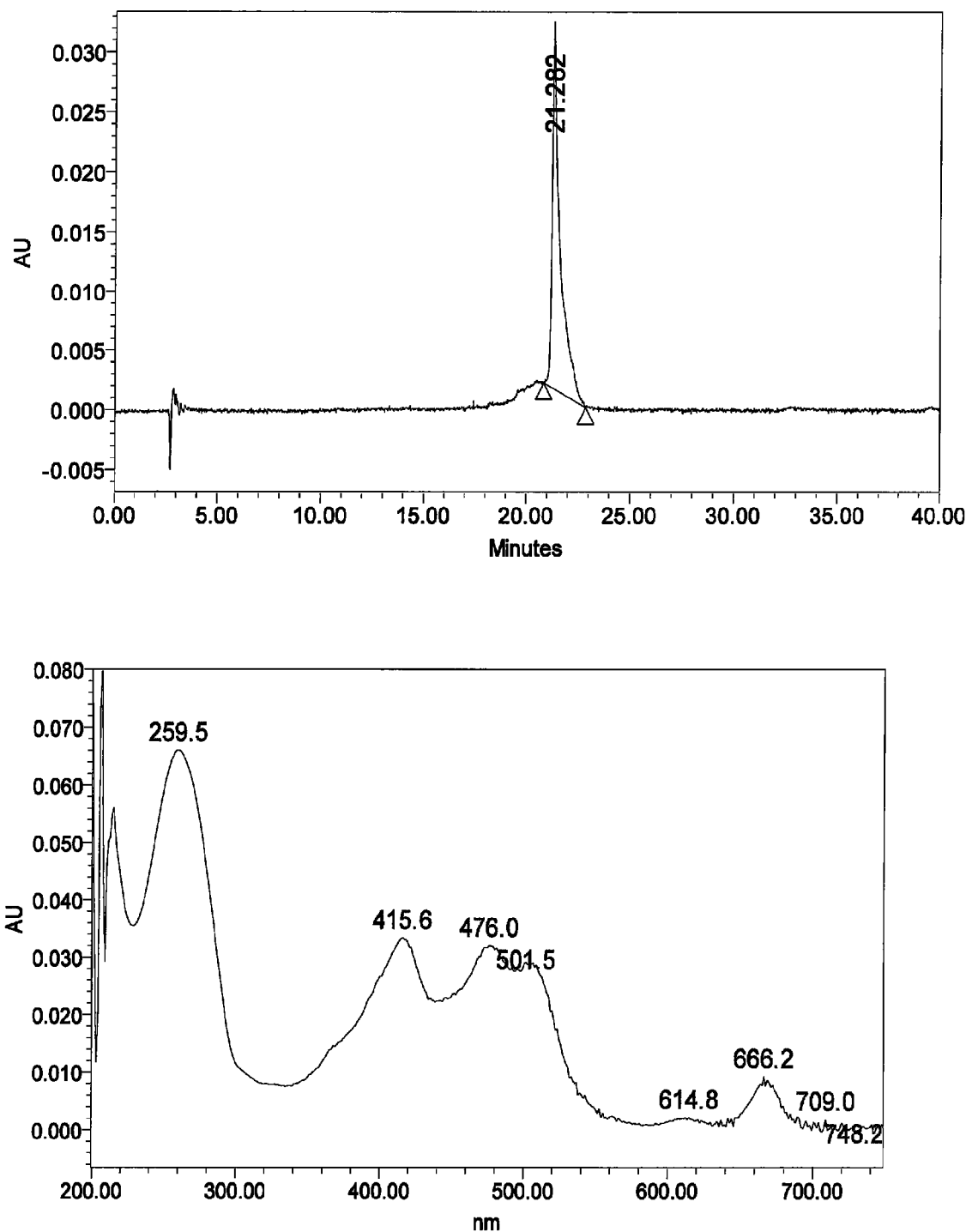
Figure 21:
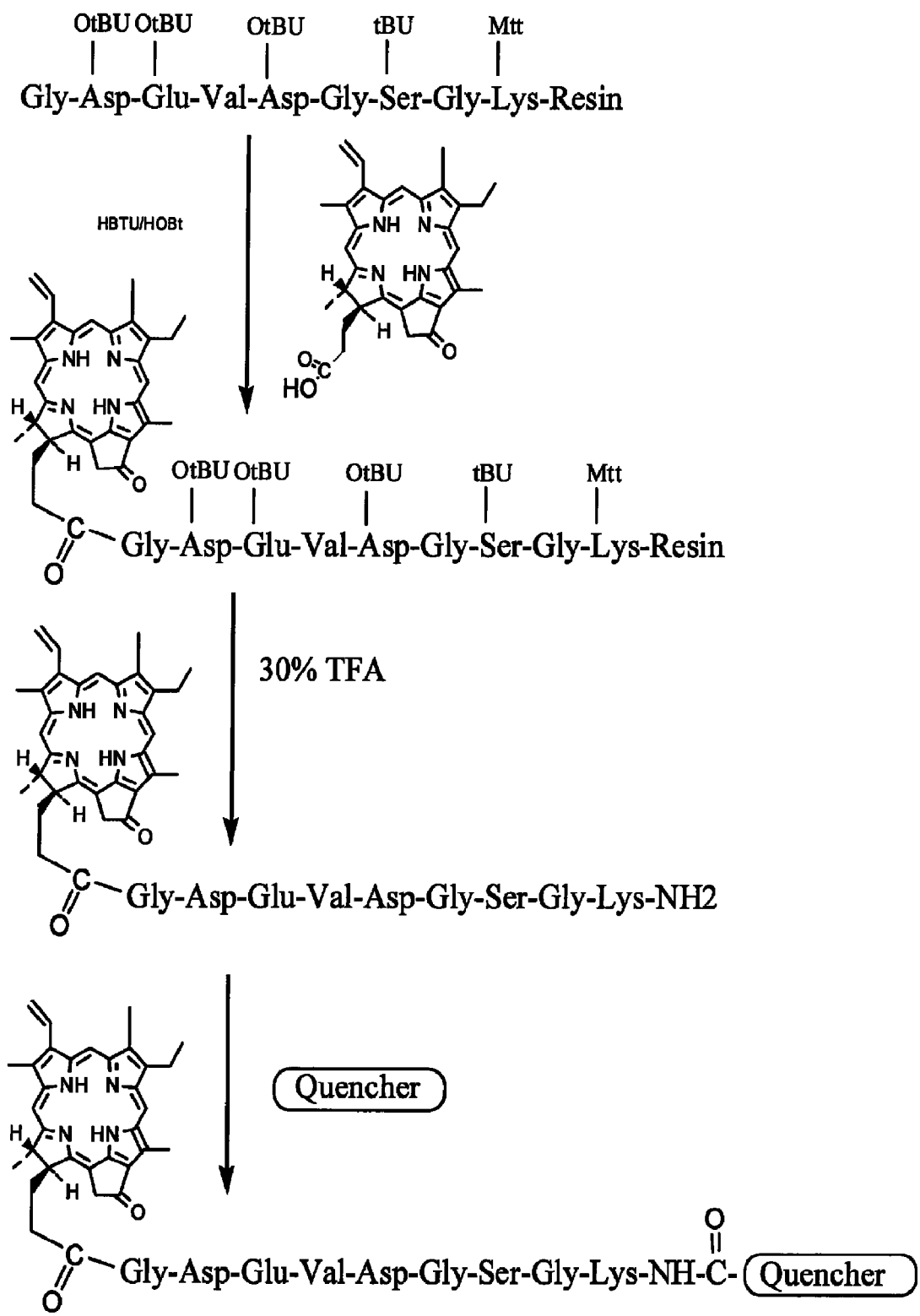

FIG. 20 depicts the HPLC retention time and absorption spectrum of Pyro-30mer-Car FIG. 21 The synthesis of Pyro-Peptide depicts the Car (PPC)

Figure 22:
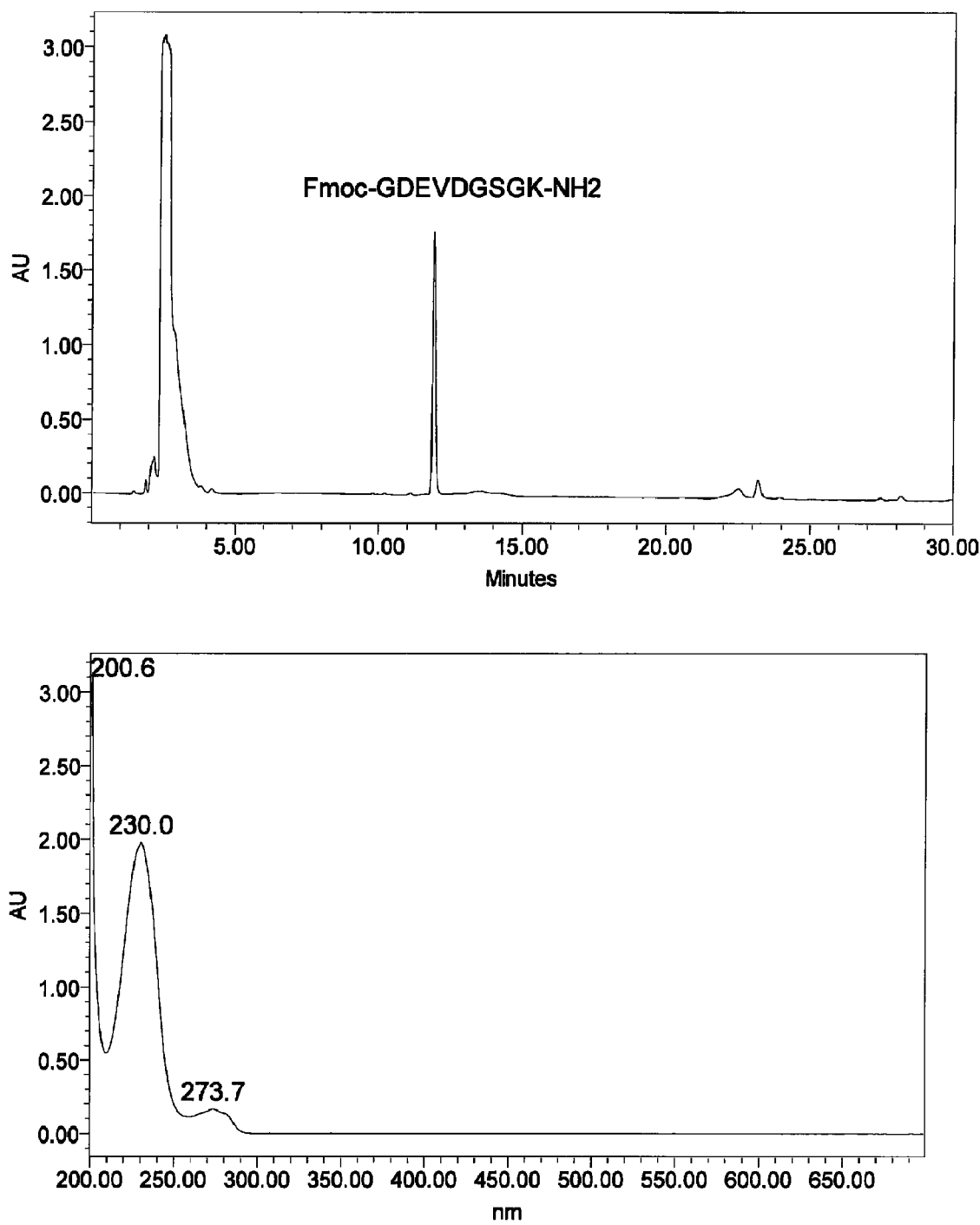

FIG. 22 depicts the HPLC retention time (top) and the UV-visible spectrum of the HPLC peak (bottom) of Fmoc-peptide-$NH_2$. (Using RP C18 100A column and 0.1% TFA and $CH_3CN$ as HPLC elution buffer, gradient from 90% 0.1% TFA buffer to 100% $CH_3CN$ in 45 min).

Figure 23:
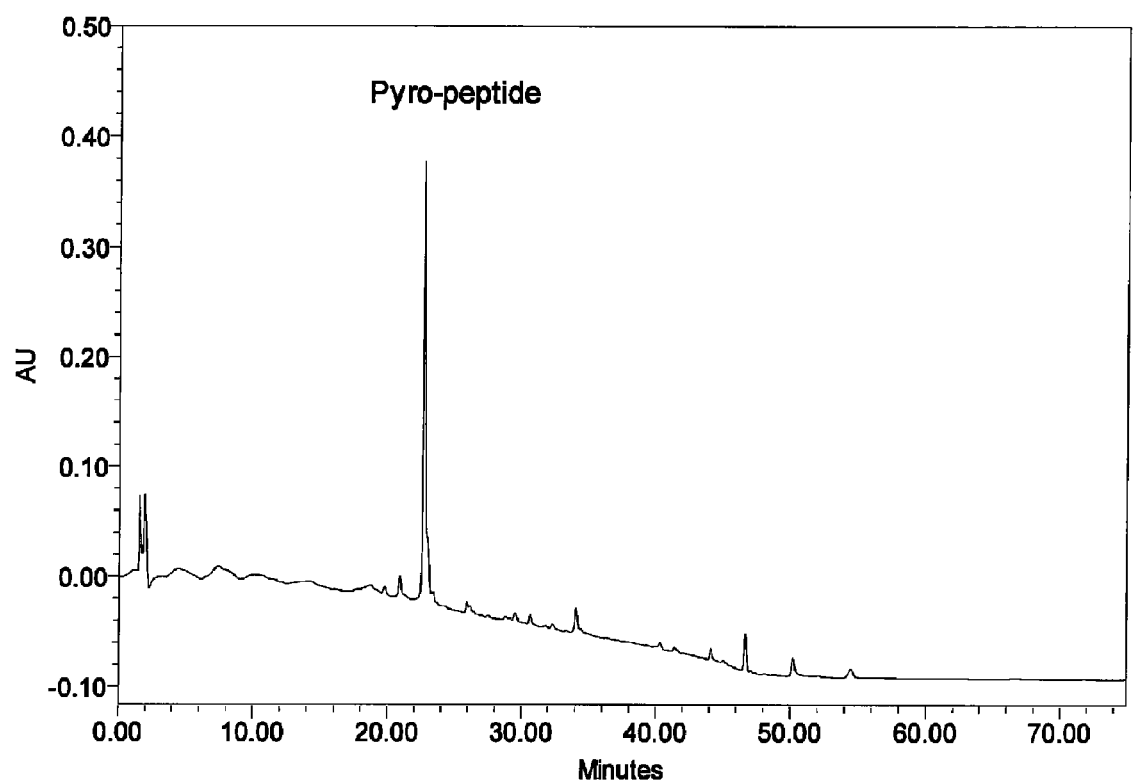
Figure 23:
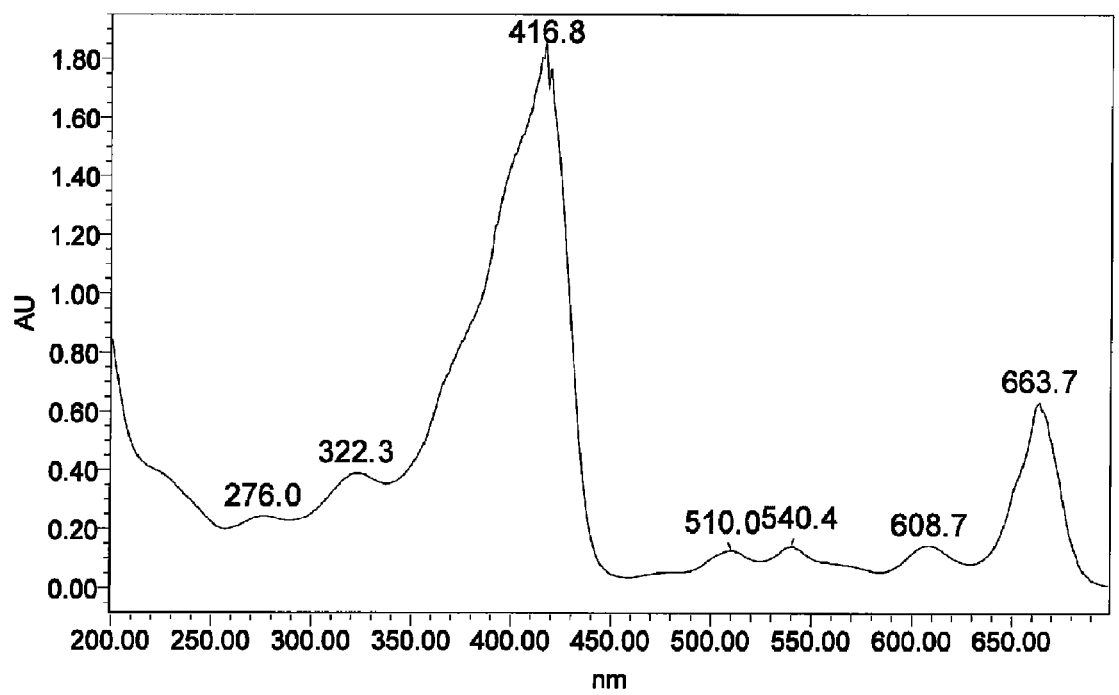

FIG. 23 depicts the HPLC retention time (left) and the UV-visible spectrum of the HPLC peak (right) of Pyro-peptide. (Using RP C18 100A column and 0.1% TFA and $CH_3CN$ as HPLC elution buffer, gradient from 90% 0.1% TFA buffer to 100% $CH_3CN$ in 45 min).

Figure 24:
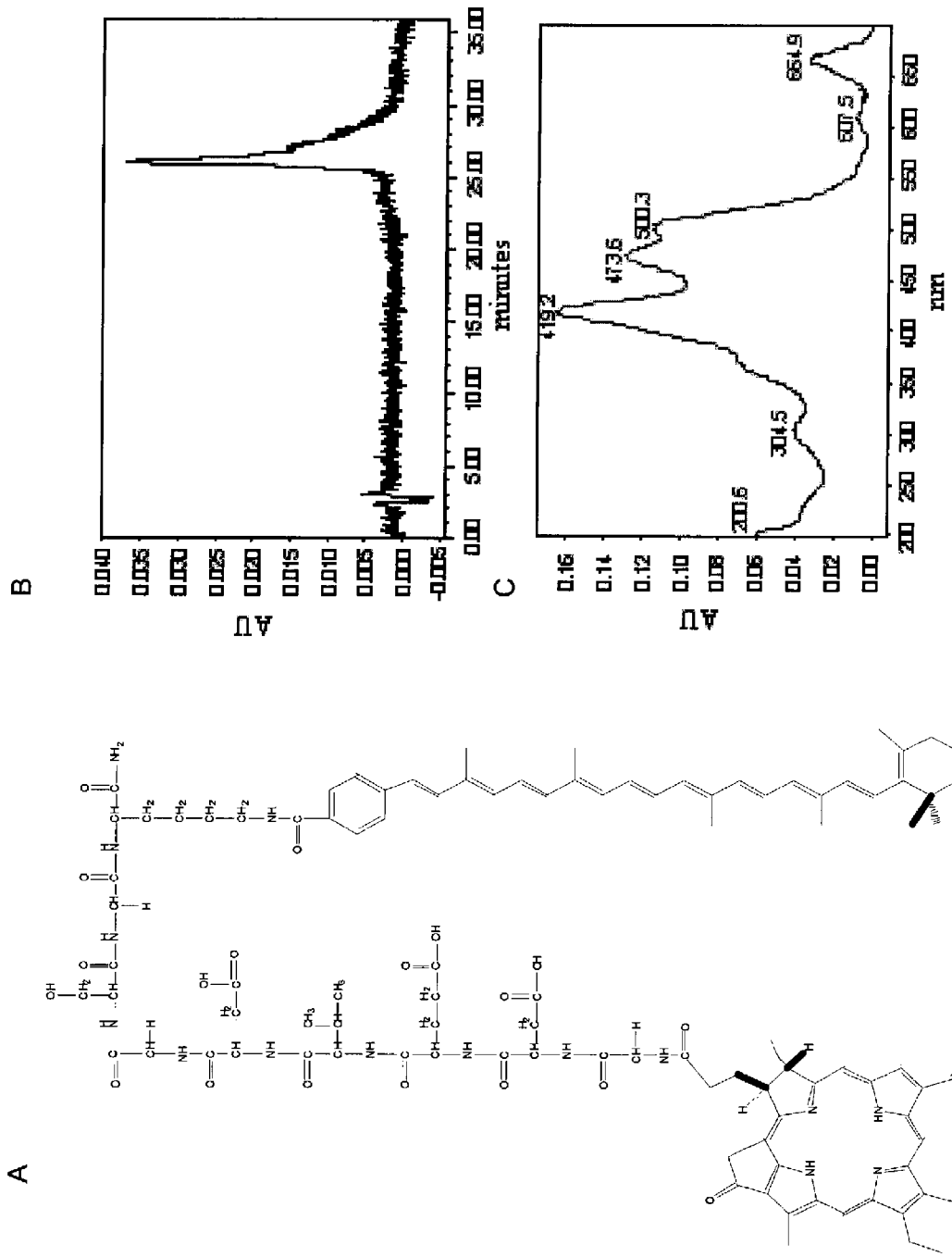

FIG. 24 depicts a A) structure of caspase-3 activatable Pyro-Peptide-Car; B) HPLC retention time of this construct; and C) corresponding optical absorption spectrum. HPLC method: column: RP C8 300A; solvent: 0.1% TFA, $CH_3CN$ and MeOH; gradient 60% (0.1% TFA) buffer and 40% $CH_3CN$ to 10% (0.1% TFA) buffer and 90% $CH_3CN$ in the first 20 min, then to 90% $CH_3CN$ and 10% MeOH for another 10 min, finally to 80% $CH_3CN$ and 20% MeOH for 10 min).

Figure 25:
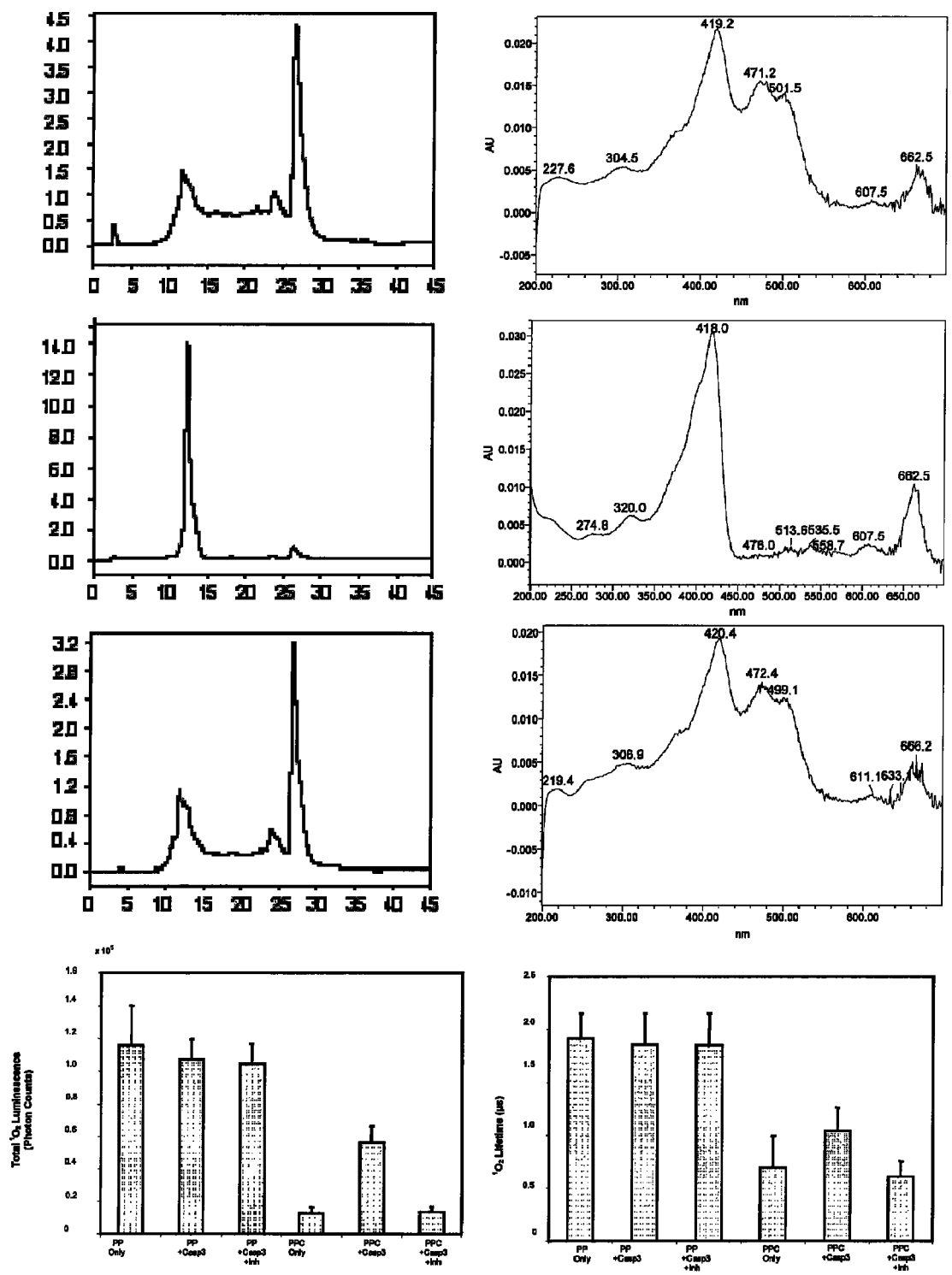

FIG. 25 depicts A) Fluorescence-based HPLC chromatograms (left column) and absorption spectra (right) corresponding to the dominant HPLC peaks for PPC alone (top), PPC+caspase-3 (middle) and PPC+caspase-3+inhibitor (bottom); B) total $^1O_2$ luminescence counts for PP, PP+caspase-3, PP+caspase-3+inhibitor, PPC, PPC+caspase-3, PPC+caspase-3+inhibitor; and C) corresponding $^1O_2$ lifetime.

Figure 26:
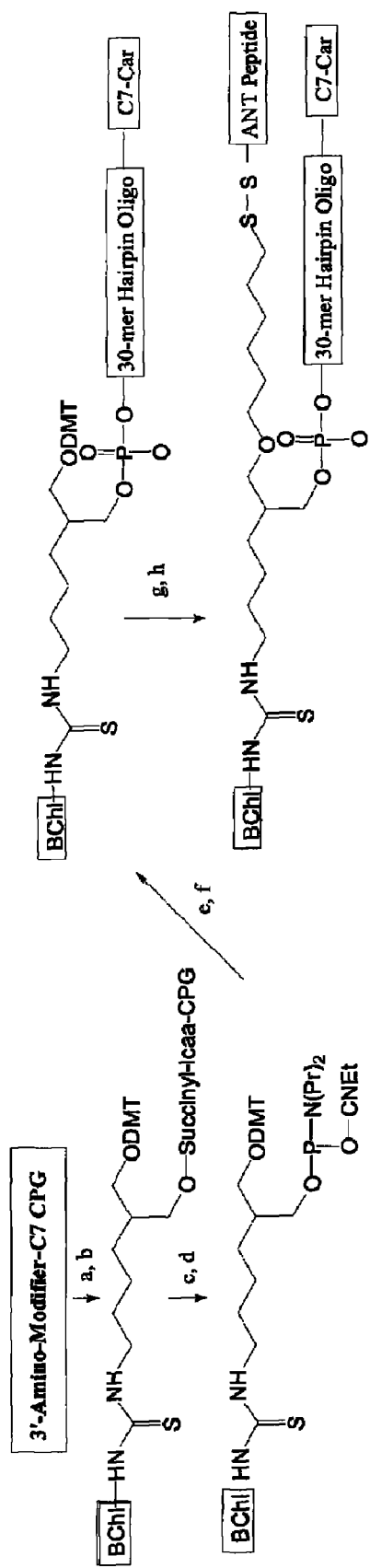

FIG. 26 depicts a) removing Fmoc; b) labeling BChl; c) cleaving CPG; d) formation phosphoramidite; e) synthesizing DNA from 3'-amino-modifier C7-CPG; f) labeling Car at 3' end; g) removing DMT; and h) linking ANT peptide via S—S bond.

Figure 27:
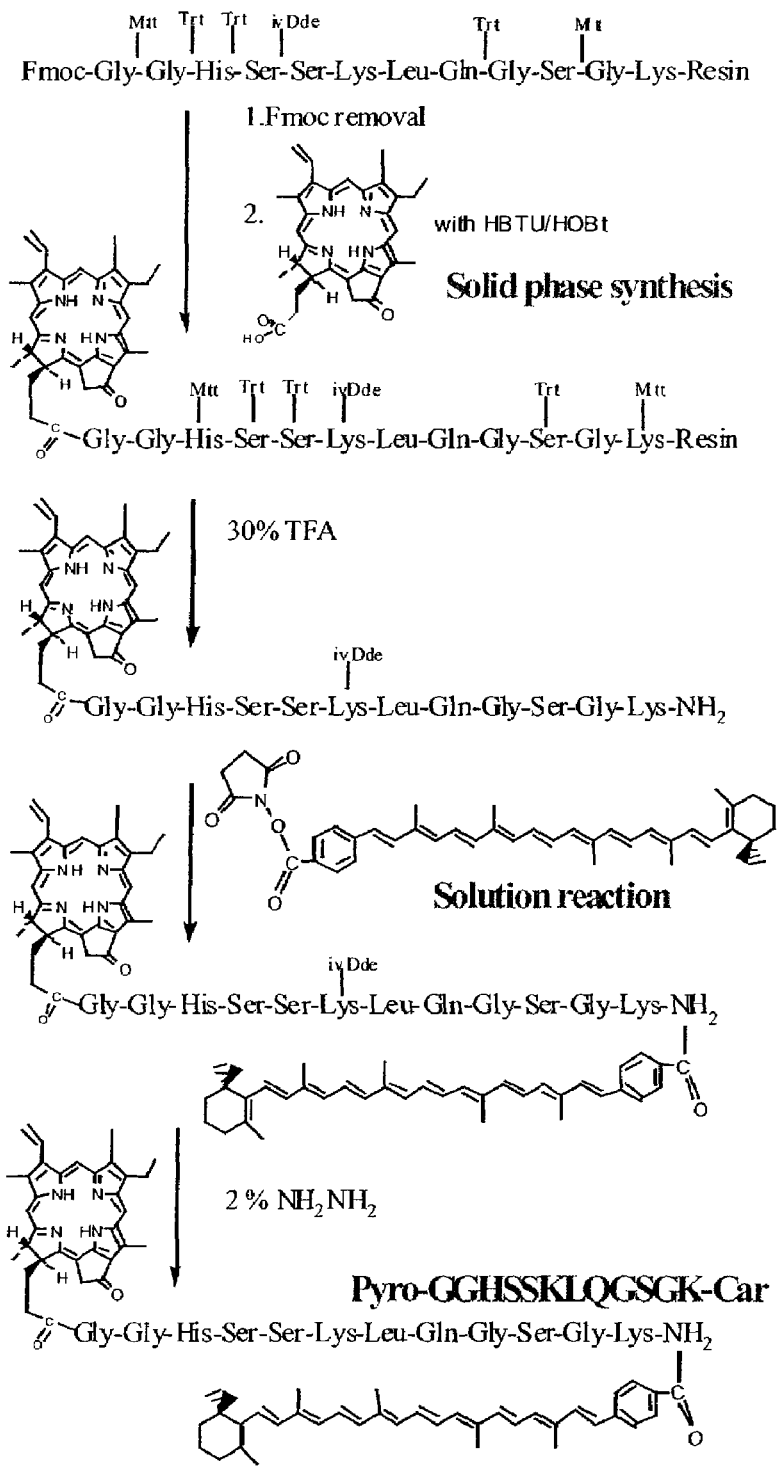

FIG. 27 depicts a synthesis of Pyro-GGHSSKLQGSGK (SEQ ID NO: 14)-CAR beacon.

Figure 28:
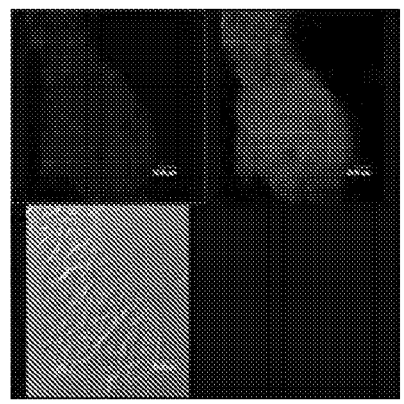
Figure 28:
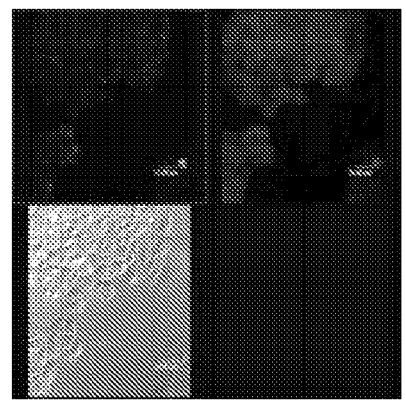
Figure 28:
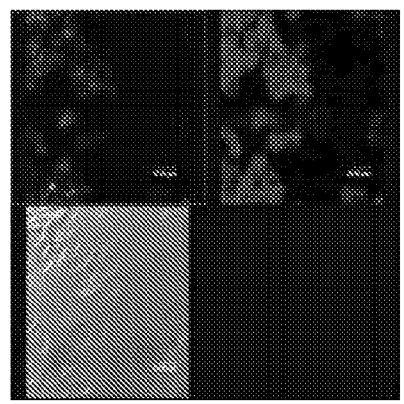
Figure 28:
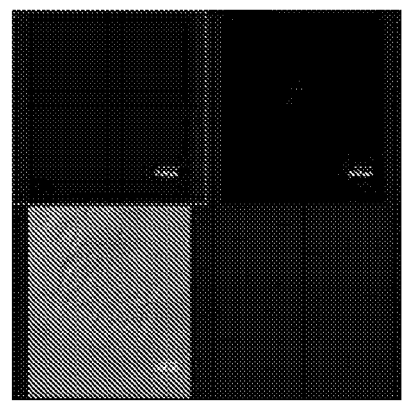

FIG. 28 depicts a intracellular uptake of PPF (a model beacon) in $HepG_2$ tumor cells. A) 200 µM PPF incubated with cells for 30 min; B) 200 µM PPF incubated with cells for 3 h; C) 200 µM PPF incubated with cells for 24 h; and D) cell alone control.

Figure 29:
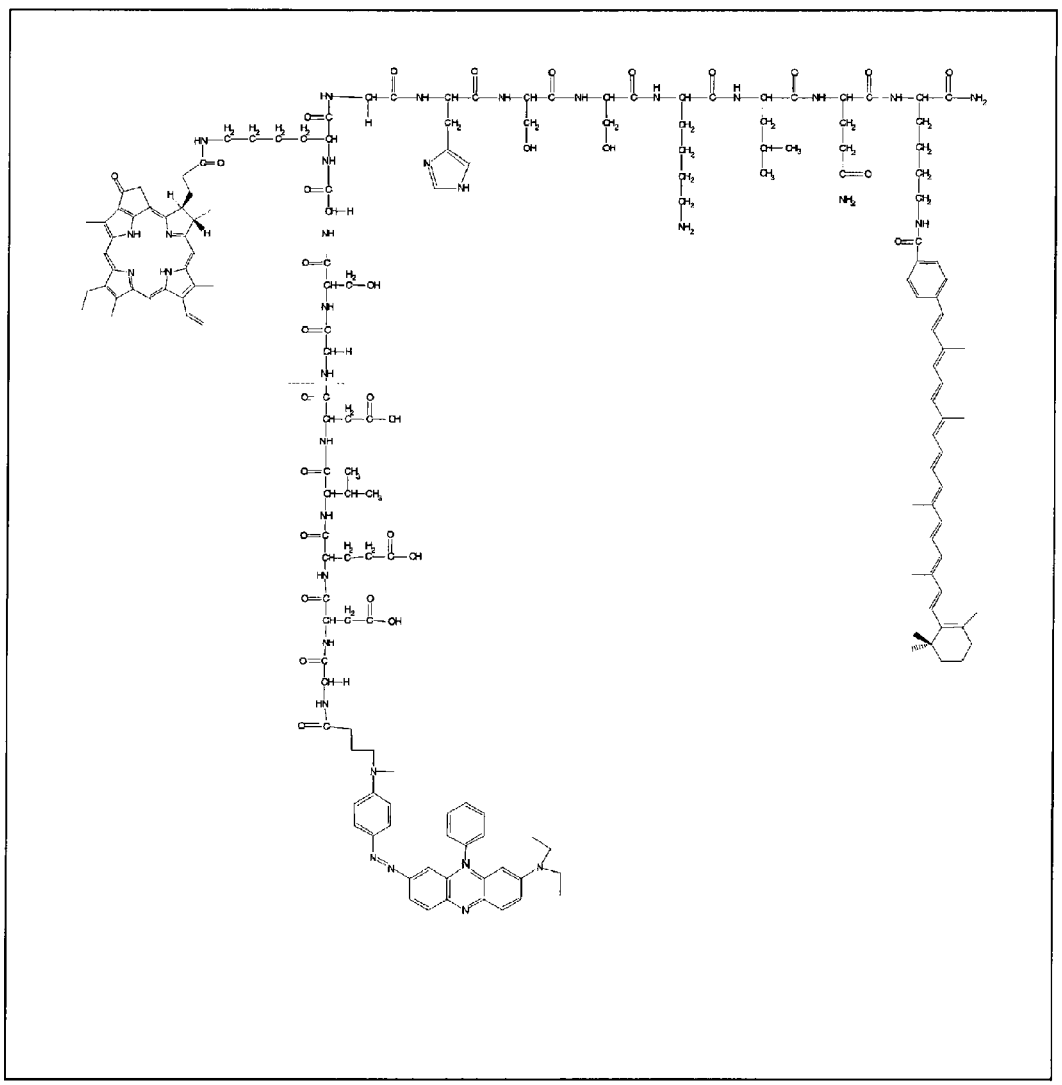

FIG. 29 depicts the structure of the first enzyme-activatable PDT agent with a built in death sensor, BHQ-GDEVDGSGK (Pyro)HSSKLQK-Car.

Figure 30:
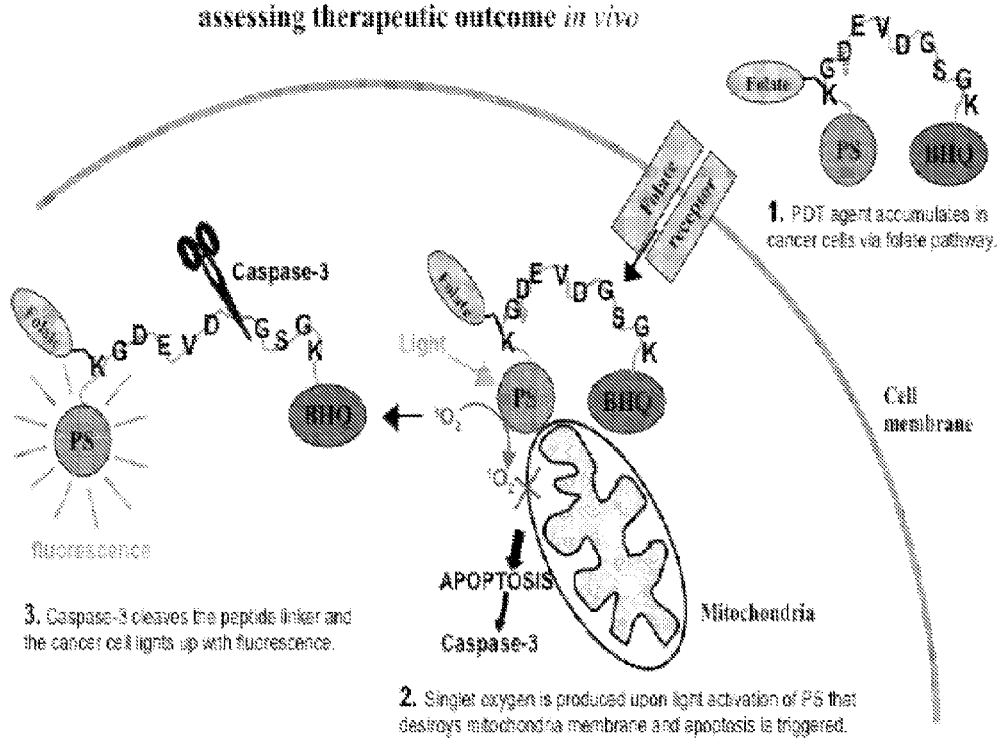

FIG. 30 depicts a conjugate which is an activatable PDT agent of the present invention, and an apoptosis reporter. "PS" is the photoactivatable killing agent which generates reactive oxygen species (ROS), such as singlet oxygen ($^1O_2$) or superoxide free radicals; and "BHQ" is the quencher which quenches the fluorescence of the photoactivatable killing agent when the photoactivatable killing agent and quencher are in close proximity "Folate" is the targeting ligand.

Figure 31:
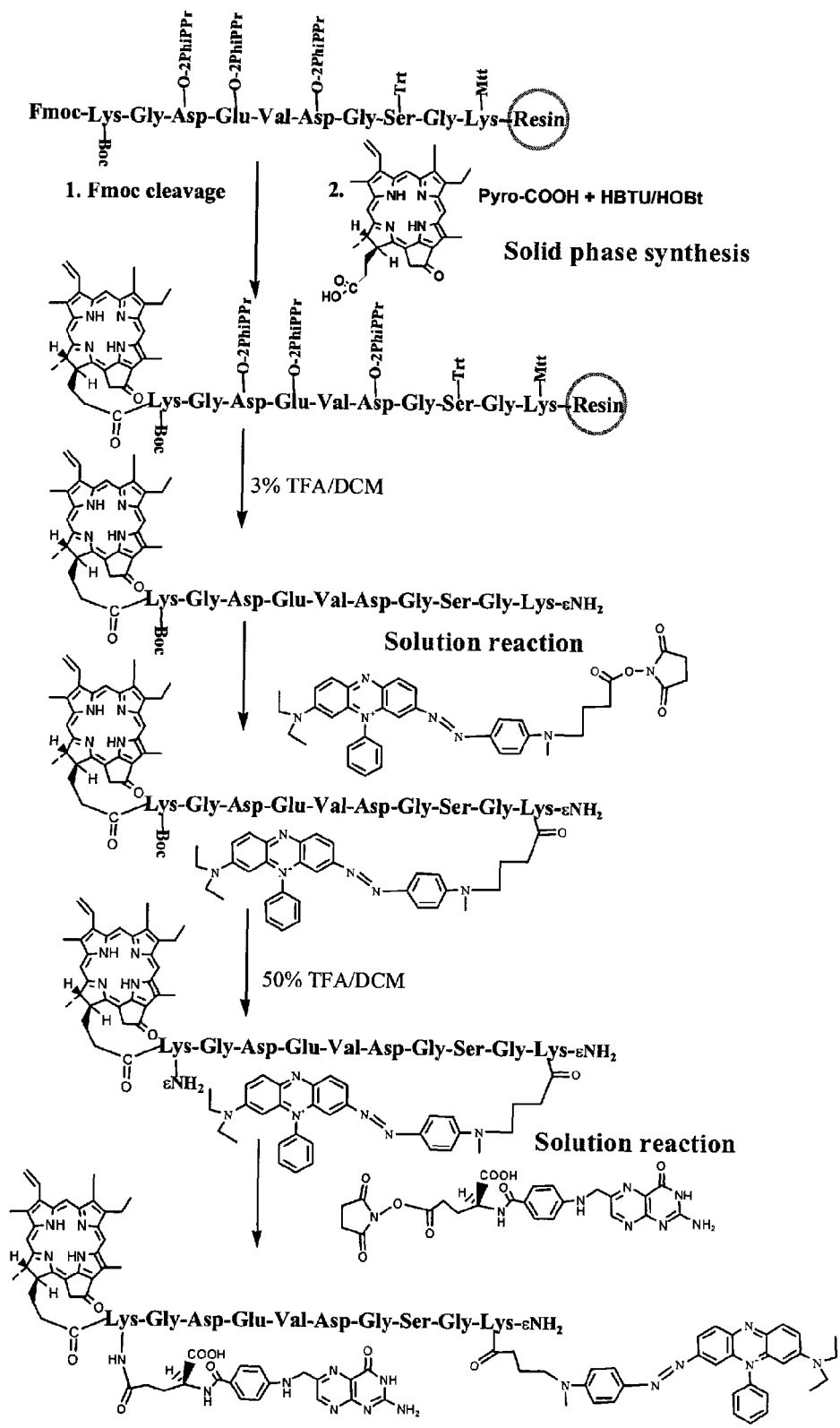

FIG. 31 depicts a synthesis of Pyro-K(folate)Peptide-BHQ

Figure 32:
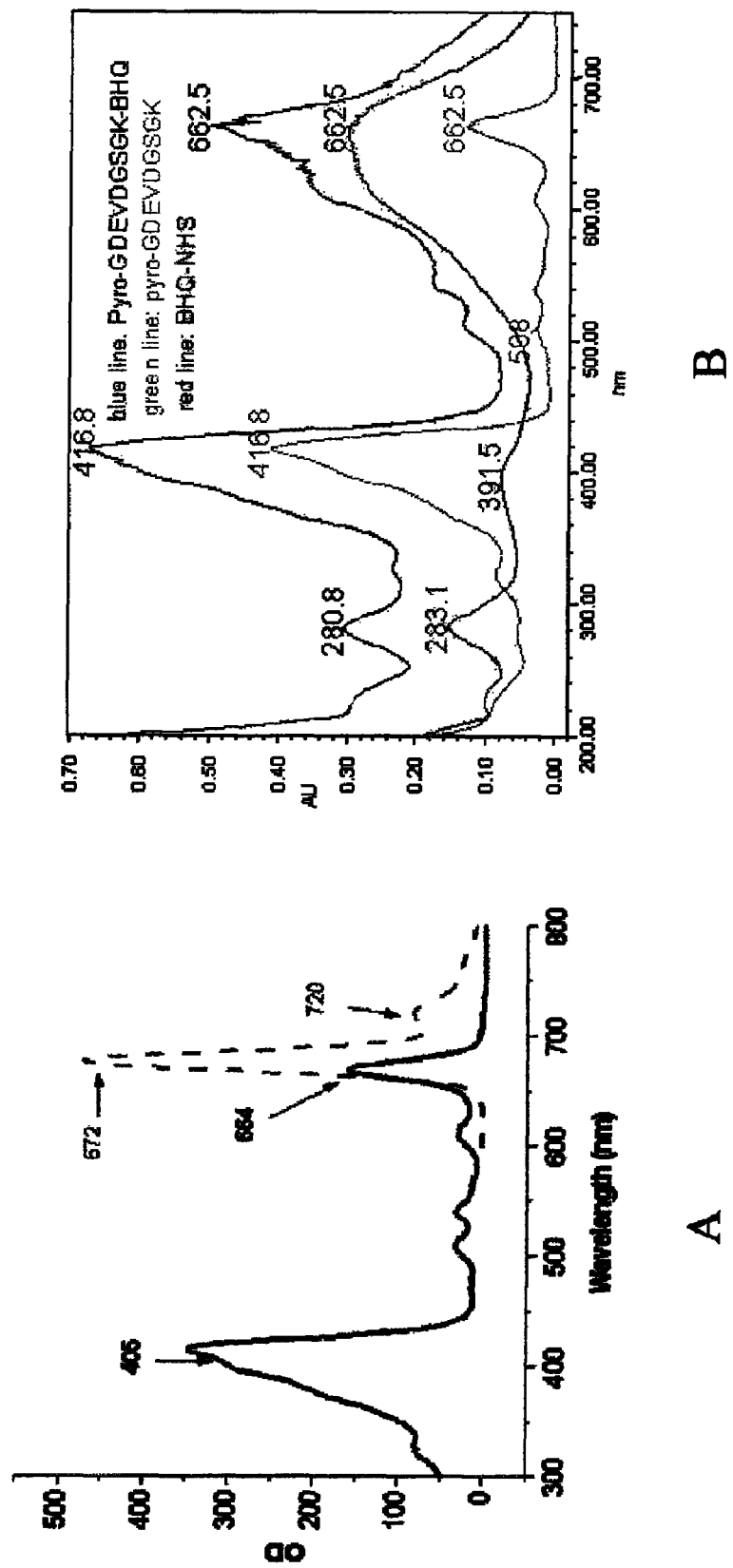

FIG. 32 depicts absorption and emission spectra of Pyro (a) and Pyro-peptide-BHQ, Pyro-peptide and BHQ-NHS.

Figure 33:
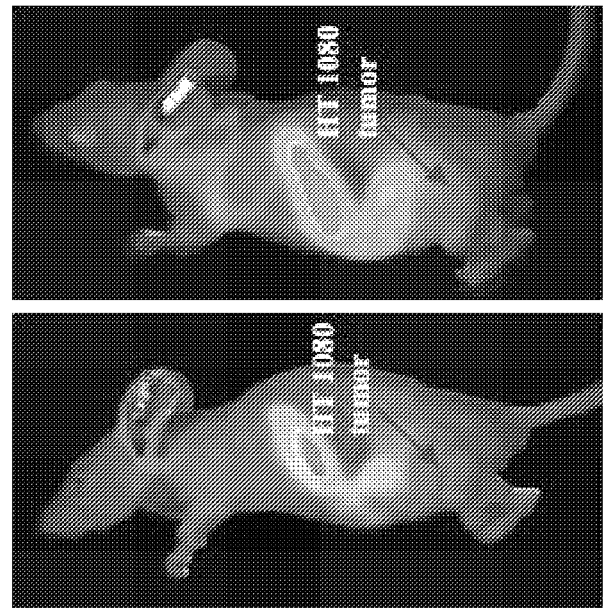
Figure 33:
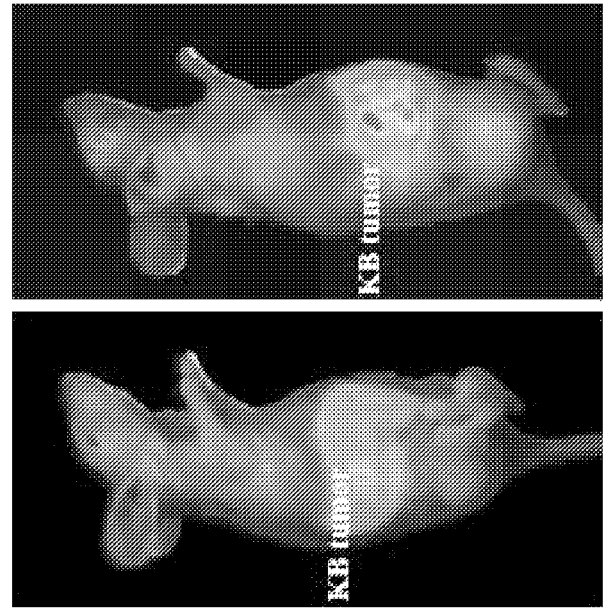

FIG. 33 depicts folate receptor positive and negative mice treated with targeted PDT agent with built-in apoptosis reporter. Mouse #1: KB tumor (folate receptor positive); Mouse #2: HT 1080 tumor (folate receptor negative); A: 2.5 h post IV injection, before PDT; B: 5 h post IV injection, 2 h after PDT.

Figure 34:
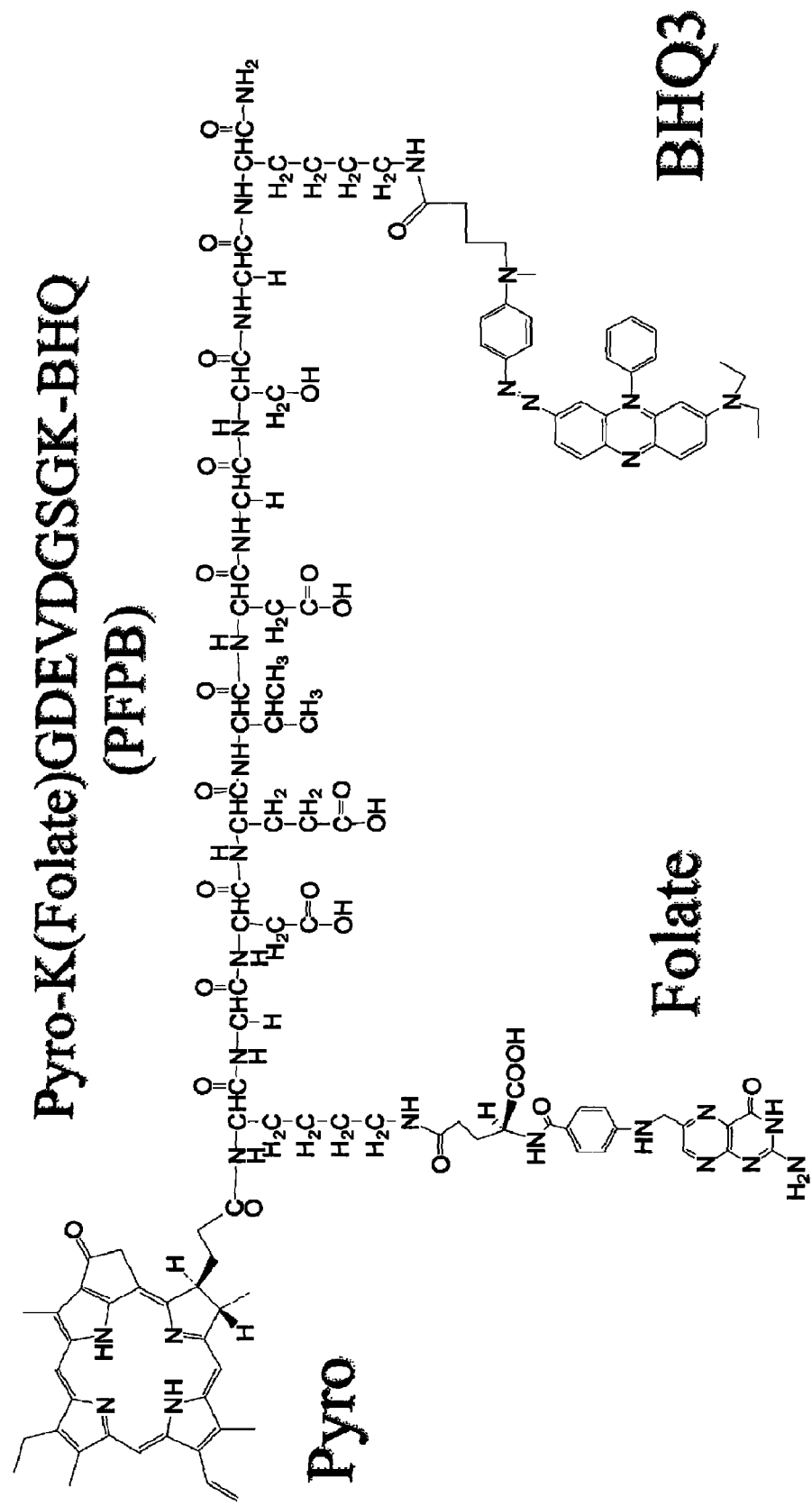

FIG. 34 depicts the structure of folate coupled to the e-$NH_2$ of N-terminal Lys of Pyro-KGDEVDGSGK(SEQ ID NO: 11)-BHQ.

Figure 35A:
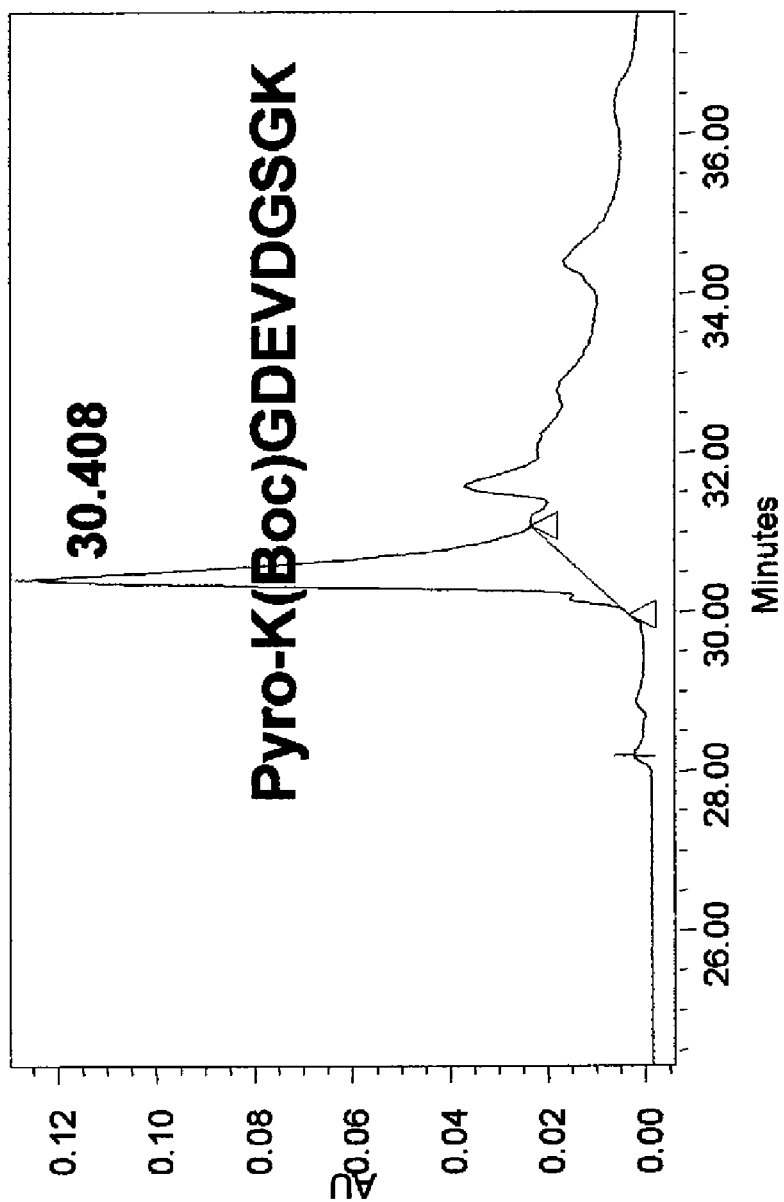

FIG. 35A depicts the HPLC retention time of Pyro-K(Boc) GDEVDGSGK(SEQ ID NO: 11).

Figure 35B:
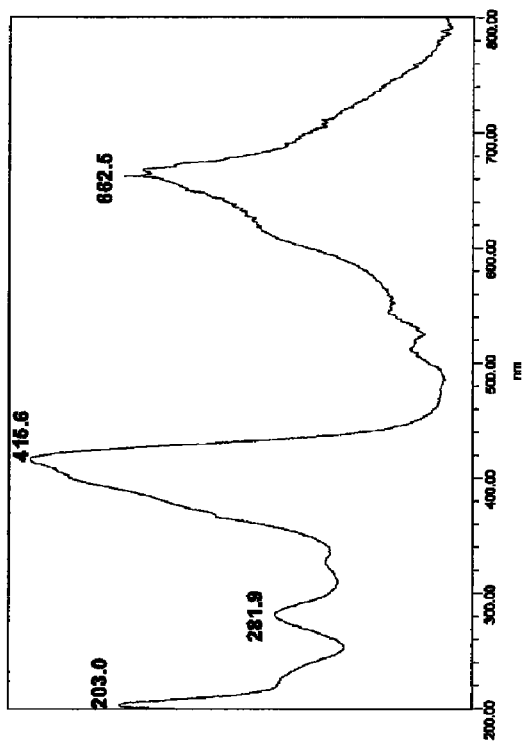
Figure 35B:
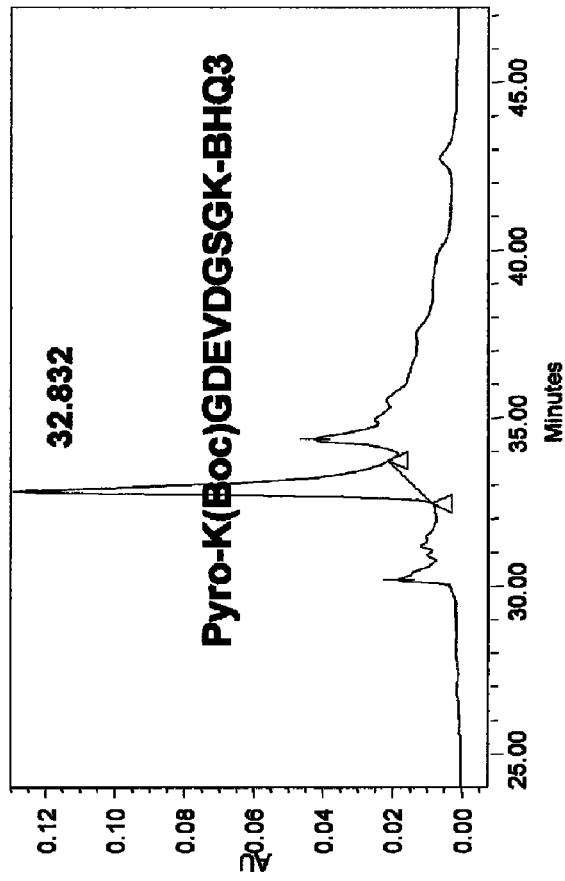

FIG. 35B depicts the HPLC retention time and the UV-visible spectrum of the HPLC peak (the right) of Pyro-K (Boc)GDEVDGSGK-BHQ3.

Figure 35C:
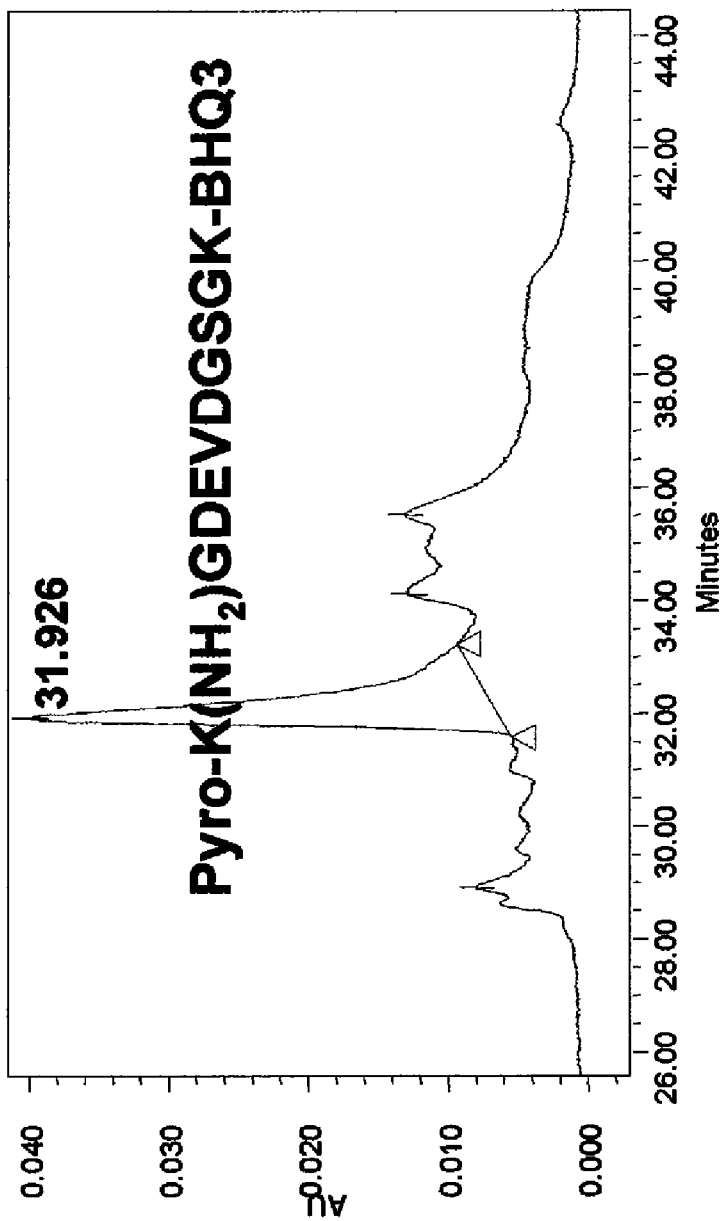

FIG. 35C depicts the HPLC retention time of Pyro-K (NH2)GDEVDGSGK(SEQ ID NO: 11)-BHQ3.

Figure 35D:
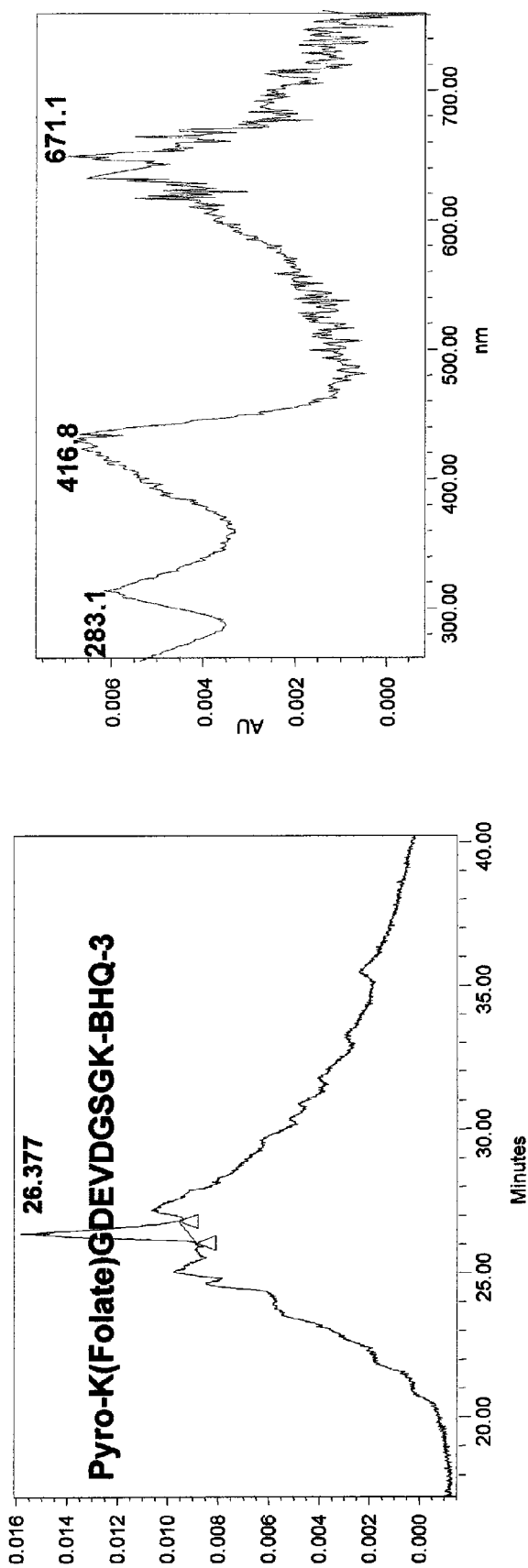

FIG. 35D depicts the HPLC retention time and the UV-visible spectrum of the HPLC peak (the right) Pyro-K(Folate) GDEVDGSGK(SEQ ID NO: 11)-BHQ-3.

DETAILED DESCRIPTION OF THE INVENTION

Terms are used herein as generally used in the art, unless otherwise defined.

Conjugates

In one aspect, the present invention provides conjugates comprising at least one substrate. In an embodiment of the present invention, the substrates of the present invention have following characteristics: 1) they contain a substrate; 2) they contain a photoactivatable killing agent (P) and a first quencher (Q) attached to the substrate, wherein P and Q are held in proximity by the appropriate length of the substrate sequence. In one embodiment the first quencher is a triplet state quencher. Thus, Q quenches the triplet state of P and the subsequent formation of ROS is eliminated, therefore, PDT treatment will not harm the target cells and viruses. The substrate is capable of changing conformation, and Q is removed from the immediate vicinity of P. Upon PDT treatment, P generates ROS to kill the target cells or viruses.

In certain embodiments, the change of conformation of the substrate is caused by cleavage of the substrate. Accordingly, in certain embodiments the substrates of the conjugates of the present invention will be cleaved in the presence of specific enzymes. The specific enzymes will preferably be over-expressed, or present only, in diseased, e.g., virally infected, cancerous, and/or inflamed, tissue as compared to healthy tissues. Thus, upon exposure to light, the photoactivatable killing agent-containing cleavage products generate reactive oxygen species which preferentially destroy the diseased tissue. Because the photoactivatable killing agent is preferentially activated in target cells, damaged induced by the photoactivatable killing agent will be highly specific. Accordingly, substrates may be those that are cleavable by one or more cleavage enzymes.

In another aspect, the present invention provides conjugates comprising at least one cell death protease recognition sequence. In an embodiment of the present invention, the cell death protease recognition sequences of the present invention have the following characteristics: 1) they contain a cell death protease recognition sequence; 2) they contain a photoactivatable killing agent (P) comprising a fluorophore and a fluorescence quencher (Q), wherein P and Q are held in proximity by the appropriate length of the cell death protease recognition sequence; and 3) a targeting ligand. Thus, Q quenches the fluorescence of P but not the ability of P to produce singlet oxygen. Upon PDT treatment, P generates ROS to kill the target cells. The cell death protease recognition sequence is capable of changing conformation, including being cleaved, and Q is removed from the immediate vicinity of P thus allowing fluorescence of P. The resultant fluorescence of P allows for monitoring of apoptosis. Thus, the invention provides for a targeted photodynamic therapy agent with a built in apoptosis sensor.

In one embodiment, the change of conformation of the cell death protease recognition sequence is caused by cleavage of the cell death protease recognition sequence. Accordingly, In one embodiment, the cell death protease recognition sequences of the conjugates of the present invention will be cleaved in the presence of specific enzymes. Cell death protease recognition sequences may be those that are cleavable by one or more cleavage enzymes.

As stated above, in certain aspects the conjugates of the present invention comprise at least one substrate, one photoactivatable killing agent and one quencher. In general, the substrates of the present invention serve as a scaffold. In particular, when the substrate is intact, the quencher and the photoactivatable killing agent are held in proximity such that the quencher quenches the triplet state of the photoactivatable killing agent. Once the substrate is undergoes a conformation change, the quencher and the photoactivatable killing agent are no longer held in proximity and the photoactivatable killing agent is no longer quenched. Suitable substrates include polypeptides, nucleic acid molecules, synthetic polymers, phospholipids, galactose-containing compounds, or combinations thereof. In one embodiment the photoactivatable killing agent and first quencher are attached to the substrate by a linker molecule.

In one embodiment, the substrate is a polypeptide which contains a site which is cleavable by a proteinase. As used herein, "proteinase" and "protease" are synonyms and refer to any enzyme that breaks down proteins by cleavage at one or more specific peptide bonds. The substrates of the present invention may comprise one or more sites cleavable by a viral protease and/or an protease which is over-expressed, over-abundant or present only in diseased tissue.

Generally, proteolytic enzymes cleave at specific amino acid residues. Therefore, in one embodiment the conjugates of the present invention comprise substrates which contain specific residues that are recognized by viral proteases or proteases which are specific to, over-expressed in, or over-abundant in infected tissue. Suitable enzymes include proteases, such as, viral proteases and retroviral proteases.

In an embodiment, the present invention provides substrates with the following structures: X-Tyr-Pro-Y, X-Lys-Lys-Y, X-Arg-Arg-Y, X-Gly-Ile-Y, X-Gly-Leu-Y, X-Ala-Ser-Y, X-Asp-Gly-Y, X-Phe-Phe-Y, X-Asp-Glu-Val-Asp (SEQ ID NO:74-)-Y, X-Gly-Pro-Arg-Y, X-Arg-Gly-Y, or X-His-Ser-Ser-Lys-Leu-Gln(SEQ ID NO:13)-Y, wherein X and Y are each independently a polypeptide comprising from one to about 15 amino acids.

Cell Death Protease Recognition Sequences

As stated above, in certain aspects the conjugates of the present invention comprise a cell death protease recognition sequence, a photoactivatable killing agent comprising a fluorophore, a fluorescence quencher, and a targeting ligand. In general, the cell death protease recognition sequences of the present invention serve as a scaffold. In particular, when the cell death protease recognition sequence is intact, the fluorescence quencher and the photoactivatable killing agent are held in proximity such that the fluorescence quencher facilitates quenching of fluorescence from the fluorophore of the photoactivatable killing agent. Once the cell death protease recognition sequence undergoes a conformation change or is cleaved, the fluorescence quencher and the photoactivatable killing agent are no longer held in proximity and the fluorophore photoactivatable killing agent is no longer quenched. Cell death protease recognition sequences may include polypeptides, nucleic acid molecules, synthetic polymers, phospholipids, galactose-containing compounds, or combinations thereof. In one embodiment the photoactivatable killing agent and fluorescence quencher are attached to the cell death protease recognition sequence by a linker molecule.

In one embodiment, the cell death protease recognition sequence is a polypeptide which contains a site which is cleavable by an enzyme, preferably a proteinase. Suitable enzymes are proteases, such as caspases.

Recognition of the central role of caspases in the programmed cell death process (apoptosis) has led to the development of assays that can measure these important enzymes in situ. Caspase activation represents one of the earliest known markers for the onset of apoptosis. In most instances, caspase activation precedes cell permeability alterations and DNA damage, whereas cytoskeletal collapse and phosphatidylserine (PS) flipping are often more concurrent. Loss of mitochondrial membrane generally occurs prior to caspase activation. Several fluorogenic assays have been developed for in situ analysis of caspase activation in intact cells. These assays are useful for detecting localized caspase activation in early apoptotic cells. Accordingly, inclusion of a caspase cleavage site in the cell death protease recognition sequence of the conjugates enables the monitoring of the effectiveness of the photoactivatable killing agents in real time.

In one embodiment, the cell death protease recognition sequence comprises a sequence selected from the group consisting of Asp-Glu-Val-Ile(SEQ ID NO: 1), Asp-Glu-Thr-Asp (SEQ ID NO: 2), Leu-Glu-His-Asp(SEQ ID NO: 3), Asp-Glu-His-Asp(SEQ ID NO: 4), Trp-Glu-His-Asp(SEQ ID NO: 5), Leu-Glu-Thr-Asp(SEQ ID NO: 6), Asp-Glu-Val-Asp (SEQ ID NO: 7), Val-Glu-His-Asp(SEQ ID NO: 8), and Ile-Glu-Ala-Asp(SEQ ID NO: 9).

In another embodiment, the cell death protease recognition sequence comprises a sequence selected from the group consisting of X-Asp-Glu-Val-Ile(SEQ ID NO: 1)-Y, X-Asp-Glu-Thr-Asp(SEQ ID NO: 2)-Y, X-Leu-Glu-His-Asp(SEQ ID NO: 3)-Y, X-Asp-Glu-His-Asp(SEQ ID NO: 4)-Y, X-Trp-Glu-His-Asp(SEQ ID NO: 5)-Y, X-Leu-Glu-Thr-Asp(SEQ ID NO: 6)-Y, X-Asp-Glu-Val-Asp(SEQ ID NO: 7)-Y, X-Val-Glu-His-Asp(SEQ ID NO: 8)-Y, and X-Ile-Glu-Ala-Asp (SEQ ID NO: 9)-Y, wherein X and Y are each independently a polypeptide comprising from one to about 15 amino acids. In one embodiment, the cell death protease recognition sequence comprises the amino acid sequence Asp-Glu-Val-Asp(SEQ ID NO: 7). In another embodiment, the cell death protease recognition sequence comprises the amino acid sequence Gly-Asp-Glu-Val-Asp-Gly-Ser-Gly-Lys (SEQ ID NO: 10). In yet another embodiment, the cell death protease recognition sequence comprises the amino acid sequence Lys-Gly-Asp-Glu-Val-Asp-Gly-Ser-Gly-Lys (SEQ ID NO: 11).

In an embodiment, when the photoactivatable killing agent is attached to X, a fluorescence quencher is attached to Y, and when a fluorescence quencher is attached to X, a photoactivatable killing agent is attached to Y. In one embodiment, there are at least from about 3 to about 10 amino acids between the photoactivatable killing agent and the fluorescence quencher. In another embodiment, there are from about 4 to about 8 amino acids between the photoactivatable killing agent and the fluorescence quencher. In yet another embodiment, there are from about 5 to about 7 cell death protease recognition sequence amino acids between the photoactivatable killing agent and the fluorescence quencher.

In one aspect of the present invention, X and Y are each independently from 1 to about 25 amino acids, more preferably from 2 to about 15 amino acids, and even more preferably, from about 5 to about 10 amino acids in length.

In another embodiment, when the cell death protease recognition sequence is a polypeptide, when the photoactivatable killing agent is attached to the N-terminal amino acid of the polypeptide the fluorescence quencher is attached to the C-terminal amino acid of the polypeptide, and when the photoactivatable killing agent is attached to the C-terminal amino acid of the polypeptide, the fluorescence quencher is attached to the N-terminal amino acid of the polypeptide.

In one embodiment the cell death protease recognition sequence is a polypeptide cleavable by a caspase enzyme. In such embodiments, the cell death protease recognition sequence may be cleavable by a protease selected from the group consisting of caspase-1, caspase-2, caspase-3, caspase-4, caspase-5, caspase-6, caspase-7, caspase-8, caspase-9, and caspase-10. In one such embodiment, the protease is caspase-1, caspase-3 or caspase-9.

In one embodiment, the conjugate comprises pyropheophorbide (Pyro) as a photoactivatable killing agent, a black hole quencher (BHQ) as a fluorescence quencher (Q), the cell death protease recognition sequence between Pyro and Q comprising a caspase-3 cell death protease recognition sequence: GDEVDGSGK (SEQ ID NO: 10) or KGDEVDGSGK (SEQ ID NO: 11).

Photoactivatable Killing Agents

As discussed previously, in certain aspects the conjugates of the present invention comprise a cell death protease recognition sequence, a fluorescence quencher, a photoactivatable killing agent, and a targeting ligand. As used herein, the term "photoactivatable killing agent" encompasses any agent suitable for use in photodynamic therapy. If not quenched, such agents become activated upon exposure to light and oxygen, producing lethal reactive oxygen species that kill, for example, tumor cells. Accordingly, an activated form of a photoactivatable killing agent produces lethal reactive oxygen species. In a one embodiment, the photoactivatable killing agents used in the present invention generate singlet oxygen upon exposure to oxygen and light of the appropriate wavelength. In another embodiment, photoactivatable killing agents comprise a fluorophore. A fluorophore is any material capable of emitting fluorescence.

In an aspect of the present invention, the photoactivatable killing agent is a free base or metal complex of a compound selected from the group consisting of a porphyrin (e.g., porphyrin), a reduced porphyrin (e.g., chlorin), a chlorophyll, a chlorophyll derivative (e.g., phyropheophorbide, chlorin e6, chlorin p6 and purpurin 18), synthetic chlorin (e.g., a benzoporphyrin derivative and purpurin), bacteriochlorin (e.g., bacteriochlorophyll derivative, synthetic bacteriochlorin, porphyrin isomer (e.g., porphycene, heteroatom-fused porphyrin and inverted porphyrin), an expanded porphyrin (e.g., texaphyrin), and porphyrin analog (e.g., phthalocyanine and naphthalocyanine). In addition, the photoactivatable killing agent can be a nonporphyrin (e.g., hypericin, cationic dye (i.e., rhodamine), psoralen, and merocyanine 540).

Additional photoactivatable killing agents for use in the conjugates of the present invention will be apparent to one of skill in the art. As stated above, photoactivatable killing agents may be those used in photodynamic therapy such as those photoactivatable killing agents that have undergone or are currently undergoing clinical trials. For example, photoactivatable killing agents listed in Pandey, R. K. and G. Zheng, "Porphyrins as Photoactivatable killing agents in Photodynamic Therapy" in *The Porphyrin Handbook*, Kadish, K. M. et al. Eds., Academic Press (2000), which is hereby incorporated by reference in its entirety, can be used in the conjugates of the present invention.

Fluorescence Quenchers

As used herein, the term "fluorescence quencher" encompasses any agent which quenches fluorescence of a photoactivatable killing agent so that no photoreaction occurs upon exposure to light and oxygen. In one embodiment of the present invention, the fluorescence quencher used in the conjugates of the present invention is a carotenoid, a metal complex dye, a cyanine dye, a stilbene quinone dye, an azomethine dye, an amine, a phenol, a sulfide, a bilirubin, a biliverdin, a nitroso compound, a nitrone compound or a N-oxy compound.

In one embodiment, the fluorescence quencher is a nonfluorescent chromophore that overlaps with the photoactivatable killing agent's emission (a black hole quencher). Fluorescence quenchers include DABCYL (4-(4'-dimethylaminophenylazo) benzoic acid), BHQ0, BHQ1, BHQ2 and BHQ3 (Biosearch Technologies, Inc., Novato, Calif.). In one embodiment, the fluorescence quencher is BHQ3. The fluorescence quencher quenches fluorescence of the photoactivatable killing agent with minimal affect on the ability of the photoactivatable killing agent to produce singlet oxygen.

Targeting Ligands

As used herein, the term "targeting ligand" encompasses any agent which selectively binds to a cell or tissue to be treated with the conjugates of the invention. In one embodiment, targeting ligands selectively bind to tumor tissue or cells versus normal tissue or cells of the same type. The targeting ligands in general may be ligands for cell surface receptors that are over-expressed in tumor tissue. Cell surface receptors over-expressed in cancer tissue versus normal tissue include epidermal growth factor receptor (EGFR) (overexpressed in anaplastic thyroid cancer and breast and lung tumors), metastin receptor (overexpressed in papillary thyroid cancer), ErbB family receptor tyrosine kinases (overexpressed in a significant subset of breast cancers), human epidermal growth factor receptor-2 (Her2/neu) (overexpressed in breast cancers), tyrosine kinase-18-receptor (c-Kit) (overexpressed in sarcomatoid renal carcinomas), HGF receptor c-Met (overexpressed in esophageal adenocarcinoma), CXCR4 and CCR7 (overexpressed in breast cancer), endothelin-A receptor (overexpressed in prostate cancer), peroxisome proliferator activated receptor delta (PPAR-delta) (overexpressed in most colorectal cancer tumors), PDGFR A (overexpressed in ovarian carcinomas), BAG-1 (overexpressed in various lung cancers), soluble type II TGF beta receptor (overexpressed in pancreatic cancer) folate and integrin (e.g. $\alpha v \beta 3$).

The folate receptor may be a glycosylphosphatidylinositol-anchored glycoprotein with high affinity for the vitamin folic acid (Kd~$10^{-9}$ M) (Leamon, C. P. et al., Biochemical Journal. 1993 May 1; 291 (Pt.3):855-60). The folate receptor has been identified as a tumor-marker which is expressed at elevated levels relative to normal tissues on epithelial malignancies such as, for example ovarian, colorectal and breast cancer (Wang, S. et al., Journal of Controlled Release, 1998 Apr. 30; 53(1-3): 39-48). It has been shown that when folate is covalently linked to either a single molecule or assembly of molecules via its γ-carboxyl moiety, its affinity for the cell surface receptors remains essentially unaltered. Following endocytosis and vesicular trafficking, much of the material is released into the cell cytoplasm. The folate receptor may then recycle to the cell surface. Thus, each folate receptor may bring many folate conjugates into the cell.

In one embodiment, the targeting ligand is a cell surface receptor ligand for a receptor selected from the group consisting of folate, Her-2/neu, integrin, EGFR, metastin, ErbB, c-Kit, c-Met, CXR4, CCR7, endothelin-A, PPAR-delta, PDGFR A, BAG-1, and TGF beta. In one such embodiment, the targeting ligand is a cell surface receptor ligand for folate receptor.

In one embodiment, the photoactivatable killing agent and the fluorescence quencher are covalently linked to opposite ends of the cell death protease recognition sequence. In such an embodiment, the targeting ligand can be covalently linked to the cell death protease recognition sequence, the photoactivatable killing agent, or the fluorescence quencher as long as the targeting ligand is not linked in such a manner so that interference of cleavage of the cell death protease recognition sequence does not occur.

In another embodiment, the targeting ligand and the fluorescence quencher are covalently linked to the cell death protease recognition sequence. In such an embodiment, the photoactivatable killing agent can be covalently linked to the cell death protease recognition sequence or the targeting ligand as long as the photoactivatable killing agent is covalently linked on the opposite end of the conjugate as the fluorescence quencher and so that interference of cleavage of the cell death protease recognition sequence does not occur.

In another embodiment, the targeting ligand and the photoactivatable killing agent are covalently linked to the cell death protease recognition sequence. In such an embodiment, the fluorescence quencher can be covalently linked to the cell death protease recognition sequence or the targeting ligand as long as the fluorescence quencher is covalently linked on the opposite end of the conjugate as the photoactivatable killing agent quencher and so that interference of cleavage of the cell death protease recognition sequence does not occur.

In one embodiment, the conjugate comprises the following chemical structure:

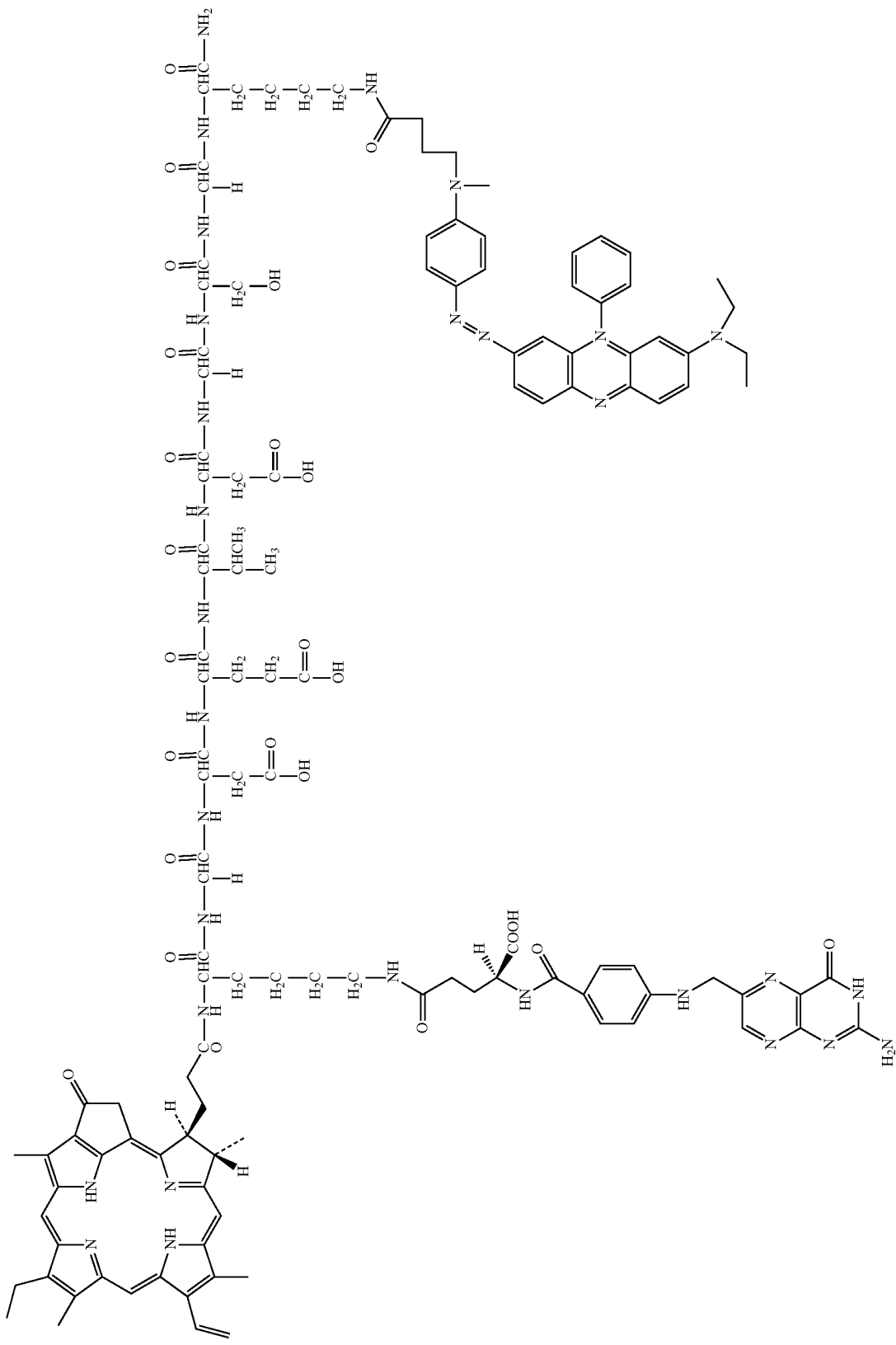

Two designations for amino acids are used herein, as is common practice in the art: Alanine=Ala (A); Arginine=Arg (R); Aspartic Acid=Asp (D); Asparagine=Asn (N); Cysteine=Cys (C); Glutamic Acid=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

In one embodiment of the present invention, when the photoactivatable killing agent is attached to X a quencher is attached to Y, and when a quencher is attached to X, a photoactivatable killing agent is attached to Y. There are at least from about 3 to about 10 substrate amino acids between the photoactivatable killing agent and the quencher. In one embodiment, there are from about 4 to about 8 substrate amino acids between the photoactivatable killing agent and the quencher. In another embodiment, there are from about 5 to about 7 substrate amino acids between the photoactivatable killing agent and the quencher.

In an aspect of the present invention, X and Y are each independently from 1 to about 25 amino acids. In one embodiment, X and Y are each independently from 2 to about 15 amino acids, and in another embodiment, from about 5 to about 10 amino acids in length.

In a further embodiment in which the substrate is a polypeptide, when the photoactivatable killing agent is attached to the N-terminal amino acid of the polypeptide the quencher is attached to the C-terminal amino acid of the polypeptide, and when the photoactivatable killing agent is attached to the C-terminal amino acid of the polypeptide the quencher is attached to the N-terminal amino acid of the polypeptide.

In one embodiment, when the substrate of the present invention is a polypeptide and contains a protease-cleavable site, the protease-cleavable site may be recognized by an aspartic proteinase. Aspartic proteinases are proteolytic enzymes which generally operate at acidic pH. Commonly an aspartic proteinase can accommodate about 7 residues of a substrate in its active site cleft. These residues are usually designated as P4-P3-P2-P1*P1'-P2'-P3' with the scissile peptide bond between P1 and P1' indicated by "*". The corresponding subsites that constitute the topography of the active site cleft in each enzyme are designated accordingly as S4-S3-S2-S1-S1'-S2'-S3'. The scissile peptide bond between P1 and P1' residues normally consists of two hydrophobic residues although beta branched side chains such as valine or isoleucine are not favored in the P1 position. Generally, each lobe of an aspartic proteinase contributes one aspartic acid residue to the catalytic apparatus. These Asp residues are present in two ~Hydrophobic-Hydrophobic-Asp-Thr/Ser-Gly~ motifs. In pepsin, the catalytic Asp residues are at positions 32 and 215. It is the essential role of these residues in coordinating a water molecule for nucleophilic attack on the scissile peptide bond which gives this class of enzyme its name.

An increasing number of aspartic proteinases are being characterized from vertebrates, insects, helminths, protozoans, plants, retroviruses and bacteria, and all such aspartic proteinases are encompassed within the definition of aspartic proteinase as used herein. Aspartic proteinases include rennin, chymosin and pepsin, an din one embodiment comprise HIV-1 retropepsin. HIV proteinase is a member of the aspartic proteinase family of enzymes and is encoded by the virus and is essential to allow processing of the viral polyprotein. In contrast to the archetypal aspartic proteinases which are single chain enzymes, HIV proteinase is a homodimeric enzyme. Other retroviruses that infect vertebrates and plants produce aspartic proteinases which, like HIV proteinase, are symmetrical dimers.

Each monomer contributes an aspartic acid residue (Asp25) to the catalytic apparatus of the enzyme. As in the single chain aspartic proteinases, these Asp residues are found in ~Hydrophobic-Hydrophobic-Asp-Thr-Gly~ motifs.

Many diseased tissues (e.g., tumors) have been shown to have elevated levels of proteolytic enzymes, presumably in adaptation to rapid cell cycling and for secretion to sustain invasion, metastasis formation, and angiogenesis. In one aspect of the present invention, the conjugates of the present invention comprise substrates which have sites which are cleavable by such proteases. For example, in one embodiment the conjugates of the present invention are cleavable by viral enzymes. Such viral enzymes include the following: HIV protease, cytomegalovirus protease, Epstein-Barr virus protease, hepatitis B virus protease, hepatitis C virus protease, herpes simplex virus protease, cathepsin B, cathepsin D, a matrix metalloproteinase, cathepsin K, prostate-specific antigen, thrombin, caspase-3, and interleukin 1β converting enzyme. In one embodiment, the protease is human immunodeficiency virus type I protease.

The conjugates of the present invention comprise substrates which are cleavable by thrombin, enzymes present during an inflammatory response, proteases (e.g., caspase 3 and 8), lipases (e.g., phospholipase A2), glycosidases (e.g., β-galactosidase), phosphatases (e.g., adenosine triphosphatase (ATPase), guanosine triphosphatase (GTPase), protein tyrosine phosphatase, deoxyribonuclease (DNAse), ribonuclease (RNAse), or esterases (e.g., phosphodiesterase).

Figure 1:
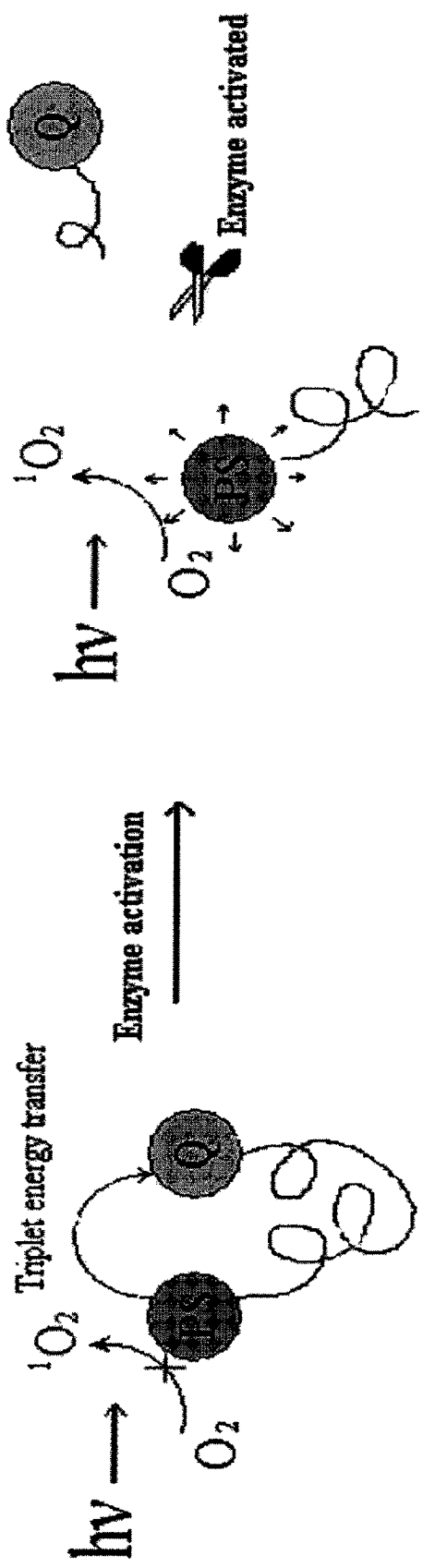
Figure 2:
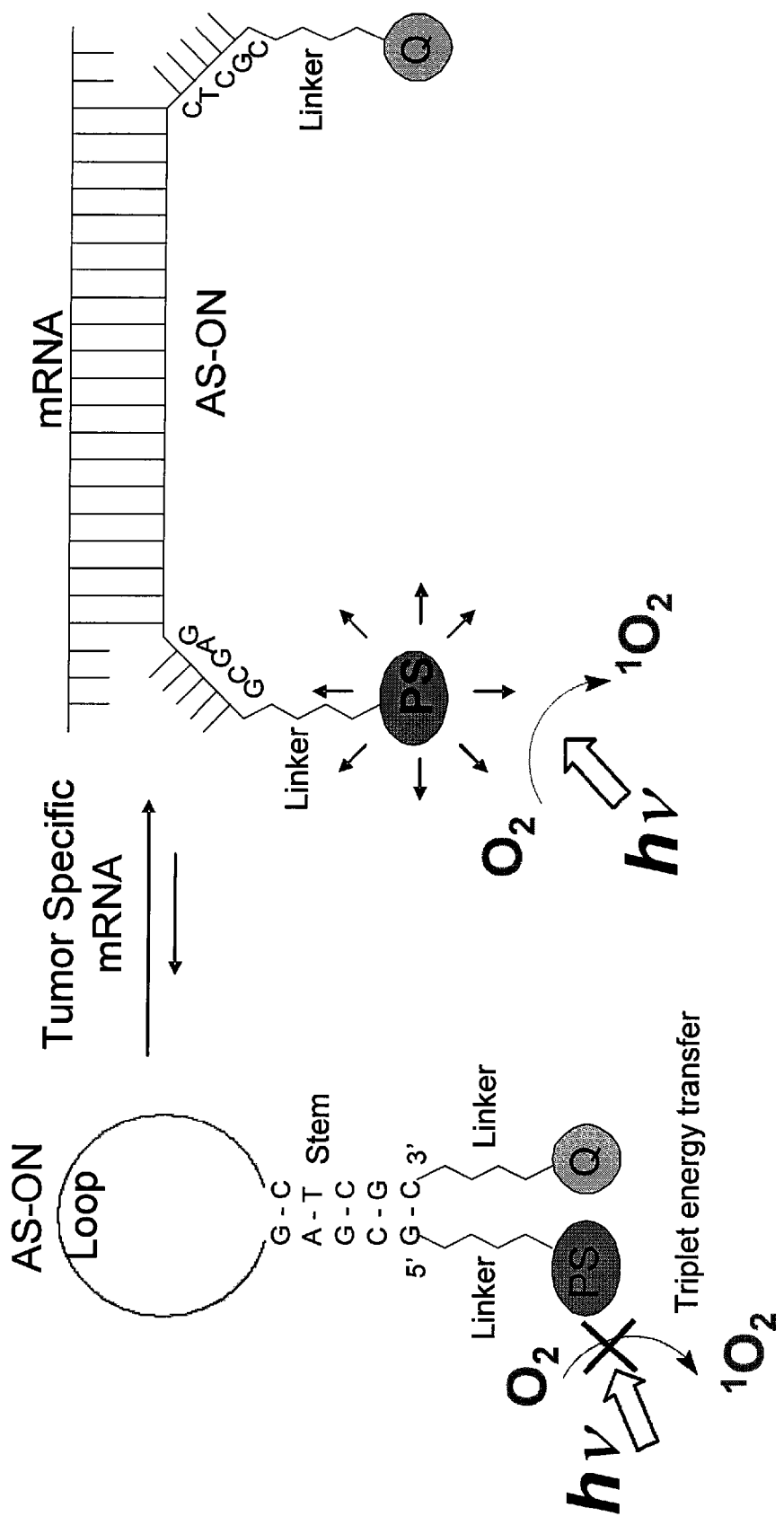
FIG. 2 depicts a conjugate which has an anti-sense nucleic acid as a substrate.

Another aspect of the invention is directed to a conjugate which comprises a substrate comprising a phospholipid which contains one or more sites which are cleavable by one or more phospholipase enzymes. Phospholipases are enzymes that catalyze phospholipid breakdown. As illustrated in FIG. 2, phospholipases are categorized as A1, A2, C and D based on their site of action. Phospholipase A1 and A2 (PLA1 and PLA2) remove fatty acid chains from the sn-1 and sn-2 positions of the glycerol backbone of a variety of phospholipids (Jackowski, S., J. Biol. Chem. 269:3858 (1994)). Phospholipase C (PLC) specifically hydrolyzes the P—O bond adjacent to the glycerol sn-3 position to produce diacylglycerol and the corresponding phosphorylated head group. Phospholipase D (PLD) hydrolyzes the O—P bond adjacent to the head group, releasing the head group and a molecule of phosphatidic acid. Phospholipases are common enzymes in plants and animals, and perform a number of critical regulatory functions. Phospholipases are involved in signal transduction, for the maintenance and turnover of membranes, as mediators or inflammation and immunity, and also act as digestive enzymes both at the cellular (i.e. lysosomal) level as well as being crucial to the absorption of nutrients through the gut.

Phospholipase A2 catalyzes the hydrolysis of the sn-2 bond of a phospholipid, creating a lysophospholipid and releasing a fatty acyl chain. Phospholipase A2 is critical in a number of functions at the cellular and tissue level as a modulator of inflammation, as an important regulator of immune function, as a controlling factor in signal transduction and in membrane re-modeling. PLA2 levels are increased during inflammatory response and in hyperproliferation. There are numerous isoforms of PLA2, which are generally divided into three categories on the basis of molecular weight and requirement for calcium. Among them, Type II PLA2 (sPLA2) is secreted by a number of cell types including eosinophils, mast cells and neutrophils. It is found in sera and inflammatory exudates of patients with chronic inflammatory diseases. sPLA2 has a specificity for phosphatidylethanolamine (PtdEtn) over phosphatidylcholine (PtdCho). The specificity for PtdEtn acts as a protection from self-hydrolysis, the outer leaflet of the plasma membrane is low in PtdEtn, whereas gram negative bacteria have membranes rich in PE. This enzyme can also act intracellularly for fatty acid turnover. sPLA2 levels are elevated in prostate cancer compared to normal prostate cells (Graff et al., Clinical Cancer Res. 7:3857 (2001)).

In an additional embodiment, the present invention is directed to a conjugate which comprises a substrate having a site specific for Type II PLA2 (sPLA2). The conjugate may be a compound of Formula I:

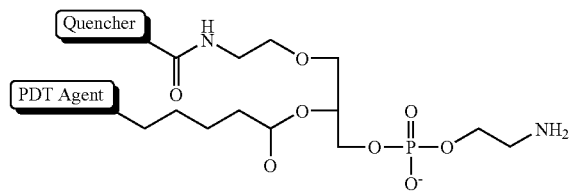

I wherein Q is a quencher and P is a photoactivatable killing agent.

In another embodiment, the substrate is a nucleic acid. Nucleic acids of the present invention can comprise any nucleotide including adenine (A), cytosine (C), guanine (G), thymidine (T), and uracil (U) and analogs thereof. The backbone of the nucleic acids include a phosphodiester, a methyl phosphonate, a phosphorothioate, a borane phosphonate, a 3'-O-phosphopropylamino, a N3'-phosphoramidate, a 2'-O-alkyl-RNA, a morpholinophosphorodiamidate, and a peptide nucleic acid.

In one embodiment, the substrate is a single stranded nucleic acid. The nucleic acid may comprise a first portion, a second portion, and a third portion, wherein the first portion and the third portion are at least 70% complementary to each other. Complementarity refers to Watson-Crick base pairing: adenine pairs with thymidine and uracil; guanine pairs with cytosine. In other embodiments first portion and the third portion are at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% complementary to each other. In one embodiment, the first portion and the third portion are 100% complementary to each other. In yet another embodiment, the first portion and the third portion are capable of base pairing resulting in a stem-loop structure wherein the first portion and the third portion form the stem and the second portion forms a non-base-paired loop region. If the first quencher is attached to the first portion, then the photoactivatable killing agent is attached to the third portion. If the photoactivatable killing agent is attached to the first portion, then the first quencher is attached to the third portion. The first portion and the third portion need not be exactly the same length, but the first portion and the third portion may be the same length. In one embodiment, the first portion and the third portion are both about 3 to about 10 nucleotides in length, preferably about 3 to about 7 nucleotides in length. In another embodiment the first portion and the third portion are both about 5 nucleotides in length. In yet another embodiment, the first portion is 5'-gcgag-3' and the third portion is 5'-ctcgc-3'.

The second portion of the nucleic acid may comprise any nucleotide sequence. In one such embodiment the second portion is about 10 to about 50 nucleotides in length. In another embodiment, the second portion is about 10 to about 30 nucleotides in length. In yet another embodiment, the second portion is about 15 to about 25 nucleotides in length. The second portion is a nucleic acid which may be complementary to an mRNA molecule, such as an mRNA which is overexpressed in a diseased cell. In one embodiment, the mRNA is expressed at high levels in a cancer cell as compared to a normal cell. The second portion may be at least 70% identical to a nucleic acid sequence complementary to a nucleic acid sequence selected from the group consisting of c-Raf-1 mRNA, BRAF1 mRNA, DD3 mRNA, K-ras mRNA, CCND1 mRNA, and EGFRvIII mRNA. In one embodiment, the second portion is at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% complementary to a nucleic acid sequence selected from the group consisting of c-Raf-1 mRNA, BRAF1 mRNA, DD3 mRNA, K-ras mRNA, CCND1 mRNA, and EGFRvIII mRNA. In another embodiment, the second portion is 100% complementary to a nucleic acid sequence selected from the group consisting of c-Raf-1 mRNA, BRAF1 mRNA, DD3 mRNA, K-ras mRNA, CCND1 mRNA, and EGFRvIII mRNA. In yet another embodiment, the second portion is SEQ ID NO:18, 5'-agctag-gaaacaccaaagatgatatttg-3', or SEQ ID NO:19 5'-tcccgcctgt-gacatgcatt-3'. Accordingly, embodiments of the nucleic acid include SEQ ID NO:20, 5'-gcgagagctaggaaacaccaaagat-gatatttgctcgc-3', and SEQ ID NO:21, 5'-gcgagtcccgcctgtga-catgcattctcgc-3'.

The present invention also is related to conjugates comprising a substrate, a cell death protease recognition sequence wherein the substrate is covalently linked to the cell death protease recognition sequence, a first quencher attached to the substrate, a second quencher attached to the cell death protease recognition sequence, the second quencher comprising a fluorescence quencher, and a photoactivatable killing agent attached to the covalently linked substrate and cell death protease recognition sequences and the photoactivatable killing agent comprising a fluorophore, wherein the substrate allows the photoactivatable killing agent and the first quencher to come sufficiently close to each other to facilitate quenching of an activated form of the photoactivatable killing agent, and wherein the cell death protease recognition sequence allows the photoactivatable killing agent and the second quencher to come sufficiently close to each other to facilitate quenching of fluorescence from the fluorophore of the photoactivatable killing agent. Accordingly, the photoactivatable killing agent may be attached to substrate, the cell death protease recognition sequence, or the junction of the substrate and cell death protease recognition sequences.

The substrates of this conjugate are as described above and include polypeptides, nucleic acid molecules, synthetic polymers, phospholipids, galactose-containing compounds, or combinations thereof. In one embodiment, the photoactivatable killing agent and the second quencher are attached to the cell death protease recognition sequence by a linker molecule.

Cell death protease recognition sequences may be as described above. In one embodiment, the cell death protease recognition sequence is a cleavable polypeptide. In another embodiment, the cell death protease recognition sequence is a polypeptide. In yet another embodiment, the cell death protease recognition sequence is cleavable by a caspase enzyme. In still another embodiment, the cell death protease recognition sequence is cleavable by a protease selected from the group consisting of caspase-1, caspase-2, caspase-3, caspase-4, caspase-5, caspase-6, caspase-7, caspase-8, caspase-9, and caspase-10. In yet another embodiment, the protease is caspase-1, caspase-3, or caspase-9.

In one embodiment, the substrate and the cell death protease recognition sequence are polypeptides, and the C-terminal amino acid of the substrate and the N-terminal amino acid of the cell death protease recognition sequence are covalently linked by a peptide bond. In another embodiment, the photoactivatable killing agent is attached to either the C-terminal amino acid of the substrate or the N-terminal amino acid of the cell death protease recognition sequence, the first quencher is attached to the N-terminal amino acid of the substrate, and the second quencher is attached to the C-terminal amino acid of the cell death protease recognition sequence.

In an alternative embodiment, the substrate and the cell death protease recognition sequence are polypeptides, and the C-terminal amino acid of the cell death protease recognition sequence and the N-terminal amino acid of the substrate are covalently linked by a peptide bond. In another embodiment, the photoactivatable killing agent is attached to the C-terminal amino acid of the cell death protease recognition sequence or the N-terminal amino acid of the substrate, the first quencher is attached to the C-terminal amino acid of the substrate, the second quencher is attached to the N-terminal amino acid of the cell death protease recognition sequence.

In one embodiment the cell death protease recognition sequence comprises a sequence selected from the group consisting of Asp-Glu-Val-Ile(SEQ ID NO:1), Asp-Glu-Thr-Asp (SEQ ID NO:2), Leu-Glu-His-Asp(SEQ ID NO:3), Asp-Glu-His-Asp(SEQ ID NO:4), Trp-Glu-His-Asp(SEQ ID NO:5), Leu-Glu-Thr-Asp(SEQ ID NO:6), Asp-Glu-Val-Asp(SEQ ID NO:7), Val-Glu-His-Asp(SEQ ID NO:8), and Ile-Glu-Ala-Asp(SEQ ID NO:9).

In an alternative embodiment, the cell death protease recognition sequence comprises a sequence selected from the group consisting of X-Asp-Glu-Val-Ile(SEQ ID NO: 1)-Y, X-Asp-Glu-Thr-Asp(SEQ ID NO: 2)-Y, X-Leu-Glu-His-Asp (SEQ ID NO: 3)-Y, X-Asp-Glu-His-Asp(SEQ ID NO: 4)-Y, X-Trp-Glu-His-Asp(SEQ ID NO: 5)-Y, X-Leu-Glu-Thr-Asp (SEQ ID NO: 6)-Y, X-Asp-Glu-Val-Asp(SEQ ID NO: 7)-Y, X-Val-Glu-His-Asp(SEQ ID NO: 8)-Y, and X-Ile-Glu-Ala-Asp(SEQ ID NO: 9)-Y, wherein X and Y are each independently a polypeptide comprising from one to about 15 amino acids and the N-terminal amino acid of X is covalently linked to the substrate.

In an alternative embodiment, the cell death protease recognition sequence comprises a sequence selected from the group consisting of X-Asp-Glu-Val-Ile(SEQ ID NO: 1)-Y, X-Asp-Glu-Thr-Asp(SEQ ID NO: 2)-Y, X-Leu-Glu-His-Asp (SEQ ID NO: 3)-Y, X-Asp-Glu-His-Asp(SEQ ID NO: 4) Y, X-Trp-Glu-His-Asp(SEQ ID NO: 5)-Y, X-Leu-Glu-Thr-Asp (SEQ ID NO: 6)-Y, X-Asp-Glu-Val-Asp(SEQ ID NO: 7)-Y, X-Val-Glu-His-Asp(SEQ ID NO: 8)-Y, and X-Ile-Glu-Ala-Asp(SEQ ID NO: 9)-Y, wherein X and Y are each independently a polypeptide comprising from one to about 15 amino acids and the C-terminal amino acid of Y is covalently linked to the substrate.

In one embodiment, the conjugate comprises pyropheophorbide (Pyro) as a photoactivatable killing agent, a carotenoid (Car) as a first quencher (Qs), a black hole quencher (BHQ) as a second quencher (Qf), with the cell death protease recognition sequence between Pyro and Qs comprising a caspase-3 substrate (GDEVDGSGK) (SEQ ID NO:10).

Methods of Treatment

The present invention is directed to a method for inhibiting the growth of cancer cells, in vitro or in vivo, comprising the steps of contacting the cancer cells with a conjugate of the present invention and exposing the cancer cells to an effective amount of artificial radiation. In one aspect, the invention provides methods of inhibiting the growth of cancer cells such as, for example, breast, lung, pancreas, bladder, ovarian, testicular, prostate, retinoblastoma, Wilm's tumor, adrenocarcinoma or melonoma.

The present invention is also directed to a method for inhibiting plaque formation in blood vessels comprising the steps of contacting a subject's blood and/or blood vessels with a conjugate of the present invention and exposing the blood and/or blood vessels to an effective amount of artificial radiation.

The present invention is further directed to a method for decontaminating blood comprising contacting blood with the conjugates of the present invention and exposing the blood and conjugate mixture to an effective amount of artificial radiation. As used herein, "decontaminating" means that the level of infectious virus is reduced in such a manner that the majority of all of the infectious virus contained in the blood is destroyed or inactivated. In one embodiment, 60%, 70%, 80%, 90%, 95%, 96%, 97%, 98% or 99% of the virus in the blood is destroyed or inactivated. The present invention provides blood decontamination methods that inactivate or reduce the viral count in the blood by about 1 to about 20 log, by about 2 to about 15 log, and by about 4 to about 6 log.

The term "blood" as used herein encompasses whole blood, and fractions of whole blood, such as plasma. The term "contacting" as used herein encompasses mixing or stirring the conjugates of the present invention, which may be present in a pharmaceutically acceptable carrier. A carrier is deemed "pharmaceutically acceptable" if it is compatible with the other ingredients of the formulation and is not deleterious. For example, the conjugates of the present invention may be combined with a sterile aqueous solution which may be isotonic with the virus-containing blood. Such formulations may be prepared by combining the conjugate formulation with water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

In one embodiment, radiation is applied immediately following contact between the conjugates of the present invention and the blood. In another embodiment, the radiation is applied from about 1 minute to about 3 hours following contact between the conjugates of the present invention and the blood. In yet another embodiment, radiation is applied from about 5 to about 60 minutes following contact between the conjugates of the present invention and the blood. The radiation may be applied at a sufficient wavelength, dose and duration to maximize the inactivation of infectious virus, and at the same time, to minimize the damage to the red blood cells and/or other surrounding tissue.

The specific wavelength dose and duration of radiation again will depend upon the particular photoactivatable killing agent chosen and/or the contamination of the blood. The dose of radiation applied may be about 5-25 mW/cm$^2$, or about 18-22 mW/cm$^2$, while the duration of radiation application is about 5-60 minutes, or about 20-30 minutes. Suitable sources of radiation include commercially available lasers, lamps, light emitting diodes and the like. Preferably, LED arrays manufactured by Efos Canada, Inc., Mississauga, Ontario, Canada may be employed. To achieve the desired wavelength, the lamp may be equipped with commercially available filters.

Various photoactivatable killing agents for use in the present invention are useful over the range of 350 to 1300 nm, the exact range being dependent upon the particular photoactivatable killing agent. Photoactivatable killing agents may be those useful in the range of 650-1000 nm (i.e., in the near infrared ("NIR")). For example, pyropheophorbide is useful in the 650-900 nm range.

It also is within the scope of the present invention that one or more quenchers can be administered before, during or after the administration of the conjugates of the present invention, but before application of radiation. Suitable quenchers include glutathione, Trolox™, flavonoids, vitamin C, vitamin E, cysteine and ergothioneine and other non-toxic quenchers. The amount of the quencher administered will depend upon the specific quencher(s) chosen and can be determined by one skilled in the art. However, when the quencher is vitamin E, the dose may range from about 10 mg/kg body weight to about 1 g/kg body weight, and may be about 100 mg/kg body weight. Administering one or more of the aforementioned quenchers is optional, and is complimentary to administering the conjugates of the present invention. Complementary quenchers such as vitamin E quench free radical formation generated from a Type I photoreaction via electron transfer, and may be used as a complementary protection mechanism to quenching singlet oxygen that is generated from a Type II photoreaction via energy transfer. Nevertheless, singlet oxygen is the major cytotoxic agent responsible for PDT.

In one embodiment of the present invention, the artificial radiation is applied from about 5 minutes to about 3 hours after administering one or more types of conjugates of the present invention. The artificial radiation may be applied about 10-60 minutes after administering one or more kinds of conjugates of the present invention.

In one embodiment of the methods of the present invention, the artificial radiation is selected from the group consisting of artificial ultraviolet, infrared (IR), gamma-radiation, x-ray and visible light. In one such embodiment, the artificial radiation is IR, and in another such embodiment, the artificial radiation is near-infrared (NIR).

In one embodiment, the artificial radiation is applied at a wavelength ranging from about 20 nm less than the maximum absorption of the photoactivatable killing agent to about 20 nm greater than the maximum absorption of the photoactivatable killing agent.

In the methods of the present invention, the artificial radiation is applied about 30 minutes to about 48 hours after administering the conjugate of the present invention (e.g., by injection), or about 3 to about 24 hours after administering the conjugate of the present invention. The radiation dose is 10 mW/cm$^2$ to about 150 mW/cm$^2$, about 35 to about 100 mW/cm$^2$, or about 75 mW/cm$^2$.

In another embodiment of the methods of the present invention, the artificial radiation may be applied for about 5 seconds to about 60 minutes. In another embodiment, the artificial radiation may be applied for about 1 minute to about 45 minutes. In yet another embodiment, the radiation is applied for about 10 to about 30 minutes.

The present invention also provides a method for selectively killing tumor cells expressing an enzyme that specifically cleaves the substrate of the present invention or its functional equivalent. For example, this invention provides a method for treating carcinomas (for example human carcinomas) in vivo. This method comprises the steps of administering to a subject a pharmaceutically effective amount of a composition containing at least one of the conjugates of the present invention.

In accordance with the practice of this invention, the subject may be a human, equine, porcine, bovine, murine, canine, feline, and avian subjects. Other warm blooded animals are also included in this invention.

The present invention also provides a method for curing a subject suffering from a cancer. The subject may be a human, dog, cat, mouse, rat, rabbit, horse, goat, sheep, cow, chicken. The cancer may be identified as a breast, lung, pancreas, bladder, ovarian, testicular, prostate, retinoblastoma, Wilm's tumor, adrenocarcinoma or melonoma, and is generally characterized as a group of cells which over-express and/or have an over-abundance of specific cleavage enzymes. This method comprises the steps of administering to the subject a cancer killing amount of one or more conjugates of the present invention.

Also provided is a method for inhibiting the proliferation of mammalian tumor cells comprising the steps of contacting the mammalian tumor cells with a sufficient concentration of the conjugate of the invention, and exposing the tumor cells to artificial radiation.

The present invention further provides a method for inhibiting the growth of human tumor cells, treating a tumor in a subject, and treating a proliferative type disease in a subject. These methods comprise the steps of administering to the subject an effective amount of the conjugate of the invention.

The present invention also provides a method for treating a disease state comprising the steps of administering to a target tissue of a patient a conjugate of the present invention and irradiating the photoactivatable killing agent.

The present invention also provides a method for treating a disease state comprising the steps of administering to a target tissue of a patient a conjugate of the present invention and irradiating the photoactivatable killing agent, wherein a cell death protease recognition sequence is cleaved by a protease which removes a second quencher from a conjugate and allows fluorescence from a fluorophore of the photoactivatable killing agent to be detected.

The present invention also provides a method for treating a disease state comprising (a) administering to a target tissue of a patient a conjugate comprising the steps of:

a substrate comprising a nucleic acid wherein the nucleic acid comprises a first portion, a second portion, and a third portion, the first portion and the third portion capable of base-pairing resulting in a stem-loop structure wherein the first portion and the third portion form the stem and the second portion forms a non-base-paired loop region, at least one photoactivatable killing agent, and at least one first quencher, the photoactivatable killing agent and the first quencher attached to the substrate, said substrate capable of bringing said photoactivatable killing agent and the first quencher sufficiently close to each other to facilitate quenching of an activated form of the photoactivatable killing agent wherein said substrate undergoes a change of conformation in the target tissue such that formation of the stem-loop structure is inhibited, and (b) irradiating the photoactivatable killing agent thereby killing the target tissue.

In one embodiment, the change of conformation of the substrate is facilitated by the annealing of the second portion to a nucleic acid present in the target tissue.

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of the conjugate of the present invention and a pharmaceutically acceptable carrier.

The compositions may additionally include other drugs or antibodies treating carcinomas.

The conjugates of the invention can be administered using conventional modes of administration including, but not limited to, intravenous, intraperitoneal, oral, intralymphatic or administration directly into the tumor. Intravenous administration is preferred.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions as well as conjugates of the above with polyethylene glycol (pegylated carriers). The form will depend upon, among other things, the mode of administration and the therapeutic application.

The compositions of the invention also include conventional pharmaceutically acceptable carriers and adjuvants known in the art such as, for example, human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention will depend upon, among other things, the severity and course of the disease, the patient's health and response to treatment, and the judgment of the treating physician. Accordingly, the dosages of the compositions should be titrated to the individual patient. Nevertheless, an effective dose of the compositions of this invention may be in the range of from about 1 to about 2000 mg/kg. Other suitable dosage ranges include a dosage from about 2 to about 1000 mg/kg, 4 to about 400 mg/kg, and 5 to about 100 mg/kg.

The conjugates described herein may be in a variety of dosage forms which include liquid solutions or suspensions, tablets, pills, powders, suppositories, polymeric microcapsules or microvesicles, liposomes, and injectable or infusible solutions as well as conjugates of the above with polyethylene glycol (pegylated carriers). The preferred form will depend upon, among other things, the mode of administration and the therapeutic application.

The most effective mode of administration and dosage regimen for the conjugates of the present invention will depend upon, among other things, the location of the tumor being treated, the severity and course of the cancer, the subject's health and response to treatment, and the judgment of the treating physician. Accordingly, the dosages of the conjugates should be titrated to the individual subject.

The interrelationship of dosages for animals of various sizes and species and humans based on mg/kg of surface area is described by Freireich, E. J. et al., Cancer Chemother. 50 (4): 219-244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation.

The dose of the composition of the invention required to achieve cures may be further reduced with schedule optimization.

In accordance with the practice of the invention, the pharmaceutical carrier may be a lipid carrier or lipoprotein particle such as LDL, HDL, VLDL, IDL or chylomicron. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome or polymerosome as well as conjugates of the above with polyethylene glycol (pegylated carriers). As used in this application, a "liposome" is any membrane bound vesicle which contains any molecules of the invention or combinations thereof.

In another embodiment, the present invention is directed to a method for decontaminating blood in a subject comprising the steps of administering to the subject the conjugates of the present invention, and exposing said subject to an effective amount of artificial radiation. Subjects include mammals such as humans.

The human may be preferentially exposed to artificial radiation that is selected from the group consisting of artificial ultraviolet, infrared (IR), gamma-radiation, x-ray and visible light. In one embodiment the radiation is IR, and in another embodiment, the IR is near-infrared (NIR). In one embodiment, the artificial radiation is applied about 5 minutes to about 3 hours after administering the of the present invention. In another embodiment, the artificial radiation is applied about 10 to about 60 minutes after administering the conjugate of the present invention.

The amount of conjugate administered in the formulation will depend upon, among other things, the photoactivatable killing agent chosen. The amount of conjugate administered may be about 0.1 to about 10.0 mg/kg body weight of the subject, about 0.3 to about 6 mg/kg body weight, or about 0.4 to about 4.0 mg/kg body weight.

In embodiments of the method of treating cancer, the artificial radiation may be applied for about 10 seconds to about 60 minutes or for about 15 seconds to about 30 minutes.

In another embodiment, the present invention is directed to pharmaceutical compositions comprising the conjugates of the present invention and a pharmaceutically acceptable carrier.

The present invention further provides a method for treating cancer in a subject cancer comprising the steps of administering a therapeutically effective amount of the pharmaceutical composition of the present invention.

The present invention further provides a method for treating a viral infection in a subject, comprising the steps of administering a therapeutically effective amount of the pharmaceutical composition of the present invention.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Example 1

Preparation of a Conjugate

Synthesis of Photoactivatable Killing Agents—Stable Bacteriochlorophyll Analogs (BChl):

Bacteriochlorophyll (BChl) from *R. Sphaeroides* is an excellent near-infrared (NIR) dye for NIR imaging and photodynamic therapy (PDT), but it is unstable. This example describes efficient synthesis of isothiocyanate-containing BChl analogs derived from bacteriopurpurinimide (BChlPP) and bacteriochlorin e6 (BChlE6). Introducing an amine reactive universal linker such as isothiocyanate or succinimide ester into the BChl macrocycle allows conjugation of these NIR dyes to oligonucleotide or peptide by coupling of the terminal primary amine group.

Synthesis of Bacteriopurpurin-18-N-3'-(isothiocyanate)propylimide, BChlPP-NCS

Figure 5:
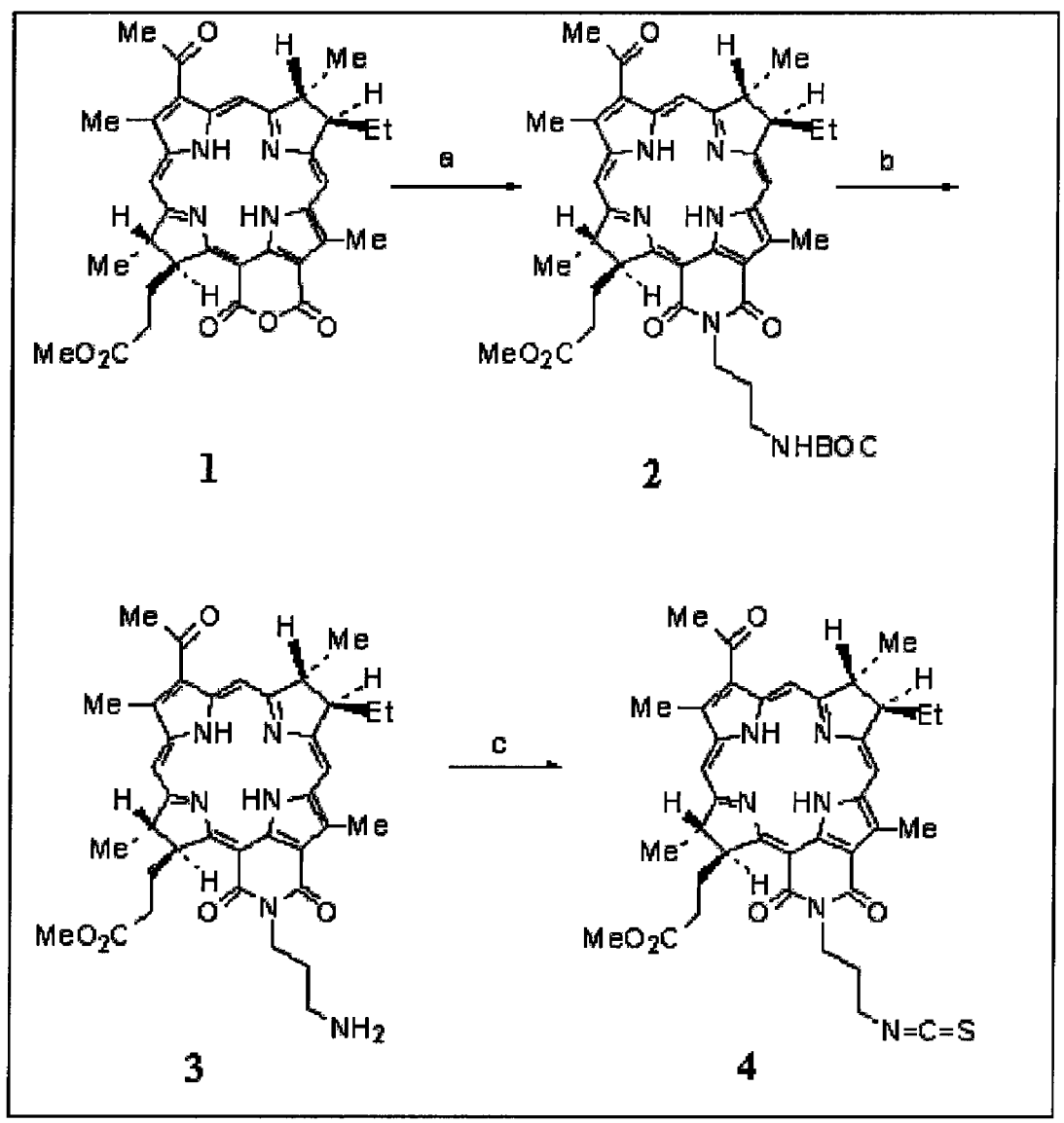
FIG. 5 depicts a synthesis of isothiocyanate-containing bacteriopurinimide, BChlPP-NCS.
Figure 6:
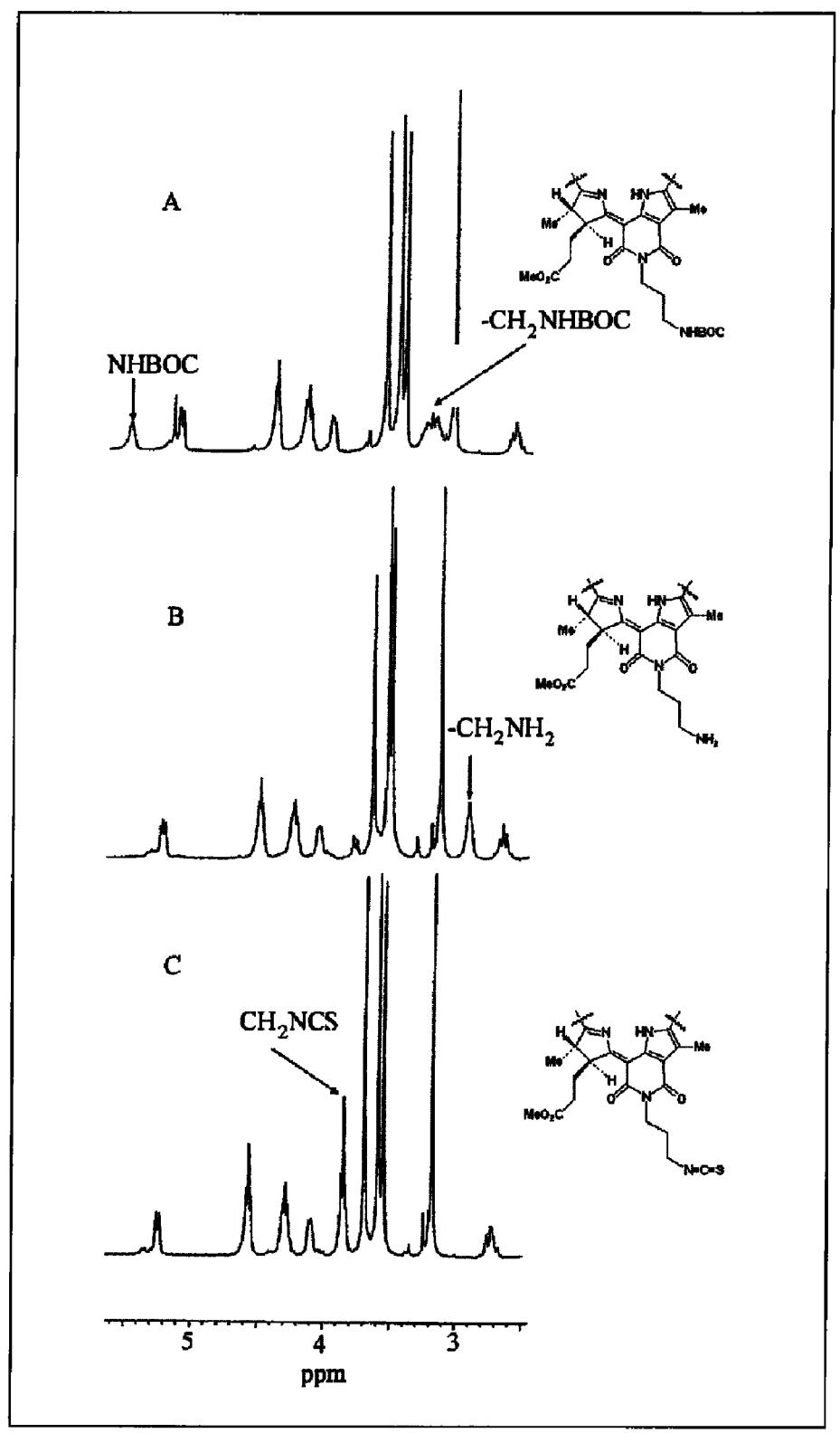
FIG. 6 depicts chemical shifts of $CH_2NHBOC$, $CH_2NH_2$ and $CN_2NCS$ in $^1H$ NMR spectra of functionalized bacteriochlorophylls.

Bacteriopurpurin-18-N-3'-(amino)propylimide (BChlPP-$NH_2$, was synthesized from bacteriopurpurin-18-N-3'-(BOC-amino)propylimide (BChlPP-BOC) and converted successfully to bacteriopurpurin-18-N-3'-(isothiocyanate) propylimide (BChlPP-NCS) as shown in FIG. 5 (Chen, Y., et al., J Med. Chem. 2002 Jan. 17; 45(2):255-8). However, the overall yield of BChlPP-NCS from BChlPP is just 10% with BChlPP-BOC formation as the yield-limiting step. The conversion of BChlPP to its corresponding BChlPP-BOC, BChlPP-$NH_2$ and BChlPP-NCS was clearly demonstrated by their NMR spectra. As shown in FIG. 5, the 5.62 and the 3.31 ppm peaks observed in the BChlPP-BOC spectrum (shown partially) belonged to the N—H proton and the $CH_2N$ protons adjacent to the BOC protection group, respectively. Cleavage of the BOC group led to the disappearance of the N—H peak and the upfield shift of the $CH_2N$ resonance to 2.95 ppm. Further conversion of BChlPP-$NH_2$ to BChlPP-NCS shifts the above mentioned $CH_2$ resonance downfield to 3.85 ppm. FIG. 6 shows the HPLC chromatogram and the absorption spectra of this compound.

Synthesis of Photoactivatable Killing Agents—Bacteriochlorin $e_6$-13-carboxy-N-3'-(isothiocyanate)propylamide (BChlE6-NCS)

To improve the feasibility of using BChl-based bioconjugates for cancer detection and treatment, another synthetic strategy to functionalize BChl was employed. Bacteriopheophorbide a methyl ester was first reacted with tert-butyl N-(-3-aminopropyl)-carbamate to form a single regioisomer, bacteriochlorin $e_6$-13-carboxy-N-3'-(BOC-amino)propylamide, BChlE6-BOC. This intermediate was then converted to its corresponding amino- and isothiocyanate-containing BChl (BChlE6-NH$_2$ and BChlE6-NCS) as described above. Compared with the previous procedure (10% overall yield from BChlPP to BChlPP-NCS, see FIG. 5), the new synthetic route from bacteriopheophorbide a methyl ester to BChlE6-NCS shown in FIG. 8 has the overall yield of 45%. Considering that bacteriopheophorbide a methyl ester is the precursor of BChlPP, the actual yield improved is five- to ten-fold. The purity of BChlE6-NHS was 99% by RP-HPLC. FIG. 8 shows the HPLC chromatogram and the absorption spectra of this compound.

Synthesis of Photoactivatable Killing Agents—BChl, Pyrophephorbide Acid and Pyrophephorbide Succinimide Ester Synthesis Bacteriochlorophyll (BChl) is known as an excellent photoactivatable killing agent for NIR imaging and photodynamic therapy (PDT), but it is unstable and expensive. In order to establish a optimal protocol for synthesis of the BChl-Car-MB, an inexpensive starting material, pyropheophorbide acid (Pyro), which was prepared from chlorophyll (Chl, the plant counterpart of BChl) extracted from *Spirulina* algae was selected as PS for synthesis of PDT beacon. Pyropheophorbide acid has a distinctive Soret band (380-420 nm) and a Qy band at 664 nm (see FIG. 10a (Solid line). It also has strong emission at 672 nm and good photophysical properties ($^1O_2$ yield: 45%). FIG. 10b showed the absorption spectrum of carotenoid (Car) moieties Methyl pheophorbide a (500 mg, 0.82 mmol) isolated from *Spirulina* algae was heated under refluxed temperature in collidine (100 mL) for 3 h under nitrogen atmosphere. The solution was evaporated under high vacuum, and the residue so obtained was chromatographed over an alumina column (Grade III) and eluted with $CH_2Cl_2$. Pyropheophorbide a methyl ester was crystallized from $CH_2Cl_2$/hexane in 91% yield (411 mg, 0.75 mmol). This intermediate (250 mg, 0.46 mmol) was dissolved in THF (65 mL) and mixed with a solution containing LiOH (500 mg), methanol (7 mL), and water (3 mL). The mixture was stirred under argon atmosphere for 24 h. After workup, the crude product was chromatographed on a silica column with 10% methanol in $CH_2Cl_2$ to give the title compound in 82% yield (200 mg, 0.37 mmol). The spectral and physical data of compound are consistent with the literature. Mp: 220-223° C. UV-vis in $CH_2Cl_2$: 411 nm ($\epsilon$ 1.1×10$^5$), 509 (1.1×10$^4$), 537 (9.6×10$^3$), 611 (8.2×10$^3$), and 669 (4.5×10$^4$). Mass calcd for $C_{33}H_{34}N_4O_3$: 534.5; found by ESI-MS; 535.6 (MH$^+$_) and 557.6 (M+Na$^+$). $^1$H NMR (CDCl$_3$): 9.47, 9.35 and 8.53 (each s, 1H, 5-H, 10-H, and 20-H); 8.00 (dd, J=17.7, 11.4 Hz, 1H, 3$^1$-CH=CH$_2$); 6.27 (d, J=17.7 Hz, 1H, trans-3$^2$-CH=CH$_2$); 6.15 (d, J=11.4 Hz, 1H, cis-3$^2$-CH=CH$_2$); 5.18 (ABX, 2H, 13$^2$-CH$_2$); 4.47 (q, J=7.1, 1.9 Hz, 1H for 18-H); 4.29 (m, J=7.8 Hz, 1H for 17-H); 3.68 (q, J=7.4 Hz, 2H, 8-CH$_2$CH$_3$); 3.64, 3.39, and 3.22 (each s, 3H, 12-CH$_3$, 2-CH$_3$ and 7-CH$_3$); 2.65 and 2.32 (each m, 2H, for 2×17$^1$-H and 2×17$^2$-H); 1.81 (d, J=7.2 Hz, 3H, 18-CH$_3$); 1.70 (t, J=8.3 Hz, 3H, 8-CH$_2$CH$_3$); 0.87 and −1.35 (each brs, 1H, 2×N—H).

Synthesis of Quenchers—Synthesis of Carotenoid Precursors (Car):

The following is a description of efficient synthesis of succinimide ester-containing Carotenoid Precursors (Car), which allows conjugation of Car to oligonucleotide or peptide by coupling of the terminal primary amine group.

Synthesis of Quenchers—Preparation of Diethyl (4-carbomethoxy)benzylphosphonate

Methyl-4(bromomethyl)benzoate (5.00 g, 21.8 mmol) and triethyl phosphate (6.51 g, 39.2 mmol) in toluene (50 mL) were stirred under a stream of argon. The mixture was heated at reflux for 28 h. The solvent was distilled under reduced pressure and the residue was purified by flash chromatography (dichloromethane/gradient methanol, 5%) to afford 5.87 g (94%) of pure phosphonate as determined by NMR spectroscopy. UV $\lambda_{max}$ (dichloromethane) [nm]($\epsilon$ [dm$^3$ mol$^{-1}$ cm$^{-1}$]) 236 (1.75×10$^4$), 270 (1.28×10$^3$). $^1$HNMR (CDCl$_3$, TMS) δ 1.23 (t, 6H, J=7.2 Hz); 3.19 (d, 2H, J=21.9 Hz); 3.90 (s, 3H); 4.02 (q, 4H, J=7.2 Hz); 7.36 (d, 2H, J=8.1 Hz); 7.98 (d, 2H, J=8.1 Hz). $^{13}$CNMR (75.45 MHz, CDCl$_3$, TMS) δ 16.31 (d, Jpocc=5.4 Hz, —CH$_3$); 34.00 (d, Jpc=138.5, —OPCH$_2$—); 52.06 (—OCH$_3$); 62.52 (d, Jpoc=7.6 Hz, —CH$_2$OPO—); 128.78 (1C$_{Ar}$); 129.75 (2CH$_{Ar}$); 129.84 (d, J$_{PCH2CArCAr}$=6.4 Hz, 2CH$_{Ar}$); 137.17 (d, J$_{PCH2CAr}$=8.6 Hz, 1CH$_{Ar}$); 166.88 (—COOCH$_3$). MS [m/z] 286.1 (M$^+$).

Into a 250 mL flask outfitted with a magnetic stirring bar, a condenser, and a gas inlet tube are placed 1.0 g (2.4 mmol) of 8'-apo-β-carotenal, 50 mL of THF 1 g (2.9 mmol) of diethyl (4-carbomethoxy)benzylphosphonate and 0.17 g (3.1 mmol) of sodium methoxide. The suspension was stirred for overnight at room temperature. The crude mixture was neutralized with hydrochloric acid. The solution poured with 500 mL ethyl ether. The ether layer washed with water 5×500 mL, dried over MgSO$_4$ and filtered, the solution is evaporated, and the residue is recrystallized from dichloromethane-methanol.

UV $\lambda_{max}$ (dichloromethane) [nm] ($\epsilon$ [dm$^3$ mol$^{-1}$ cm$^{-1}$]) 236 (1.75×10$^4$), 270 (1.28×10$^3$). $^1$HNMR (CDCl$_3$, TMS) δ 1.23 (t, 6H, J=7.2 Hz); 3.19 (d, 2H, J=21.9 Hz); 3.90 (s, 3H); 4.02 (q, 4H, J=7.2 Hz); 7.36 (d, 2H, J=8.1 Hz); 7.98 (d, 2H, J=8.1 Hz). $^{13}$CNMR (75.45 MHz, CDCl$_3$, TMS) δ 16.31 (d, Jpocc=5.4 Hz, —CH$_3$); 34.00 (d, Jpc=138.5, —OPCH$_2$—); 52.06 (—OCH$_3$); 62.52 (d, Jpoc=7.6 Hz, —CH$_2$OPO—); 128.78 (1C$_{Ar}$); 129.75 (2CH$_{Ar}$); 129.84 (d, J$_{PCH2CArCAr}$=6.4 Hz, 2CH$_{Ar}$); 137.17 (d, J$_{PCH2CAr}$=8.6 Hz, 1CH$_{Ar}$); 166.88 (—COOCH$_3$). MS [m/z] 286.1 (M$^+$).

Synthesis of Quenchers—Carotenide Succinimide Ester

The carotenide acid 100 mg dissolved in 4 mL DMF added into 42.12 mg DCC. The mixture was stirring at room temperature under argon. After 6 hrs. added into N-hydroxysuccinimide 21.5 mg. After 20 hrs. removed DMF. UV $\lambda_{max}$ (dichloromethane) [nm] ($\epsilon$ [dm$^3$ mol$^{-1}$ cm$^{-1}$]) 236 (1.75× 10$^4$), 270 (1.28×10$^3$). $^1$HNMR (CDCl$_3$, TMS) δ 1.23 (t, 6H, J=7.2 Hz); 3.19 (d, 2H, J=21.9 Hz); 3.90 (s, 3H); 4.02 (q, 4H, J=7.2 Hz); 7.36 (d, 2H, J=8.1 Hz); 7.98 (d, 2H, J=8.1 Hz). $^{13}$CNMR (75.45 MHz, CDCl$_3$, TMS) δ 16.31 (d, Jpocc=5.4 Hz, —CH$_3$); 34.00 (d, Jpc=138.5, —OPCH$_2$—); 52.06 (—OCH$_3$); 62.52 (d, Jpoc=7.6 Hz, —CH$_2$OPO—); 128.78 (1C$_{Ar}$); 129.75 (2CH$_{Ar}$); 129.84 (d, J$_{PCH2cArcAr}$=6.4 Hz, 2CH$_{Ar}$); 137.17 (d, J$_{PCH2cAr}$=8.6 Hz, 1CH$_{Ar}$); 166.88 (—COOCH$_3$). MS [m/z] 286.1 (M$^+$).

Synthesis of Conjugates—BChl-Molecular Beacons

After BChl-NCS, model BChl (Pyro-succ) and Car precursors were synthesized in order to construct a BChl-MBs. Pyro acid was used in place of BChl-NCS for a model study (FIG. 13 shows the molecular structure of BChl-MBs).

Synthesis of Conjugates—Method for Synthesis of Model BChl-MBs

By this method, successive synthesis a Pyro-30mer-Car through solid phase reaction (FIG. 14) is performed. The model oligonucleotide (5'-GCGAGTCCCGCCTGTGACATGCATTCTCGC-3'; (SEQ ID NO:21)) includes a 20mer AS-ON sequence identical to ISIS 5132, which is a c-raf kinase AS-ON currently in Phase II study for various cancers, and with two 5mer arm sequences(underlined) at the each end of the sequence which are complementary each other to form stem of MB. Pyro and Car were attached to the end of each arm respectively. FIG. 14 shows the molecular structure of Pyro-30mer-Car.

Synthesis of Conjugates—Pyro—CPG Synthesis

Pyropheophorbide acid (22 mg. 40 umol) was dissolved in 3 mL DMF and activated with HBTU (15.2 mg, 40 umol)/HOBt (5.5 mg, 40 umol) under the presence of argon for 20 min. The intermediate mixture was transferred to the shake flask containing 3'-Amino-Modifier $C_3$ CPG (300 mg, Fmoc loading >25 umol/g, Glen Research) CPG, of which the Fmoc protecting group was removed with 20% piperidine/DMF in advance. After shaking the flask at room temperature for 12 h, the CPG was filtered and washed with DMF (3×5 mL), ACN (3×5 mL) and DCM (3×5 mL) successively to remove unreacted reagents. The CPG was then capped with acetic anhydride/pyridine in THF (10% solution) for 1 h, following by washing with DMF, $CH_3CN$ to afford Pyro modified CPG. MS [m/z] 966.5 ($M^+$).

Synthesis of Conjugates—Pyro-Oligonucleotide-MMT synthesis

On an automatic DNA synthesizer, the first 3'-nucleotide G is covalently attached to the Pyro-modified CPG and successive nucleotide monomers are added one by one through a cycle of four chemical reactions: detritylation, coupling, capping and oxidation. After finishing the DNA sequence synthesis, a 5'-Amino-modifier C3 was anchored to the DNA sequence at the last coupling step to afford Pyro-30mer-MMT. FIG. 16 shows the absorption spectrum of Pyro modified CPG (Green line) and Pyro-30mer (red line), which were cleaved from solid support.

Synthesis of Conjugates—Pyro-Car-Car Synthesis

Activated Car-acid (22.2 mg, 40 umol) was incubated with HBTU (15.2 mg. 40 umol) and HOBt (5.5 mg, 40 umol) in DMF under the presence of argon for 20 min. The intermediate mixture was transferred to a flask containing Pyro-30mer-CPG (8 umol), of which the MMT protect group of the 5'-Amino-modifier was removed by 2.5% TCA in DCM. After shaking overnight at room temperature in the presence of argon, the CPG was filtered and washed with NMF (3×5 mL), DCM (3×5 mL) and MeOH (3×5 mL). The oligonucleotide was cleaved from CPG in ammonium hydroxide at 55° C. for 17 hr and the solution dried followed by purification of the compound by HPLC to produce Pyro-DNA-Car. (HPLC method: Using 0.1M TEAA and $CH_3CN$ as HPLC eluent, from 10% $CH_3CN$ to 90% $CH_3CN$ for 45 min.) FIG. 17 shows the HPLC result and the absorption spectrum of Pyro-30mer-Car (blue line).

Synthesis of Conjugates—Alternative Method for Synthesis of Model BChl-MBs

Using the commercial Pthalimidyl-modified CPG (Trilink-Biotechnologies. Co), oligonucleotide synthesis using an automated DNA synthesizer is performed first. Following synthesis, a 5'-Amino-modifier C3 was anchored to the DNA sequence at the last DNA synthesis step. After removing the MMT protecting group of 5'-Amino-modifier C3, Carotenide acid was conjugated to the DNA sequence with HBTU/HOBt activation. After cleaving this oligonucleotide from CPG and removing Pthalimidyl (Pth) protected group in concentrated ammonium hydroxide at 55 C for 17 h, the Pyro NHS was conjugated to the DNA sequence by solution reaction. Scheme6 showed this synthesis process Synthesis of Conjugates—Pthalimidyl Modified DNA Sequence Synthesis Using an automatic DNA synthesizer, the first 3'-nucleotide G is covalently attached to the Pth-modified CPG and successive nucleotide monomers are added one by one through a cycle of four chemical reactions: detritylation, coupling, capping and oxidation. After finishing the DNA sequence synthesis, a 5'-Amino-modifier C3 was anchored to the DNA sequence at the last coupling step to afford Pth-30 mer-MMT.

Synthesis of Conjugates—Pth-Oligonucleotide-Car Synthesis

Activated Car-acid (22.2 mg, 40 umol) was incubated with HBTU (15.2 mg. 40 umol) and HOBt (5.5 mg, 40 umol) in DMF under the presence of argon for 20 min. This intermediate mixture was transferred to flask containing Pth-30 mer-CPG (8 umol), of which the MMT protect group of the 5'-Amino-modifier was removed by 2.5% TCA in DCM. After shaking overnight at room temperature in the presence of argon, the CPG was filtered and washed with DMF (3×5 mL), DCM (3×5 mL) and MeOH (3×5 mL). The oligonucleotide was cleaved from CPG in ammonium hydroxide at 55° C. for 17 hr and the Pth protected group was removed in this step, and then dried after filtration followed by purifying the compound using HPLC to afford $NH_2$-30 mer-Car. (HPLC method: Using 0.1M TEAA and $CH_3CN$ as HPLC eluent, from 30% $CH_3CN$ to 70% $CH_3CN$ for 45 min.) FIG. 18 shows the HPLC retention time and absorption spectrum of $NH_2$-30 mer-Car.

Synthesis of Conjugates—Pyro-Oligonucleotide-Car Synthesis

The Pyro-NHS was reacted with the $NH_2$-30 mer-Car in DMSO in the presence of DIPEA for 10 hr at room temperature. After HPLC purification, the Pyro-DNA-Car substrate was isolated. FIG. 19 shows the HPLC profile. The reaction yield is more than 40%. (See FIG. 20).

Synthesis of Photoactivatable Killing Agents—BChl, Pyrophephorbide Acid and Pyrophephorbide Succinimide Ester Synthesis Bacteriochlorophyll (BChl) is known as an excellent photoactivatable killing agent for NIR imaging and photodynamic therapy (PDT), but it is unstable and expensive. In order to establish a optimal protocol for synthesis of the BChl-Car-MB, an inexpensive starting material, pyropheophorbide acid (Pyro), which is prepared from chlorophyll (Chl, the plant counterpart of BChl) extracted from *Spirulina* algae is selected as PS for synthesis of PDT beacon. Pyropheophorbide acid has a distinctive Soret band (380-420 nm) and a Qy band at 664 nm (see FIG. 32*a* (Solid line). It also has strong emission at 672 nm and good photophysical properties ($^1O_2$ yield: 45%). FIG. 32*b* shows the absorption spectrum of BHQ moieties.

Methyl pheophorbide a (500 mg, 0.82 mmol) isolated from *Spirulina* algae is heated under refluxed temperature in collidine (100 mL) for 3 h under nitrogen atmosphere. The solution is evaporated under high vacuum, and the residue so obtained is chromatographed over an alumina column (Grade III) and eluted with $CH_2Cl_2$. Pyropheophorbide a methyl ester is crystallized from $CH_2Cl_2$/hexane in 91% yield (411 mg, 0.75 mmol). This intermediate (250 mg, 0.46 mmol) is dissolved in THF (65 mL) and mixed with a solution containing LiOH (500 mg), methanol (7 mL), and water (3 mL). The mixture is stirred under argon atmosphere for 24 h. After workup, the crude product is chromatographed on a silica column with 10% methanol in $CH_2Cl_2$ to give the title compound in 82% yield (200 mg, 0.37 mmol). The spectral and physical data of compound are consistent with the literature. Mp: 220-223° C. UV-vis in $CH_2Cl_2$: 411 nm ($\epsilon$ 1.1×10$^5$), 509 (1.1×10$^4$), 537 (9.6×10$^3$), 611 (8.2×10$^3$), and 669 (4.5×10$^4$). Mass calcd for $C_{33}H_{34}N_4O_3$: 534.5; found by ESI-MS; 535.6 ($MH^+$_) and 557.6 ($M+Na^+$). $^1H$ NMR ($CDCl_3$): 9.47, 9.35 and 8.53 (each s, 1H, 5-H, 10-H, and 20-H); 8.00 (dd, J=17.7, 11.4 Hz, 1H, $3^1$-CH=$CH_2$); 6.27 (d, J=17.7 Hz, 1H, trans-$3^2$-CH=$CH_2$); 6.15 (d, J=11.4 Hz, 1H, cis-32-CH=$CH_2$); 5.18 (ABX, 2H, $13^2$-$CH_2$); 4.47 (q, J=7.1, 1.9 Hz, 1H for 18-H); 4.29 (m, J=7.8 Hz, 1H for 17-H); 3.68 (q, J=7.4 Hz, 2H, 8-$CH_2CH_3$); 3.64, 3.39, and 3.22 (each s, 3H, 12-$CH_3$, 2-$CH_3$ and 7-$CH_3$); 2.65 and 2.32 (each m, 2H, for 2×$17^1$-H and 2×$17^2$-H); 1.81 (d, J=7.2 Hz, 3H, 18-$CH_3$); 1.70 (t, J=8.3 Hz, 3H, 8-$CH_2CH_3$); 0.87 and −1.35 (each brs, 1H, 2×N—H).

Example 2

Preparation of Conjugate with Peptide Substrate

Synthesis of Conjugates—Synthesis of Peptide PDT Beacon

PDT beacons consisting of peptide sequences which can be cleaved by specific enzymes overexpressed in tumor cell were also designed and synthesized.

Synthesis of Conjugates—Synthesis of Model BChl-Peptide PDT Agents:

A cleavable caspase-3 substrate GDEVDGSGK (SEQ ID NO:10; cleavage site underlined) was chosen as the peptide sequence, for which there is a well-established assay for the caspase-3 specific fluorogenic substrate. Based on the same reason as for Bchl-MBs, pyropheophorbide acid was used instead of BChl to synthesize the peptide PDT beacon. FIG. 21 shows this synthesis process.

Synthesis of Conjugates—Synthesis of Caspase-3 cleavable Peptide Sequence

Caspase-3 substrate GDEVDGSGK(Mtt) (SEQ ID NO: 18) with Glycine and lysine at both ends for conjugation was synthesized by manual Fmoc SPPS (solid phase peptide synthesis) protocol using sieber amide resin and O-(Benzotriazole-1-yl)-N,N,N',N'-tetramethyluronium-hexafluorophosphate (HBTU)/1-Hydroxybenzotriazole(HOBt) as the activating reagents. Every step of peptide synthesis was monitored by EMS spectrum and HPLC chromatograph in order to get enough purified peptide sequence (purity is more than 90%, see FIG. 22 HPLC result.).

Synthesis of Conjugates—Synthesis of PS Conjugated Peptide Sequence

Activated Pyro-acid was incubated with HBTU and HOBt in NMP under the presence of argon for 20 min. This intermediate mixture was transferred to a flask containing peptide-resin, of which the Fmoc protected group of the last amino acid (Glycine) was removed by 20% Piperidine in DMF. After shaking overnight at room temperature in the presence of argon, the resin was filtered and washed with NMF (3×5 mL), DCM (3×5 mL) and MeOH (3×5 mL). The peptide was cleaved in Sieber resin in 2% TFA in DCM followed by treatment with a deprotection solution: (30:5:65 TFA/Triisopropylsilane/DCM) for 1 hr. The solution was concentrated and the compound precipitated in ether to produce a green cotton-like solid. The composition of this compound was confirmed by matrix-assisted laser desorption ionization time-of-flight mass spectrometry (MALDI-TOF) Calcd. 1378.49, found 1378.84. The purity is more than 90% from HPLC (see FIG. 23).

Conjugation of Quencher to the PDT Substrate

The Mtt protect group on lysine was removed during the peptide cleavage and deprotection. The Car-NHS was then reacted with the lysine residue of the opposite end of the peptide chain (FIG. 21). Purification of this product was achieved by using two connected Diol and C18 Sep-pak columns and confirmed by matrix-assisted laser desorption ionization time-of-fight mass spectrometry (calculated: 1895.24, actual: 1896.03). The presence of all three structural components in PPC was further confirmed by absorption spectroscopy (FIG. 24C), which shows characteristic peaks of the Pyro (419, 664 nm) and Car (470, 500 nm) moieties.

The Activation of PPC

The PPC was then tested for caspase-3 cleavage using HPLC. As showed in FIG. 25A, addition of caspase-3 clearly induced cleavage, as demonstrated by the diminishing PPC peak at 27 min and the rise of Pyro-peptide (PP) peak at 13 min. The cleavage was proved to be caspase-3-specific by using a caspase-3-specific inhibitor (Ac-DEVD-CHO) that completely blocked the enzyme activity. Another observation is that the caspase-3 cleavage of PPC also led to two to three fold fluorescence enhancement, indicating that, in addition to $^1O_2$ quenching, Car is capable of quenching Pyro fluorescence to some extent. This could allow these agents to serve both as directed-PDT and tumor-specific diagnostic agents.

To test this concept, $^1O_2$ was measured directly in solutions of PPC alone, PPC incubated with caspase-3 and PPC incubated with caspase-3 plus a caspase-3 inhibitor. PP alone, without the Car moiety, was used as a positive control. $^1O_2$ generation was quantified by measuring its near-infrared (NIR) luminescence at 1270 nm. Briefly, a 10 ns pulsed 532 nm laser excites the solution and the luminescence spectrum is sampled using a set of interference filters and a high-sensitivity NIR photomultiplier tube operating in time-resolved single photon counting mode, after rejection of PS fluorescence.

As shown in FIGS. 25B and 25C, addition of caspase-3 to the PPC (molar ratio: 1:60; incubation time: 1 hour) resulted in a four-fold increase in $^1O_2$ signal, an effect that was completely reversed by co-incubation with the caspase-3 inhibitor (8×PPC concentration with the same incubation time). As expected, the $^1O_2$ generation by PP was unaffected by caspase-3 or its inhibitor. The two-fold difference in luminescence between the PP and PPC+caspase-3 was related to a corresponding decrease in the $^1O_2$ lifetime, probably due to the presence of free CAR quenchers in solution after cleavage. The difference in $^1O_2$ luminescence between PPC alone and PPC+caspase-3 is likely due to both photoactivatable killing agent triplet-state and $^1O_2$ quenching by CAR. Hence, these data demonstrate that $^1O_2$ generation is effectively inhibited by the CAR quencher and that caspase-3-induced separation of the quencher and the photoactivatable killing agent molecules allows photoactivation of the latter. All of the above experiments were repeated at least in triplicate and were statistically significant (p<0.04).

Example 3

Delivery of Conjugate with Nucleic Acid Substrate

Determination of the Hybridization Efficiency in Solution

It will be demonstrated that a model BChl-MB can hybridize with a ssDNA (5'-AATGCATGTCACAGGCGGGA-3'; SEQ ID NO:21) that is complementary to the loop sequence of MB. Because detection sensitivity for $^1O_2$ is much lower than the sensitivity of fluorescence, it the hybridization efficiency will first be determined by spectrofluorimetry. Thus, the model BChl-MB or control MBs will be added to an excess (5-10 fold) of complementary target DNA. The efficiency of energy transfer between the BChl and the Car will be determined by quantifying the fluorescence intensity of the BChl at 840 nm using the excitation wavelength of 825 nm.

Determination of the Hybridization Efficiency in Solution—Delivery of BChl-MBs to Cells Expressing Target mRNA Since the majority of mRNA is located in the cytoplasm instead of the nucleus, it is desirable to deliver MBs to the intracellular compartments (preferably cytosol). Accordingly, efficient delivery of the BChl-MBs to the target cells will be accomplished. First, transfection with cationic lipids such as Lipofectamine will be used because they are the most widely used vehicles for in vitro AS-ON delivery. These cationic lipids are positively charged molecules that bind negatively charged ONs through electrostatic interactions. Then, transport-enhancing peptides will be utilized to improve cytoplasmic delivery. Several peptides including ANT, a 16 amino acid sequence from Drosophila antennapedia protein, are actually transported across the cellular membrane and localize in the cytoplasm. During intracellular delivery, nuclease mediated degradation of BChl-MBs may occur. Accordingly, BChl-MBs can be constructed using thiolated AS-ONs, since these thiolated AS-ONs are less susceptible to nuclease degradation.

Determination of the Hybridization Efficiency in Solution—Transfection of BChl-MBs with Lipofectamine Lipofectamine 2000 (LF2000), a reagent from Invitrogen Corp. (Carlsbad, Calif.), is suitable for the transfection of nucleic acids into eukaryotic cells. BChl-MB-LF2000 complexes are prepared following standard protocols and are added directly to cells in culture medium. Three cell lines will be studied. For model BChl-MBs targeting c-raf-1 mRNA, the MDA-MB-231 breast cancer cell line will be used. For EGFRvIII mRNA targeting BChl-MBs, HC20 cells (EGFRvIII positive) and C012 cells (EGFRvIII negative) both derived from NIH-3T3 cells, will be provided be used. The efficiency of intracellular delivery of BChl-MBs will be determined by fluorescence confocol microscopic study.

Determination of the Hybridization Efficiency in Solution—Transport-Enhancing Peptides BChl-MBs will be synthesized with ANT peptide sequence incorporated via an S—S linkage into the 5'-end of the MB to serve as an intracellular delivery vehicle (see Scheme 2), with the assumption that its disulfide bond will be cleaved before the MB enters the nucleus, thus achieving the cytosol delivery.

Determination of the Hybridization Efficiency in Solution—$^1O_2$ Measurement in Solution and in Cells In Vitro Because of the strongly decreased lifetime of $^1O_2$ in cells and tissues caused by rapid quenching by biomolecules, a reliable $^1O_2$ measurement assay in cells has not been available until recently. A system based on a high-sensitivity NIR photomultiplier tube, with corresponding light activation and detection protocols for measuring $^1O_2$ luminescence in cells in vitro and in tissues in vivo has been developed (Dr. Brian Wilson; Consortium Investigator, University of Toronto). This system will be available to measure 102 generation, not only in solution but also in tumor cells in vitro and subsequently tumors in vivo. PDT generation of 102 will be made for the model BChl-MB upon hybridization with corresponding targets.

Determination of the Hybridization Efficiency in Solution—Identify Suitable Loop Using MB Probes and Computer Programs Hybridization to total RNA extracted from EGFRvIII mRNA expressing HC20 cells will be performed using standard procedures. Total mRNA will be extracted by following Chomczynski and Sacchi' single step extraction method. RNA (3 µg) will be heated to 95° C. for 5 minutes, then hybridized to MB probes. After hybridization overnight at 37° C., 0.6 ml of Tris buffer containing 1 mM $MgCl_2$ will be added and samples will be centrifuged for 20 minutes to remove particulate matter. Emission spectra will be scanned with a fluorimeter as described above. Detection of a strong fluorescence signal only when MBs were placed in solution with the ON target to which they could hybridize is expected. Thus, the desired loop sequence for proposed breast cancer-specific BChl-MB, EGFRvIII AS, will be defined. In addition, computer programs ("MFOLD" or "foldsplit") that calculate the local folding potential for a given mRNA sequence will be used to facilitate the mapping process. Once adequate EGFRvIII mRNA targets have been identified the desired EGFRvIII AS loop containing BChl-MBs will be synthesized using the methods described above. BChl-MBs will be delivered into HC20 cells (EGFRvIII positive) and C012 cells (EGFRvIII negative) following LF2000 transfection. Once the MB is delivered to its subcellular target, the hybridization process between BChl-MB and the target mRNA occurs and enables the $^1O_2$ production. This process will be confirmed by the direct $^1O_2$ detection assay as described above.

The lifetime of BChl-MB/EGFRvII mRNA hybrid depends on factors such as RNase-H activity. If this hybrid is cleaved by RNase-H, BChl-MB returns to its hairpin form and the $^1O_2$ is quenched. In other words, the therapeutic window for the PDT treatment no longer exists. Therefore, this study will determine the optimum PDT treatment time in vitro. Thus, BChl-MBs will be first incubated with HC20 cells and suitable delivery vehicles. For multiple time points during incubation, cells will be collected to measure MB uptake by spectrofluorimetry. The time point of highest fluorescence will be identified and used. Measurements at the same time points in C012 cells will be used to determine when fluorescence begins to appear in this cell line. This will be used as an indication of when degradation of the MB begins to occur.

In Vitro Determination of the Photodynamic Efficacy and Selectivity of BChl-MB PDT These experiments test the utility of the EGFRvIII mRNA triggered BChl-MB PDT to treat breast cancer. A BChl-MB construct that exhibits selective photosensitization of its target cells when hybridization has taken place will be identified.

To determine the ability of BChl-MB to photosensitize cells expressing EGFRvIII mRNA, the clonogenic survival of BChl-MB PDT-treated HC20 cells will be compared with the survival of C012 cells subjected to the same PDT protocol. Thus cells will be exposed to the BChl-MB and delivery vehicle for the incubation time required for maximum binding of BChl-MB as described above. Following this incubation, the BChl-MB-containing media will be removed, and cells will be rinsed in HBSS, trypsinized to detach them from the plate and illuminated in suspension. PDT will be carried out with a diode laser emitting at 830±10 nm. The light dose rate will be measured using an isotropic detector based light dosimetry system. Immediately after illumination, cells will be plated at concentrations from $10^2$-$10^6$ cells/100 mm dish in their standard growth media and incubated in 5% $CO_2$ until colony formation. For each cell line, survival curves will be created as a function of "equivalent drug dose" and survival parameters will be determined and statistically compared using the JMP software (SAS Institute, Inc., NC).

The expected results are an effective PDT response to BChl-MB in the EGFRvIII-expressing cell line, with no response in the non-expressing cells. If (non-EGFRvIII dependent) cell kill is found in C012 cells, the enhancement of kill in the HC20 line will be quantified as the ratio of the drug or light dose required to produce a 90% reduction in the surviving fraction of C012 cells to HC20 cells.

The specificity of BChl-MB PDT is provided by the precise targeting of BChl-MB to the EGFRvIII mRNA and the necessity for drug binding for $^1O_2$ production to take place. Survival curves will be performed as described above, with the exception that after detachment from the plate cells, the cells will be resuspended in the photoactivatable killing agent-containing media for illumination. In parallel studies, PDT will be carried out with an equivalent dose of free BChl, also with illumination taking place in the presence of the photoactivatable killing agent. Survival curves will be determined to compare the change in survival when illumination is performed in the presence versus absence of BChl-MB and when illumination is performed in the presence versus absence of free BChl. Cells illuminated in the absence of drug will be exposed to drug during incubation but the drug containing media will be removed before light exposure. Results will be quantified as the ratio of the dose (drug or light) necessary to create a 90% reduction in clonogenicity for illumination in the absence of drug to the dose required for illumination in the presence of drug.

The expected results are a decrease in clonogenicity when PDT is performed in the presence of free BChl compared to illumination in the absence of free BChl.

Example 4

Preparation of a Conjugate with PSA-Cleavable Substrate

Synthesis of a PSA-Cleavable Photodynamic Therapy (PDT) Agent with a HSSKLQ-Containing Peptide Sequence, a Pyropheophorbide (Pyro) Photoactivatable Killing Agent (PS), and a Singlet Oxygen ($^1O_2$) Quencher/Scavenger (Q).

The most important requirement for a desired PSA-specific substrate is the efficient cleavage by PSA. It has been shown that doxorubicin can be coupled directly to the Ac-HSSKLQ (SEQ ID NO:13) peptide to form the prodrug Ac-HSSKLQ (SEQ ID NO:13)-Dox. Using HPLC detection, it was determined that PSA was unable to hydrolyze the amide bond between the doxorubicin amine and the C-terminal glutamine of the peptide. On the other hand, incubation of the Mu-HSSKLQ(SEQ ID NO:13)-Leu-Dox prodrug (Mu=morpholinocarbonyl) with enzymatically active PSA resulted in production of Leu-Dox demonstrating that the steric hindrance introduced by the bulky doxorubicin is a major factor to prevent the PSA-induced peptide cleavage. In the latter construct, Mu was chosen as the $NH_2$ terminal blocking group because of its stability and to enhance substrate solubility. Since both Pyro photoactivatable killing agent and CAR quencher are both large molecules (molecular weight ~600) with rigid structures comparing with Mu (molecular weight 115), a Pyro-GGHSSKLQGSGK-CAR PDT (SEQ ID NO:14) beacon containing a 12 amino acid sequence is proposed. The rationale of this design is as follows: 1) CAR is acid-labile, thus it should be coupled to the peptide in the final conjugation in solution; 2) A C-terminal lysine residue is required for CAR conjugation; 3) The increasing number of glycine residues on both side of the PSA-specific sequence is to compensate the steric hindrance of Pyro and CAR moiety to allow a better folding scaffold for maximizing the interaction between the PS and Q; 4) The inclusion of serine residue is to enhance the substrate solubility to compensate the increase in hydrophobicity introduced by Pyro and CAR moieties.

Peptide PDT Beacon Synthesis

The proposed synthetic pathway for Pyro-GGHSSKLQGSGK-CAR(PPC) (SEQ ID NO:14) PDT beacon is depicted in FIG. 27. Briefly, GGHSSKLQGSGK peptide (SEQ ID NO:14) will be first synthesized using a manual solid phase peptide synthesis (SPPS) protocol. Next, Pyro will be coupled to the N-terminal glycine on the solid-support. The Pyro-peptide conjugate is then cleaved from the support and deprotected. The final CAR conjugation is carried out in solution, since it is acid-labile. Another key challenge of this method is how to distinguish two lysine residues allowing CAR moiety linked to the C-terminal lysine. Therefore, an ivpde group will be used to protect the amino function of the lysine residue in the middle of the sequence, which is cleavable under a very mild condition (2% hydrazine, 5-10 minutes).

Confirmation of Cleavage of Peptide PDT by PSA

Kinetic analysis of PSA hydrolysis will be assayed by HPLC. In brief, various concentration of the beacon will be incubated in PSA buffer with enzymatically active PSA derived from human seminal plasma (CHEMICON, Canada) at room temperature. A control in PSA buffer alone will also be carried out. At discrete time points (1, 2, 4, 8 and 12 hours), aliquots of the reaction mixture are removed and analyzed by a reverse-phase HPLC (Waters, Mass.) equipped with a photodiode array detector and fluorescence detector. A standard curve produced by using purified free Pyro-GGHSSKLQ (SEQ ID NO:15) peptide (PP) will be used to convert peak area to free PP concentration. Peak areas of free PP at each time point will then be converted to concentration, and the concentration data will be analyzed by Lineweaver-Burke plots (1/V versus 1/S, where V=reaction velocity and S=substrate concentration). $K_m$, $V_{max}$ and $K_{cat}$ will be calculated from these plots, and the ratio of $K_{cat}$ to $K_m$ will be used to compare hydrolysis of the PDT beacon with hydrolysis of the reported fluorogenic PSA substrate Mu-HSSKLQ-AMC (SEQ ID NO:13), where AMC is 7-amino-4-methyl coumarin (Voigt Global, Missouri).

Determination of the PSA Cleavage of PDT Beacon in Cell Culture.

To test PPF accumulation in cells, confocal microscopy was measured in human hepatoblastoma G2 (HepG2) cells. As shown in FIG. 28, cells alone have no fluorescence background, whereas cells incubated with 200 µM PPF for 30 min clearly show fluorescence for both Pyro (excited at 633 nm) and FITC (excited at 488 nm). The fluorescence signals in cells grow stronger with longer incubation time (24 h). These images suggest that this kind of beacon construct can enter the cell directly without any additional delivery vehicle.

Conditioned medium from LNCaP cells containing the PDT beacon will be applied to a C18 reverse-phase Bond-Elut column (Varian, Calif.) and washed with buffer for six column volumes consisting of 0.1 M phosphoric acid and 5% acetonitrile in PBS. Samples will be eluted from the column using a solution of 70% acetonitrile/0.1% TFA (v/v). The solvents will then be evaporated to dryness, and the samples will be redissolved in 0.1% TFA (v/v) and applied to reverse-phase HPLC as described above.

Bioluminescence Imaging of the Efficacy of PDT Agent in PSA-Producing Versus Non-Producing Cells To determine the ability of Pyro-peptide-CAR (PPC) PDT beacon to photosensitize cells producing PSA, the clonogenic survival of PPC PDT-treated isolated LNCaP cells (PSA positive) will be compared with the survival of PC3 prostate cancer cells (PSA negative) subjected to the same PDT protocol. Meanwhile, Pyro-peptide (PP) will be served as the positive control. Both prostate cancer cell lines can been stably transduced, and contain endogenous wt p53 protein with a Firefly luciferase gene together with a *Renilla luciferase* gene. Thus, Xenogen IVIS bioluminescence imager will be used to monitor the p53 activity together with the physiological state of the cells, which serve as a reliable indicator of PDT efficacy of the proposed PDT beacon. In brief, following the incubation, the PPC-containing media will be removed, and cells will be rinsed in HBSS, trypsinized to detach them from the plate and illuminated in suspension. PDT will be carried out with a laser emitting at 670 nm. The light dose rate will be measured using an isotropic detector based light dosimetry system. Immediately after illumination cells will be plated at concentrations from $10^2$-$10^6$ cells/100 mm dish in their standard growth media and incubated in 5% $CO_2$ until colony formation. For PSA-producing LNCaP cells, the expected results are the increase of p53 transcription activity determined by Firefly luciferase bioluminescence imaging and the cell death observed by *Renilla luciferase* bioluminescence. For PSA non-producing PC3 cells, an opposite observation is expected.

Bioluminescence Imaging of the Efficacy of PDT Beacon in PSA-Producing Versus Non-Producing Tumor Xenografts Since bioluminescence imaging is at its best for real-time, non-invasive live small animal imaging, changes in tumor volume will be monitored by *Renilla luciferase* luminescence as well as changes in p53-dependent transcriptional activity by Firefly luciferase luminescence in mice following in vivo PDT treatment. The expected results are the tumor shrinkage and the increased p53 activity in PSA-producing LNCaP xenograft model observed through *Renilla* and Firefly luciferase, respectively, whereas none of these should change significantly in the PSA non-producing PC3 xenograft model.

Example 5

Preparation of Conjugates with Death Sensor

Enzyme-Activated PDT Agent with a Built-In Cell Death Sensor (Bifunctional Smart PDT Agents)

Figure 3:
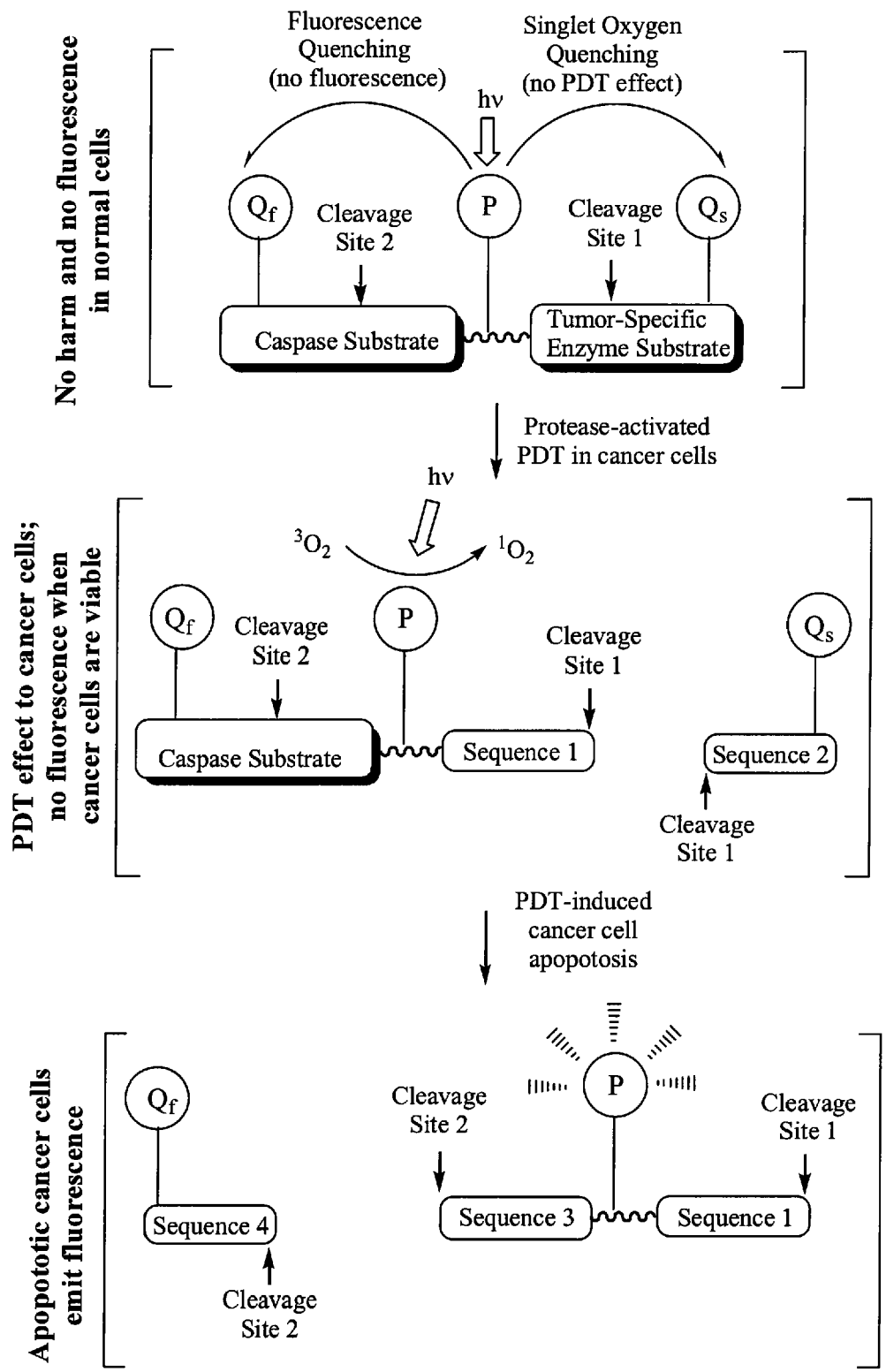
FIG. 3 depicts a conjugate further comprising a death sensor.
Figure 4:
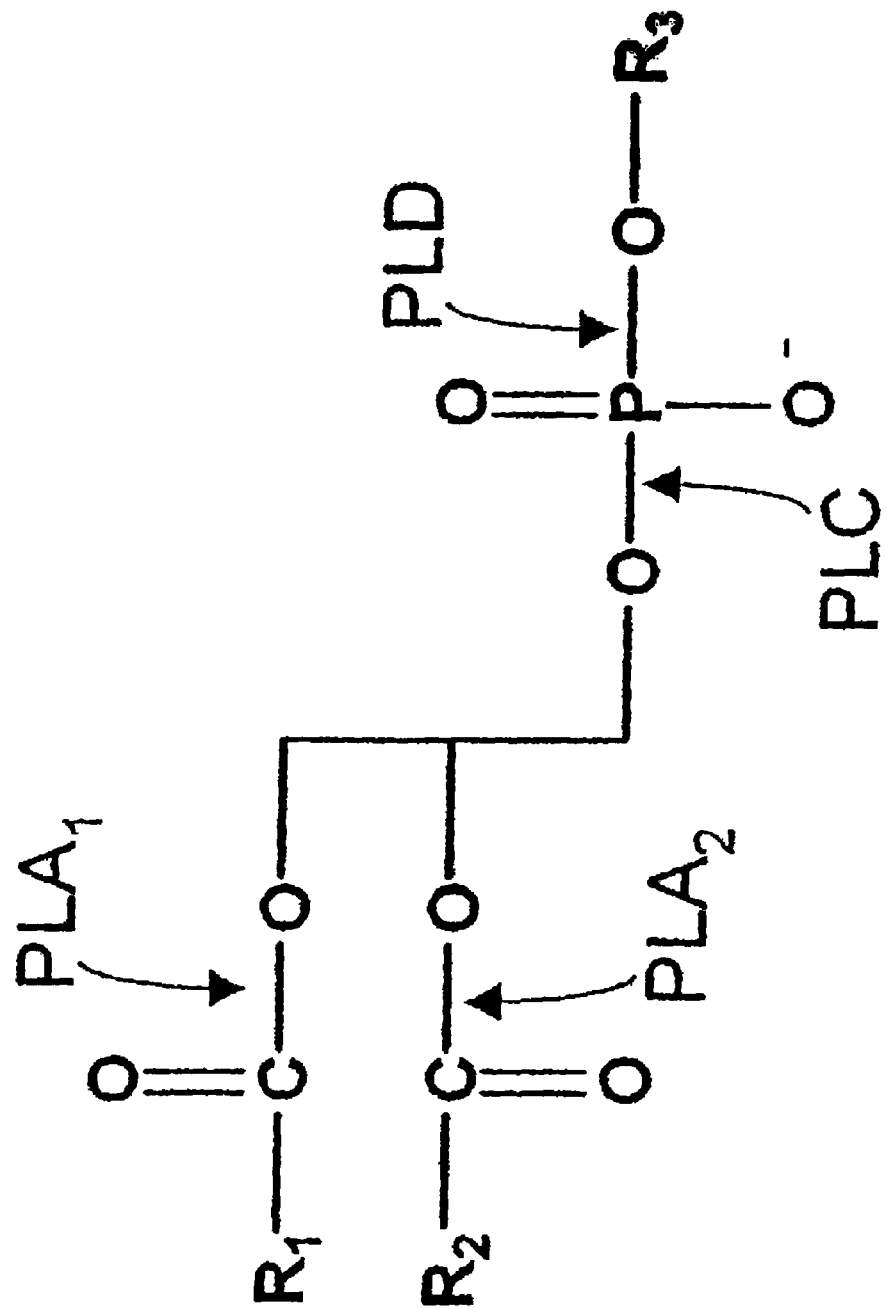
FIG. 4 illustrates the categories of phospholipases, categorized as A1, A2, C and D based on their site of cleavage of a phospholipid.

The concept underlying this invention is depicted in FIG. 3. In general, these new "smart" PDT agents should have following characteristics:

1) they will contain a PDT agent (P) that can both can generate singlet oxygen and emit fluorescence upon light activation 2) they will also contain two substrate sequences, the cell death protease recognition sequence will be a cell death marker, for example, a well known apoptosis marker. Accordingly, a cell death protease recognition sequence such as a caspase substrate, (for: caspase-1, caspase-3, caspase-9, etc.) will be used, and the substrate will be a tumor-specific substrate including but not limited to, peptides, nucleic acids and synthetic polymers, which can be specifically cleaved by certain enzymes;

3) these agents will place P between the two sequences described above; a singlet oxygen quencher (Qs) will be attached to the terminal end of the tumor-specific substrate and a fluorescence quencher (Qf) will be attached to the terminal of the caspase substrate; and 4) both P and Qs and P and Qf are held in proximity by the appropriate length of the substrate sequence. Therefore, when both sequences are intact, Qs quenches the singlet oxygen produced by P and Qs quenches the fluorescence of P. Thus, PDT treatment will not harm normal cells, and no fluorescence signal will be observed.

However, when these agents enter cancer cells, the tumor-specific substrate will undergo a change of conformation such that Qs will be removed from the immediate vicinity of P. In certain embodiments the change of conformation is cleavage of the tumor-specific substrate. Upon photoradiation (i.e., PDT treatment), P will generate singlet oxygen, which will kill the cancer cells. Moreover, if the PDT treatment is effective, apoptosis is expected to occur within the cancer cells; this process will produce caspases. These enzymes will cleave the sequence between P and Qf, and once Qf is removed from the immediate vicinity of P, the quenched fluorescence will be restored. If the PDT treatment is ineffective, there would be no apoptosis. Thus, there would be no caspase activity and the caspase substrate would remain intact, and no fluorescence would be observed. Through this design, not only will the PDT agent be activated exclusively in cancer cells leaving normal cells unharmed, but the effectiveness of such smart PDT agents would also be monitored noninvasively in vivo in real time, providing an immediate monitoring of therapeutic outcome.

Tumor-Specific Enzyme Substrate

Prostate-specific antigen (PSA) is a serine protease secreted by both normal prostate glandular cells and prostate cancer cells. It is found in high concentration in the seminal plasma, where the major proteolytic substrates for PSA are the gel-forming proteins in freshly ejaculated semen, SgI and SgII. On the basis of the PSA cleavage map for SgI and II, a peptide with the amino acid sequence His-Ser-Ser-Lys-Leu-Gln (HSSKLQ; SEQ ID NO:13) was identified by Isaacs et al, that had a high degree of specificity for PSA. This substrate is used to demonstrate that prostate cancer cells secrete enzymatically active PSA into the extracellular fluid and that PSA becomes inactivated by serum protease inhibitors on entering the blood. On the basis of this information, others developed a PSA-activated doxorubicin prodrug (HSSKLQ-Leu-Dox, L-377202, Merck; SEQ ID NO:13) that is inactive when given systemically but becomes activated when processed proteolytically within prostate cancer metastases by PSA. Therefore, this PSA substrate, HSSKLQ peptide (SEQ ID NO:13), is chosen to build a "smart" PDT agents targeting prostate cancer.

Caspase Substrate

Recognition of the central role of caspases in the programmed cell death process (apoptosis) has led to the development of assays that can measure these important enzymes in situ. Caspase activation represents one of the earliest known markers for the onset of apoptosis. In most instances, caspase activation precedes cell permeability alterations and DNA damage, whereas cytoskeletal collapse and phosphatidylserine (PS) flipping are often more concurrent. Loss of mitochondrial membrane generally occurs prior to caspase activation. Several fluorogenic assays have been developed for in situ analysis of caspase activation in intact cells. These assays are useful for detecting localized caspase activation in early apoptotic cells. Among these assays, caspase-3 fluorogenic substrates with the common DEVD (SEQ ID NO: 7) cleavage site are the most widely utilized markers for identifying the early critical onset of cancer cell apoptosis. Therefore, this enzyme substrate, DEVD (SEQ ID NO: 7) peptide, is chosen to integrate a cell death sensor into a "smart" PDT agent to monitor the effectiveness of the agents in real time.

The structure of the first construct for this concept is depicted in FIG. 25. It contains a pyropheophorbide (Pyro) as P, a carotenoid (Car) as Qs, a black hole quencher (BHQ) as Qf, with a PSA substrate between P and $Q_s$ and a caspase-3 substrate between P and $Q_f$. This conjugate is named BHQ-GDEVDSGK(Pyro)HSSKLQK-Car (GDEVDSGKHSSKLQK is SEQ ID NO:16).

Example 6

Preparation of Conjugate with Phospholipid as Substrate

A $PLA_2$-specific phospholipid probe is synthesized incorporating both the quencher (e.g., carotenoid (Car)) and the PDT agent (e.g., Pyro) into the sn-1 and sn-2 portion of the phospholipid, respectively. This design makes the release of the fluorescent moiety independent of cleavage by PLC and PLD. Furthermore, in order to have the $PLA_2$ specificity, the quencher is introduced into the sn-1 position via an ether linkage, since the ether linkage is resistant to $PLA_1$ and it is well known that ether-linked phospholipids also serve as substrates in phospholipase C- or D-catalyzed reactions. Thus, O-alkylation of sn-glycero-3-phosphocholine with N-Boc-ethylenebromide in the presence of a cesium catalyst gives a mixture of mono-sn-1, mono-sn-2 and bis-conjugate, which is separated by HPLC. The sn-2 resulting intermediate will be coupled to the Pyro in the presence of DCC and DMAP. After treating with trifluoroacetic acid (TFA) to remove the Boc protection group, the amino group at the sn-1 position is conjugated to the quencher. The resulting phospholipid, thus, is PLA2-specific.

Example 7

Preparation of Conjugate with Peptide Cell Death Protease Recognition Sequence

Synthesis of Conjugates—Synthesis of Caspase-3 Cleavable Peptide Sequence

Caspase-3 cell death protease recognition sequence KGDEVDGSGK(Mtt) (SEQ ID NO: 11) with lysine at both ends for conjugation is used to synthesize the protected peptide Fmoc-K(Boc)GD(O-2PhiPPr)E(O-2PhiPPr)VD(O-2PhiPPr)GS(Trt)GK(Mtt) by manual Fmoc SPPS (solid phase peptide synthesis) protocol using Sieber amide resin and O-(Benzotriazole-1-yl)-N,N,N',N'-tetramethyluronium-hexafluorophosphate (HBTU)/1-Hydroxybenzotriazole (HOBt) as the activating reagents. Every step of peptide synthesis is monitored by EMS spectrum and HPLC chromatograph in order to get enough purified peptide sequence (purity is more than 95%). The protecting groups are cleavable by mild acidic conditions (3% TFA), with exception of N-terminal Lys, that is protected by a group cleavable by 50% TFA (Boc).

Synthesis of Conjugates—Synthesis of PS Conjugated Peptide Sequence

Following Fmoc cleavage, the photoactivatable killing agent (Pyro-acid) is coupled to the N-terminal Lys (to the α amine) of the peptide. Activated Pyro-acid is incubated with HBTU and HOBt in NMP under the presence of argon for 20 min. This intermediate mixture is transferred to a flask containing peptide-resin, of which the Fmoc protected group of the last amino acid (Lysine) is removed by 20% Piperidine in DMF. After shaking overnight at room temperature in the presence of argon, the resin is filtered and washed with NMP (3×5 mL), DCM (3×5 mL) and MeOH (3×5 mL). The resulting peptide is called Pyro-K(Boc)GD(O-2PhiPPr)E(O-2PhiPPr)VD(O-2PhiPPr)GS(Trt)GK(Mtt). The peptide is cleaved from Sieber resin in 3% TFA in DCM (see FIG. 35A).

Conjugation of Quencher to the PDT Cell Death Protease Recognition Sequence

The fluorescence quencher BHQ-3-NHS is then coupled to the ε-NH$_2$ of C-terminal Lys of Pyro-K(Boc)GDEVDGSGK (SEQ ID NO: 11). The Mtt protected group on lysine is removed during the peptide cleavage and deprotection. The fluorescence quencher BHQ-3-NHS is then coupled to the ε-NH$_2$ of C-terminal Lys of Pyro-K(Boc)GDEVDGSGK (SEQ ID NO: 11) with (1.2:1 ratio) in the presence of 0.5% diisopropylethylamine (DIPEA) as a weak base to form Pyro-K(Boc)GDEVDGSGK(SEQ ID NO: 11)-BHQ. After a 2 hour reaction the Pyro-K(Boc)GDEVDGSGK(SEQ ID NO: 11)-BHQ is precipitated by ether to eliminate the redundant BHQ-3. The structure is then confirmed by analytical HPLC (UV-Vis and fluorescence) and MALDI-ToF. (see FIG. 35B).

Conjugation of Targeting Ligand to the PDT Cell Death Protease Recognition Sequence To couple folate, the Boc deprotecting group of the N-terminal Lys is cleaved by 50% TFA/DCM for 30 minutes. The product is precipitated with dry ether and without further purification, folate-NHS is coupled to the ε-NH$_2$ of N-terminal Lys of Pyro-KGDEVDGSGK(SEQ ID NO: 11)-BHQ (see FIG. 35C). This compound is purified first by Sephadex and than by HPLC (eluents: A=0.1M TEAA (pH 7.4), B=acetonitrile; method: 90% of A and 10% of B to 100% of B in 45 min), dried on speedvac and high vacuum and stored at −20° C. (see FIG. 35D).

Example 8

Cell Lines and Mice

Cell Lines

KB cells (human nasopharyngeal epidermoid carcinoma cells, folate receptor positive) and HT-1080 cells (human fibrosarcoma cells, folate receptor negative) are purchased from the American Type Tissue Collection (Manassas, Va., USA). Both KB and HT-1080 cells are cultured in Eagle's Minimum Essential Medium (MEM) supplemented with 2 mM L-glutamine, 17.9 mM sodium bicarbonate, 0.1 mM non-essential amino acids, 1.0 mM sodium pyruvate, and 10% fetal bovine serum (FBS). All cells are grown at 37° C. in a humidified atmosphere containing 5% $CO_2$.

Animal Preparation

To induce solid tumors, $10^6$ KB or HT1080 cells are injected subcutaneously into mammary fat pads in the lower abdomen of nude mice (average weight 20 g). A single tumor is grown in each mouse and is examined or treated when it reached 5-7 mm in diameter (intermediate size). For dual tumor imaging and PDT experiments, mice are injected with KB and HT1080 cells on the ipsilateral and contralateral side, respectively.

Example 9

In Vivo PDT and Fluorescence Imaging Protocol

The conjugate is injected intravenously into the tail vein. The drug dose is 80 nmol/mouse in 100 µl volume (0.02% DIPEA/5% DMSO/water). The animals treated by PDT are exposed to the laser light tuned to 670 nm with light dose of 150 J/cm$^2$ and fluence rate of 75 mW/cm$^2$. In vivo whole body fluorescence imaging is performed on the Xenogen IVIS imager with Cy5.5 filter (ex. 615-665 nm, em. 695-770 nm) using following settings: stage B, small Bin, fstop/2, lamp high level, 1 sec (FIG. 33).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A conjugate comprising a substrate that comprises a recognition sequence cleavable by proteolytic enzyme, a photoactivatable killing agent, and a quencher, wherein said photoactivatable killing agent is operably linked to one end of said substrate and said quencher is operably linked to another end of said substrate, wherein said proteolytic enzyme is capable of recognizing said recognition sequence in said substrate, wherein said conjugate is capable of providing an intact form and a cleaved form, wherein in said conjugate in said intact form, the distance between said photoactivatable killing agent and said quencher is sufficient for said quencher to quench photoactivation of said photoactivatable killing agent; and wherein in said conjugate in said cleaved form, said photoactivatable killing agent is separated from said quencher as a result of said enzyme contacting said substrate for a period of time and conditions sufficient to proteolytically cleave said recognition sequence, thereby said photoactivatable killing agent is not quenched by said quencher.

2. A conjugate comprising:

(a) a cell death protease recognition sequence;

(b) a photoactivatable killing agent comprising a fluorophore;

(c) a fluorescence quencher; and (d) a targeting ligand;

wherein the photoactivatable killing agent, the fluorescence quencher, and the targeting ligand are covalently linked to the cell death protease recognition sequence, and wherein said cell death protease recognition sequence brings said photoactivatable killing agent and said fluorescence quencher sufficiently close to each other to provide in the conjugate fluorescence quenching of the fluorophore.

3. The conjugate of claim 1, wherein said enzyme is a protease.

4. The conjugate of claim 1, wherein said photoactivatable killing agent is a free base or metal complex of a compound selected from the group consisting of a pyropheophorbide, a purpurin, a porphyrin, a chlorin, a bacteriochlorin, a phthalocyanine, a naphthalocyanine, a hypericin, a porphyrin isomer, an expanded porphyrin, a cationic dye, a psoralen, and a merocyanine 540.

5. The conjugate of claim 1, wherein said quencher is a carotenoid, a metal complex dye, a cyanine dye, a stilbene quinone dye, an azomethine dye, an amine, a phenol, a sulfide, a bilirubin, a biliverdin, a nitroso compound, a nitrone compound and a N-oxy compound.

6. The conjugate of claim 1, wherein said recognition sequence is a cell death protease recognition sequence.

7. The conjugate of claim 6, wherein said cell death protease recognition sequence is cleavable by a caspase.

8. The conjugate of claim 6, wherein said cell death caspase is selected from the group consisting of caspase-1, caspase-2, caspase-3, caspase-4, caspase-5, caspase-6, caspase-7, caspase-8, caspase-9, and caspase-10.

9. The conjugate of claim 6, wherein said cell death protease recognition sequence comprises a sequence selected from the group consisting of Asp-Glu-Val-Ile(SEQ ID NO:1), Asp-Glu-Thr-Asp(SEQ ID NO:2), Leu-Glu-His-Asp(SEQ ID NO:3), Asp-Glu-His-Asp(SEQ ID NO:4), Trp-Glu-His-Asp(SEQ ID NO:5), Leu-Glu-Thr-Asp(SEQ ID NO:6), Asp-Glu-Val-Asp(SEQ ID NO:7), Val-Glu-His-Asp(SEQ ID NO:8), Ile-Glu-Ala-Asp(SEQ ID NO:9); Gly-Asp-Glu-Val-Asp-Gly-Ser-Gly-Lys (SEQ ID NO:10); and Lys-Gly-Asp-Glu-Val-Asp-Gly-Ser-Gly-Lys (SEQ ID NO:11).

10. The conjugate of claim 9, wherein said cell death protease recognition sequence comprises a sequence selected from the group consisting of X-Asp-Glu-Val-Ile(SEQ ID NO: 23)-Y, X-Asp-Glu-Thr-Asp(SEQ ID NO: 24)-Y, X-Leu-Glu-His-Asp(SEQ ID NO: 25)-Y, X-Asp-Glu-His-Asp(SEQ ID NO: 26)-Y, X-Trp-Glu-His-Asp(SEQ ID NO: 27)-Y, X-Leu-Glu-Thr-Asp(SEQ ID NO: 28)-Y, X-Asp-Glu-Val-Asp(SEQ ID NO: 29)-Y, X-Val-Glu-His-Asp(SEQ ID NO: 30)-Y, and X-Ile-Glu-Ala-Asp(SEQ ID NO: 31)-Y, wherein X and Y are each independently a polypeptide comprising from one to about 15 amino acids and the N-terminal amino acid of X is covalently linked to said substrate.

11. The conjugate of claim 9, wherein said cell death protease recognition sequence comprises a sequence selected from the group consisting of X-Asp-Glu-Val-Ile(SEQ ID NO: 23)-Y, X-Asp-Glu-Thr-Asp(SEQ ID NO: 24)-Y, X-Leu-Glu-His-Asp(SEQ ID NO: 25)-Y, X-Asp-Glu-His-Asp(SEQ ID NO: 26)-Y, X-Trp-Glu-His-Asp(SEQ ID NO: 27)-Y, X-Leu-Glu-Thr-Asp(SEQ ID NO: 28)-Y, X-Asp-Glu-Val-Asp(SEQ ID NO: 29)-Y, X-Val-Glu-His-Asp(SEQ ID NO: 30)-Y, and X-Ile-Glu-Ala-Asp(SEQ ID NO: 31)-Y, wherein X and Y are each independently a polypeptide comprising from one to about 15 amino acids and the C-terminal amino acid of Y is covalently linked to said substrate.

12. The conjugate of claim 2, wherein the conjugate has the chemical structure
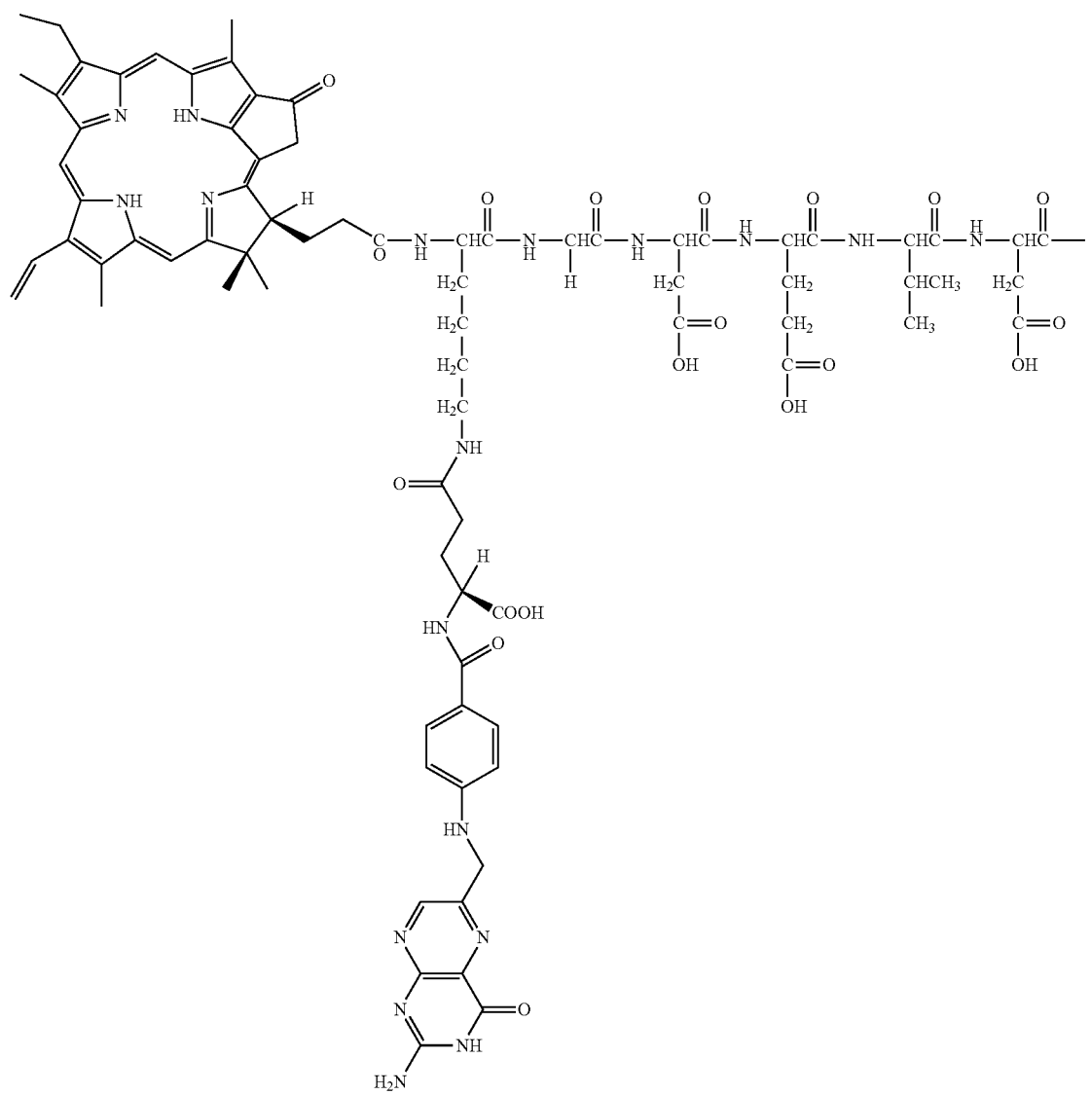

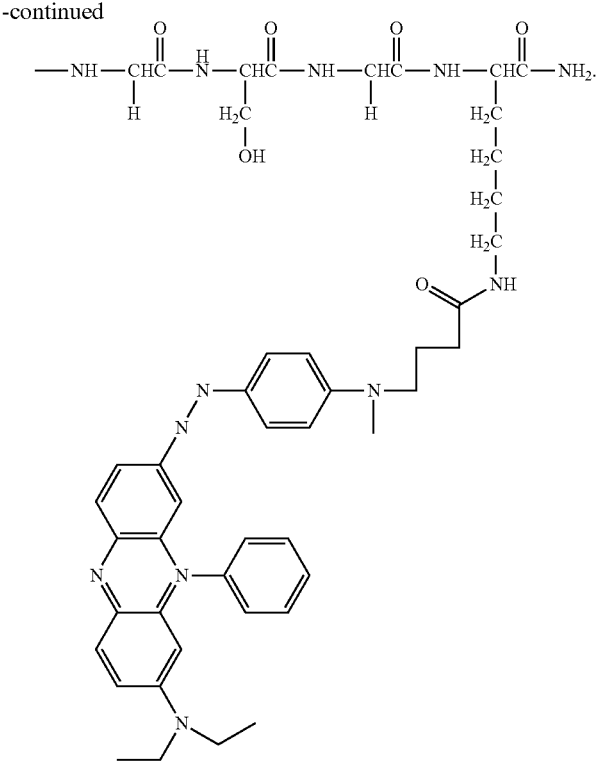

13. A pharmaceutical composition comprising the conjugate of claim 1, and a pharmaceutically acceptable carrier.

14. A conjugate comprising a substrate that comprises
(a) a recognition sequence cleavable by a proteolytic enzyme recognizing said recognition sequence, wherein said recognition sequence is selected from the group consisting of Asp-Glu-Val-Ile(SEQ ID NO:1), Asp-Glu-Thr-Asp(SEQ ID NO:2), Leu-Glu-His-Asp(SEQ ID NO:3), Asp-Glu-His-Asp(SEQ ID NO:4), Trp-Glu-His-Asp(SEQ ID NO:5), Leu-Glu-Thr-Asp(SEQ ID NO:6), Asp-Glu-Val-Asp(SEQ ID NO:7), Val-Glu-His-Asp (SEQ ID NO:8), Ile-Glu-Ala-Asp(SEQ ID NO:9); Gly-Asp-Glu-Val-Asp-Gly-Ser-Gly-Lys (SEQ ID NO:10); and Lys-Gly-Asp-Glu-Val-Asp-Gly-Ser-Gly-Lys (SEQ ID NO:11);
(b) a photoactivatable killing agent, wherein said photoactivatable killing agent is selected from the group consisting of a pyropheophorbide, a porphyrin or isomer thereof, an expanded porphyrin, a chlorin, a bacteriochlorin, a phthalocyanine, a naphthalocyanine, a hypericin, a cationic dye, a purpurin, a psoralen, and a merocyanine 540; and
(c) a quencher, wherein said quencher is selected from the group consisting of a carotenoid, an amine, a phenol, a sulfide, a bilirubin, a biliverdin, a nitroso compound, a nitrone compound, an N-oxy compound and a dye selected from the group consisting of a metal complex dye, a cyanine dye, a stilbene quinone dye, and an azomethine dye, wherein the dye is other than the photoactivatable killing agent cationic dye;

wherein said photoactivatable killing agent is operably linked to one end of said substrate and said quencher is operably linked to another end of said substrate, wherein said proteolytic enzyme is capable of recognizing said recognition sequence in said substrate, wherein said conjugate is capable of providing an intact form and a cleaved form, wherein in said conjugate in said intact form, the distance between said photoactivatable killing agent and said quencher is sufficient for said quencher to quench photoactivation of said photoactivatable killing agent; and wherein in said conjugate in said cleaved form, said photoactivatable killing agent is separated from said quencher as a result of said enzyme contacting said substrate for a period of time and conditions sufficient to proteolytically cleave said recognition sequence, thereby said photoactivatable killing agent is not quenched by said quencher.

15. A method of treating a cancerous target tissue comprising the steps of:
(a) administering to the target tissue of patient in need thereof a conjugate of claim 4; and
(b) irradiating the photoactivatable killing agent of the conjugate, thereby killing said cancerous target tissue, wherein the killing of the cancerous tissue provides proteolytic cleaving of the conjugate cell death protease recognition sequence, wherein said cleaving removes the quencher from the conjugate, thereby allowing fluorescence detection of the photoactivatable killing agent fluorophore.

* * * * *

SEQUENCE LISTING

<160> NUMBER OF SEQ ID NOS: 31

<210> SEQ ID NO 1
<211> LENGTH: 4
<212> TYPE: PRT
<213> ORGANISM: Artificial Sequence
<220> FEATURE:
<223> OTHER INFORMATION: substrate sequence

<400> SEQUENCE: 1

Asp Glu Val Ile
1

<210> SEQ ID NO 2
<211> LENGTH: 4
<212> TYPE: PRT
<213> ORGANISM: Artificial Sequence
<220> FEATURE:
<223> OTHER INFORMATION: substrate sequence

<400> SEQUENCE: 2

Asp Glu Thr Asp
1

<210> SEQ ID NO 3

```
<211> LENGTH: 4
<212> TYPE: PRT
<213> ORGANISM: Artificial Sequence
<220> FEATURE:
<223> OTHER INFORMATION: substrate sequence

<400> SEQUENCE: 3

Leu Glu His Asp
1

<210> SEQ ID NO 4
<211> LENGTH: 4
<212> TYPE: PRT
<213> ORGANISM: Artificial Sequence
<220> FEATURE:
<223> OTHER INFORMATION: substrate sequence

<400> SEQUENCE: 4

Asp Glu His Asp
1

<210> SEQ ID NO 5
<211> LENGTH: 4
<212> TYPE: PRT
<213> ORGANISM: Artificial Sequence
<220> FEATURE:
<223> OTHER INFORMATION: substrate sequence

<400> SEQUENCE: 5

Trp Glu His Asp
1

<210> SEQ ID NO 6
<211> LENGTH: 4
<212> TYPE: PRT
<213> ORGANISM: Artificial Sequence
<220> FEATURE:
<223> OTHER INFORMATION: substrate sequence

<400> SEQUENCE: 6

Leu Glu Thr Asp
1

<210> SEQ ID NO 7
<211> LENGTH: 4
<212> TYPE: PRT
<213> ORGANISM: Artificial Sequence
<220> FEATURE:
<223> OTHER INFORMATION: substrate sequence

<400> SEQUENCE: 7

Asp Glu Val Asp
1

<210> SEQ ID NO 8
<211> LENGTH: 4
<212> TYPE: PRT
<213> ORGANISM: Artificial Sequence
<220> FEATURE:
<223> OTHER INFORMATION: substrate sequence

<400> SEQUENCE: 8

Val Glu His Asp
1

<210> SEQ ID NO 9
<211> LENGTH: 4
<212> TYPE: PRT
```

```
<213> ORGANISM: Artificial Sequence
<220> FEATURE:
<223> OTHER INFORMATION: substrate sequence

<400> SEQUENCE: 9

Ile Glu Ala Asp
1

<210> SEQ ID NO 10
<211> LENGTH: 9
<212> TYPE: PRT
<213> ORGANISM: Artificial Sequence
<220> FEATURE:
<223> OTHER INFORMATION: substrate sequence

<400> SEQUENCE: 10

Gly Asp Glu Val Asp Gly Ser Gly Lys
1               5

<210> SEQ ID NO 11
<211> LENGTH: 10
<212> TYPE: PRT
<213> ORGANISM: Artificial Sequence
<220> FEATURE:
<223> OTHER INFORMATION: substrate sequence

<400> SEQUENCE: 11

Lys Gly Asp Glu Val Asp Gly Ser Gly Lys
1               5                   10

<210> SEQ ID NO 12
<211> LENGTH: 20
<212> TYPE: DNA
<213> ORGANISM: Artificial Sequence
<220> FEATURE:
<223> OTHER INFORMATION: ssDNA that is complementary to the loop
      sequence of MB

<400> SEQUENCE: 12
aatgcatgtc acaggcggga                                                   20

<210> SEQ ID NO 13
<211> LENGTH: 6
<212> TYPE: PRT
<213> ORGANISM: Artificial Sequence
<220> FEATURE:
<223> OTHER INFORMATION: doxorubicin-coupled peptide

<400> SEQUENCE: 13

His Ser Ser Lys Leu Gln
1               5

<210> SEQ ID NO 14
<211> LENGTH: 12
<212> TYPE: PRT
<213> ORGANISM: Artificial Sequence
<220> FEATURE:
<223> OTHER INFORMATION: substrate sequence

<400> SEQUENCE: 14

Gly Gly His Ser Ser Lys Leu Gln Gly Ser Gly Lys
1               5                   10

<210> SEQ ID NO 15
<211> LENGTH: 8
<212> TYPE: PRT
<213> ORGANISM: Artificial Sequence
<220> FEATURE:
```

```
<223> OTHER INFORMATION: substrate sequence

<400> SEQUENCE: 15

Gly Gly His Ser Ser Lys Leu Gln
1               5

<210> SEQ ID NO 16
<211> LENGTH: 15
<212> TYPE: PRT
<213> ORGANISM: Artificial Sequence
<220> FEATURE:
<223> OTHER INFORMATION: substrate sequence

<400> SEQUENCE: 16

Gly Asp Glu Val Asp Ser Gly Lys His Ser Ser Lys Leu Gln Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: substrate sequence

<400> SEQUENCE: 17

Ser Gln Asn Tyr Pro Ile Val Gln
1               5

<210> SEQ ID NO 18
<211> LENGTH: 28
<212> TYPE: DNA
<213> ORGANISM: Artificial Sequence
<220> FEATURE:
<223> OTHER INFORMATION: single stranded DNA

<400> SEQUENCE: 18
agctaggaaa caccaaagat gatatttg                                      28

<210> SEQ ID NO 19
<211> LENGTH: 20
<212> TYPE: DNA
<213> ORGANISM: Artificial Sequence
<220> FEATURE:
<223> OTHER INFORMATION: single stranded DNA

<400> SEQUENCE: 19
tcccgcctgt gacatgcatt                                               20

<210> SEQ ID NO 20
<211> LENGTH: 38
<212> TYPE: DNA
<213> ORGANISM: Artificial Sequence
<220> FEATURE:
<223> OTHER INFORMATION: single stranded DNA

<400> SEQUENCE: 20
gcgagagcta ggaaacacca aagatgatat ttgctcgc                           38

<210> SEQ ID NO 21
<211> LENGTH: 30
<212> TYPE: DNA
<213> ORGANISM: Artificial Sequence
<220> FEATURE:
<223> OTHER INFORMATION: single stranded DNA

<400> SEQUENCE: 21
gcgagtcccg cctgtgacat gcattctcgc                                    30
```

<210> SEQ ID NO 22
<211> LENGTH: 20
<212> TYPE: DNA
<213> ORGANISM: Artificial Sequence
<220> FEATURE:
<223> OTHER INFORMATION: single stranded DNA

<400> SEQUENCE: 22
aatgcatgtc acaggcggga                                              20

<210> SEQ ID NO 23
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 23

Xaa Asp Glu Val Ile Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 24

Xaa Asp Glu Thr Asp Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)

```
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 25

Xaa Leu Glu His Asp Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 26

Xaa Asp Glu His Asp Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 27

Xaa Trp Glu His Asp Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
```

```
<221> NAME/KEY: misc_feature
<222> LOCATION: (6)..(6)
<223> OTHER INFORMATION: Xaa can be any naturally occurring amino acid

<400> SEQUENCE: 28

Xaa Leu Glu Thr Asp Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 29

Xaa Asp Glu Val Asp Xaa
1               5

<210> SEQ ID NO 30
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 30

Xaa Val Glu His Asp Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: substrate sequence
<220> FEATURE:
<221> NAME/KEY: misc_feature
<223> OTHER INFORMATION: Xaa refers to any molecule
<220> FEATURE:
```

-continued

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Xaa Ile Glu Ala Asp Xaa
1               5
```